United States Patent
Souers et al.

(10) Patent No.: US 7,071,182 B2
(45) Date of Patent: Jul. 4, 2006

(54) ANTAGONISTS OF MELANIN CONCENTRATING HORMONE EFFECTS ON THE MELANIN CONCENTRATING HORMONE RECEPTOR

(75) Inventors: Andrew J. Souers, Evanston, IL (US); Christine A. Collins, Skokie, IL (US); Ju Gao, Gurnee, IL (US); Andrew S. Judd, Grayslake, IL (US); Philip R. Kym, Libertyville, IL (US); Mathew M. Mulhern, Hainesville, IL (US); Hing L. Sham, Vernon Hills, IL (US); Dariusz Wodka, Monmouth Junction, NJ (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/022,453

(22) Filed: Dec. 22, 2004

(65) Prior Publication Data
US 2005/0277638 A1    Dec. 15, 2005

Related U.S. Application Data

(60) Provisional application No. 60/532,301, filed on Dec. 23, 2003.

(51) Int. Cl.
*A61K 31/55*    (2006.01)
*A61K 31/5377*    (2006.01)
*A61K 31/454*    (2006.01)
*A61K 31/416*    (2006.01)
*A61K 31/4439*    (2006.01)

(52) U.S. Cl. .......................... 514/210.21; 514/217.09; 514/234.5; 514/254.06; 514/322; 514/338; 514/403; 540/603; 544/119; 544/357; 544/371; 546/199; 546/275.7; 548/360.1

(58) Field of Classification Search ................ 540/603; 544/119, 357, 371; 546/199, 275.7; 548/360.1
See application file for complete search history.

(56) References Cited

FOREIGN PATENT DOCUMENTS

| WO | 2003015769 | 2/2003 |
| WO | WO 2004078748 | * 9/2004 |

OTHER PUBLICATIONS

CAS Abstract attached.*

* cited by examiner

*Primary Examiner*—Joseph K. McKane
*Assistant Examiner*—Jason M. Nolan
(74) *Attorney, Agent, or Firm*—Johanna M. Corbin

(57) ABSTRACT

The present invention relates to the antagonism of the effects of melanin-concentrating hormone (MCH) through the melanin concentrating hormone receptor which is useful for the prevention or treatment of eating disorders, weight gain, obesity, abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders.

19 Claims, No Drawings

ANTAGONISTS OF MELANIN CONCENTRATING HORMONE EFFECTS ON THE MELANIN CONCENTRATING HORMONE RECEPTOR

This application claims priority to U.S. Provisional Patent Application Ser. No. 60/532,301, filed Dec. 23, 2003, which is incorporated herein by reference.

TECHNICAL FIELD

The present invention relates to the antagonism of the effects of melanin-concentrating hormone (MCH) through the melanin concentrating hormone receptor which is useful for the prevention or treatment of eating disorders, weight gain, obesity, abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders.

BACKGROUND OF THE INVENTION

Obesity is a major cause and contributor to health problems such as type II diabetes, coronary heart disease, increased incidence of certain forms of cancer, and respiratory complications. It is a disease that is increasing at an alarming rate due to increased availability of high-fat diets, genetic susceptibility, and a more sedentary way of life in modern society. Obesity can be defined as weight gain resulting from a mismatch of energy intake and energy expenditure. Food intake and energy metabolism are regulated, in part, by the interaction of neuropeptides and their receptors. Recently, the role that the hormone leptin plays in controlling appetite has been elucidated.

Leptin is a peptide hormone produced by fat cells, regulating both food intake and and metabolism by acting on leptin receptors in the hypothalamus. Increased fat stores leads to increased secretion of leptin, resulting in a signal to the hypothalamus to decrease food intake, whereas decreases in adiposity result in lower leptin levels and a stimulation of food intake. Melanin-concentrating hormone (MCH) has been identified as an orexigenic peptide that counterbalances the activity of leptin.

MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. Mice lacking MCH are hypophagic and lean with increased metabolic rate, whereas animals over-expressing MCH gain excess weight on both standard and high fat diets. MCH is thought to have effects on other nervous system functions as well (Nahon J L., The melanin-concentrating hormone: from the peptide to the gene. Crit Rev Neurobiol 8:221–262, 1994). An orphan G-protein coupled receptor (GPCR) was recently identified as a receptor for MCH.

Although there exists current pharmacologic therapies used to treat obesity, none of the current therapies achieve the U.S. Food and Drug Administration criteria for benefit measured by a 5% difference in mean weight loss, as weight loss efficacy is diminished by reduction of patient adherence to pharmacological therapy due to side effects of the drugs. Some of the side effects associated with current therapies include increased heart rate and blood pressure, and uncontrolled excretion of fat in stools. Thus, there exists a medical need for agents capable of preventing or treating eating disorders, weight gain and obesity, that at the same time, have improved efficacy and safety.

Therefore, current investigation of novel MCH antagonists which may lead to an orally active new and better treatment of eating disorders, weight gain and obesity would be of great importance to current society.

SUMMARY OF THE INVENTION

The present invention is directed to compounds of formula (I),

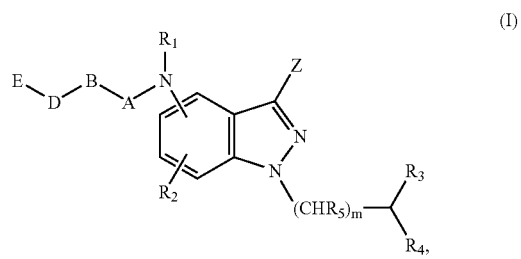

or a therapeutically suitable salt or prodrug thereof, wherein

A is selected from the group consisting of —C(O)—, —S(O)—, —S(O)$_2$—, —C(=NR$_a$)—, and —C(=S)—;

B is selected from the group consisting of alkylene, alkenyl, carbonylalkyl, cycloalkyl, —NR$_b$— and —NR$_b$-alkyl;

D is a bond or is selected from the group consisting of alkylene, aryl, arylalkyl, heterocycle and heterocyclealkyl;

E is selected from the group consisting of alkyl, alkyl-C(O)—, alkyl-C(O)—NH—, alkyl-NH—, alkyl-NH—C(O)—, alkyl-NH—S(O)$_2$—, alkoxy, alkyl-S—, alkyl-S(O)$_2$—, alkyl-S(O)$_2$—NH—, aryl, aryl-C(O)—, aryl-C(O)—NH—, aryl-C=N—O—, aryl-NH—, aryl-NH—C(O)—, aryl-NH—S(O)$_2$—, aryloxy, aryl-S—, aryl-S-alkyl-C(O)—, aryl-S(O)$_2$—, aryl-S(O)$_2$—NH—, arylalkyl-C(O)—, arylalkyl-C(O)—NH—, arylalkyl-NH—, arylalkyl-NH—C(O)—, arylalkyl-NH—S(O)$_2$—, arylalkoxy, arylalkyl-S—, arylalkyl-S(O)$_2$—, arylalkyl-S(O)$_2$—NH—, cycloalkyl, cycloalkyl-C(O)—, cycloalkyl-C(O)—NH—, cycloalkyl-NH—, cycloalkyl-NH—C(O)—, cycloalkyl-NH—S(O)$_2$—, cycloalkoxy, cycloalkyl-S—, cycloalkyl-S(O)$_2$—, cycloalkyl-S(O)$_2$—NH—, cycloalkenyl, cycloalkenylalkyl, cycloalkenyl-C(O)—, cycloalkenyl-C(O)—NH—, cycloalkenyl-NH—, cycloalkenyl-NH—C(O)—, cycloalkenyl-NH—S(O)$_2$—, cycloalkenyloxy, cycloalkenyl-S—, cycloalkenyl-S(O)$_2$—, cycloalkenyl-S(O)$_2$—NH—, heterocycle, heterocycle-C(O)—, heterocycle-C(O)—NH—, heterocycle-NH—, heterocycle-NH—C(O)—, heterocycle-NH—S(O)$_2$—, heterocycle-O—, heterocycle-S—, heterocycle-S(O)$_2$—, heterocycle-S(O)$_2$—NH—, heterocyclealkyl-C(O)—, heterocyclealkyl-C(O)—NH—, heterocyclealkyl-NH—, heterocyclealkyl-NH—C(O)—, heterocyclealkyl-NH—S(O)$_2$—, heterocyclealkyl-O—, heterocyclealkyl-S—, heterocyclealkyl-S(O)$_2$— and heterocyclealkyl-S(O)$_2$—NH—;

R$_1$ is selected from the group consisting of hydrogen and alkyl;

R$_2$ is selected from the group consisting of hydrogen, halogen, alkyl and alkoxy;

R$_3$ is R$_c$R$_d$N—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_a$ is selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ are each independently selected from the group consisting of hydrogen, alkyl, aryl, arylalkyl, cycloalkyl, cycloalkenylalkyl, heterocycle, heterocyclealkyl and hydroxyalkyl, or $R_c$ and $R_d$ taken together with the atoms to which they are attached form a heterocycle;

Z is selected from the group consisting of hydrogen, alkyl and halogen; and m is 1, 2 or 3;

provided that:

if B is $NR_b$— or $NR_b$-alkyl, then

D is selected from the group consisting of alkyl, aryl, arylalkyl, heterocycle and heterocyclealkyl.

Another embodiment of the present invention encompasses the use of the compounds of the present invention for the treatment of obesity comprising administration of said compounds to a patient in need of such treatment.

A further embodiment of the present invention encompasses the use of the compounds of the present invention for the treatment of disorders that are mediated by MCH through the MCH receptor such as abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders comprising administering a therapeutically effective amount of a compound of formula (I) to a patient in need thereof.

According to another embodiment, the present invention is directed to a pharmaceutical composition comprising a therapeutically effective amount of a compound of formula (I) in combination with a pharmaceutically suitable carrier.

DETAILED DESCRIPTION OF THE INVENTION

The principal embodiment of the present invention is directed toward compounds of formula (I) and their use in the treatment of disorders mediated by MCH comprising administration of a therapeutically effective amount of a compound of formula (I) in need of such treatment.

Accordingly, the principle embodiment of the present invention is directed toward a compound of formula (I),

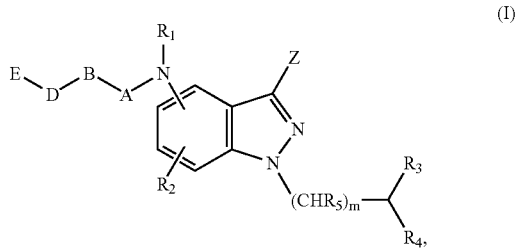

(I)

or a therapeutically suitable salt or prodrug thereof, wherein A is selected from the group consisting of —C(O)—, —S(O)—, —S(O)$_2$—, —C(=NR$_a$)—, and —C(=S)—; B is selected from the group consisting of alkylene, alkenyl, carbonylalkyl, cycloalkyl, —NR$_b$—, and —NR$_b$-alkyl; D is a bond or is selected from the group consisting of alkylene, aryl, arylalkyl, heterocycle and heterocyclealkyl; E is selected from the group consisting of alkyl, alkyl-C(O)—, alkyl-C(O)—NH—, alkyl-NH—, alkyl-NH—C(O)—, alkyl-NH—S(O)$_2$—, alkoxy, alkyl-S—, alkyl-S(O)$_2$—, alkyl-S(O)$_2$—NH—, aryl, aryl-C(O)—, aryl-C(O)—NH—, aryl-C=N—O—, aryl-NH—, aryl-NH—C(O)—, aryl-NH—S(O)$_2$—, aryloxy, aryl-S—, aryl-S-alkyl-C(O)—, aryl-S(O)$_2$—, aryl-S(O)$_2$—NH—, arylalkyl-C(O)—, arylalkyl-C(O)—NH—, arylalkyl-NH—, arylalkyl-NH—C(O)—, arylalkyl-NH—S(O)$_2$—, arylalkoxy, arylalkyl-S—, arylalkyl-S(O)$_2$—, arylalkyl-S(O)$_2$—NH—, cycloalkyl, cycloalkyl-C(O)—, cycloalkyl-C(O)—NH—, cycloalkyl-NH—, cycloalkyl-NH—C(O)—, cycloalkyl-NH—S(O)$_2$—, cycloalkoxy, cycloalkyl-S—, cycloalkyl-S(O)$_2$—, cycloalkyl-S(O)$_2$—NH—, cycloalkenyl, cycloalkenylalkyl, cycloalkenyl-C(O)—, cycloalkenyl-C(O)—NH—, cycloalkenyl-NH—, cycloalkenyl-NH—C(O)—, cycloalkenyl-NH—S(O)$_2$—, cycloalkenyloxy, cycloalkenyl-S—, cycloalkenyl-S(O)$_2$—, cycloalkenyl-S(O)$_2$—NH—, heterocycle, heterocycle-C(O)—, heterocycle-C(O)—NH—, heterocycle-NH—, heterocycle-NH—C(O)—, heterocycle-NH—S(O)$_2$—, heterocycle-O—, heterocycle-S—, heterocycle-S(O)$_2$—, heterocycle-S(O)$_2$—NH—, heterocyclealkyl-C(O)—, heterocyclealkyl-C(O)—NH—, heterocyclealkyl-NH—, heterocyclealkyl-NH—C(O)—, heterocyclealkyl-NH—S(O)$_2$—, heterocyclealkyl-O—, heterocyclealkyl-S—, heterocyclealkyl-S(O)$_2$—, heterocyclealkyl-S(O)$_2$—NH—; $R_1$ is selected from the group consisting of hydrogen and alkyl; $R_2$ is selected from the group consisting of hydrogen, halogen, alkyl and alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocyclealkyl and hydroxyalkyl, or $R_c$ and $R_d$ taken together with the atoms to which they are attached form a heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, alkyl-S(O)$_2$—, aryl-C(O)—, aryl-C=N—O—, aryl-NH—, aryloxy, aryl-S—, aryl-S-alkyl-C(O)—, aryl-S(O)$_2$—, arylalkyl-C(O)—, arylalkyl-NH—, arylalkoxy, arylalkyl-S(O)$_2$—, cycloalkyl, cycloalkyl-C(O)—, cycloalkyl-NH—, cycloalkoxy, cycloalkyl-S(O)$_2$—, cycloalkenylalkyl, heterocycle-C(O)—, heterocycle-NH—, heterocycle-O—, heterocycle-S(O)$_2$—, heterocyclealkyl-C(O)—, heterocyclealkyl-NH—, heterocyclealkyl-O— and heterocyclealkyl-S(O)$_2$—; R$_1$ is selected from the group consisting of hydrogen and alkyl; R$_2$ is selected from the group consisting of hydrogen, halogen, alkyl and alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ are each independently selected from the group consisting of hydrogen, alkyl, aryl, arylalkyl, cycloalkyl, cycloalkenylalkyl, heterocycle, heterocyclealkyl and hydroxyalkyl or R$_c$ and R$_d$ taken together with the atoms to which they are attached form a heterocycle; Z is selected from the group consisting of hydrogen, alkyl and halogen; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, alkyl-S(O)$_2$—, aryl-C(O)—, aryl-C=N—O—, aryl-NH—, aryloxy, aryl-S—, aryl-S-alkyl-C(O)—, aryl-S(O)$_2$—, arylalkyl-C(O)—, arylalkyl-NH—, arylalkoxy, arylalkyl-S(O)$_2$—, cycloalkyl, cycloalkyl-C(O)—, cycloalkyl-NH—, cycloalkoxy, cycloalkyl-S(O)$_2$—, cycloalkenylalkyl, heterocycle-C(O)—, heterocycle-NH—, heterocycle-O—, heterocycle-S(O)$_2$—, heterocyclealkyl-C(O)—, heterocyclealkyl-NH—, heterocyclealkyl-O— and heterocyclealkyl-S(O)$_2$—; R$_1$ is selected from the group consisting of hydrogen and alkyl; R$_2$ is selected from the group consisting of hydrogen, halogen, alkyl and alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ are each independently selected from the group consisting of hydrogen, alkyl, aryl, arylalkyl, cycloalkyl, cycloalkenylalkyl, heterocycle, heterocyclealkyl and hydroxyalkyl or R$_c$ and R$_d$ taken together with the atoms to which they are attached form a heterocycle; Z is selected from the group consisting of hydrogen, alkyl and halogen; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; R$_1$ is selected from the group consisting of hydrogen and alkyl; R$_2$ is selected from the group consisting of hydrogen, halogen, alkyl and alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ are each independently selected from the group consisting of hydrogen, alkyl, aryl, arylalkyl, cycloalkyl, cycloalkenylalkyl, heterocycle, heterocyclealkyl and hydroxyalkyl or R$_c$ and R$_d$ taken together with the atoms to which they are attached form a heterocycle; Z is selected from the group consisting of hydrogen, alkyl and halogen; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; R$_1$ is selected from the group consisting of hydrogen and alkyl; R$_2$ is selected from the group consisting of hydrogen, halogen, alkyl and alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocyclealkyl and hydroxyalkyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl and alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocyclealkyl and hydroxyalkyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl —NH—, alkoxy, aryl-C(O)—, aryl-C=N—O—, aryl —NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl and alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocyclealkyl and hydroxyalkyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl —NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen and alkyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen and alkyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—; $R_1$ is selected from the group consisting of hydrogen and alkyl; $R_2$ is selected from the group consisting of hydrogen, halogen, alkyl and alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 4 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 4 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl and alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 5 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 5 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl—NH—, alkoxy, aryl-C(O)—, aryl-C=N—O—, aryl—NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a pyrrolidine; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form an oxazolidinyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 2,3-dihydro-1H-indole; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form

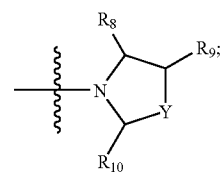

Y is selected from the group consisting of O, $NR_j$, $CHR_j$ and C(O); Z is selected from the group consisting of hydrogen, alkyl and halogen; $R_8$ is selected from the group consisting of hydrogen and alkyl; $R_9$ and $R_{10}$ are each individually selected from the group consisting of oxo, hydrogen and alkyl; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl- C=N—O—, aryl-NH—, aryloxy, aryl-S—, aryl-S-alkyl-C (O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form

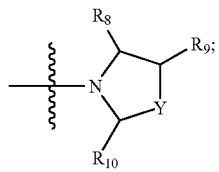

Y is selected from the group consisting of O, $NR_j$, $CHR_j$ and C(O); Z is selected from the group consisting of hydrogen, alkyl and halogen; $R_8$ is selected from the group consisting of hydrogen and alkyl; $R_9$ and $R_{10}$ are each individually selected from the group consisting of oxo, hydrogen and alkyl; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl —NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 6 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a morpholine ring; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a piperidine ring; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl —NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a piperazine ring; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form

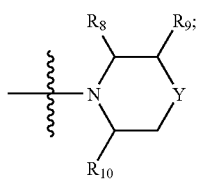

Y is selected from the group consisting of O, $NR_j$, $CHR_j$ and C(O); Z is selected from the group consisting of hydrogen, alkyl and halogen; $R_8$ is selected from the group consisting of hydrogen and alkyl; and $R_9$ and $R_{10}$ are each individually selected from the group consisting of oxo, hydrogen and alkyl; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, hetero-cycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form

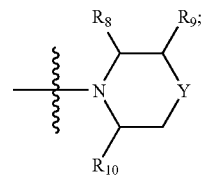

Y is selected from the group consisting of O, $NR_j$, $CHR_j$ and C(O); Z is selected from the group consisting of hydrogen, alkyl and halogen; $R_8$ is selected from the group consisting of hydrogen and alkyl; $R_9$ and $R_{10}$ are each individually selected from the group consisting of oxo, hydrogen and alkyl; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 7 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 7 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form an azepan ring; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl —NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form

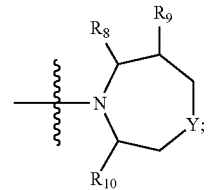

Y is selected from the group consisting of O, $NR_j$, $CHR_j$ and C(O); Z is selected from the group consisting of hydrogen, alkyl and halogen; $R_8$ is selected from the group consisting of hydrogen and alkyl; $R_9$ and $R_{10}$ are each individually selected from the group consisting of oxo, hydrogen and alkyl; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is selected from the group consisting of alkylene and alkenyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form

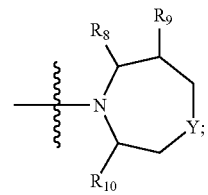

Y is selected from the group consisting of O, $NR_j$, $CHR_j$ and C(O); Z is selected from the group consisting of hydrogen, alkyl and halogen; $R_8$ is selected from the group consisting of hydrogen and alkyl; $R_9$ and $R_{10}$ are each individually selected from the group consisting of oxo, hydrogen and alkyl; and m is 1, 2 or 3; provided that: if B is NR$_b$— or NR$_b$-alkyl, then D is selected from the group consisting of alkyl, aryl, arylalkyl, heterocycle and heterocyclealkyl.

The compounds of the present invention mediate the action of MCH through the MCH receptor, therefore, the compounds of the present invention are useful in treating disorders that are mediated by MCH. In the principal embodiment of the present invention there is provided a method of treating disorders mediated by MCH through the MCH receptor comprising administration of a therapeutically effective amount of a compound of formula (I). Disorders that are mediated by MCH through the MCH receptor are obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Therefore the compounds of the present invention are useful in treating obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders.

According to another embodiment of the present invention, there is provided a method of treating disorders by inhibiting the effects of melanin concentrating hormone (MCH) through the melanin concentrating hormone receptor, comprising administering a therapeutically effective amount of a compound of formula (I).

According to another embodiment of the present invention, there is provided a method of treating obesity by inhibiting the effects of melanin concentrating hormone (MCH) through the melanin concentrating hormone receptor, comprising administering a therapeutically effective amount of a compound of formula (I).

According to another embodiment of the present invention, there is provided a method of treating abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders by inhibiting the effects of melanin concentrating hormone (MCH) through the melanin concentrating hormone receptor, comprising administering a therapeutically effective amount of a compound of formula (I).

According to another embodiment of the present invention, there is provided a pharmaceutical composition comprising a therapeutically effective amount of a compound of formula (I) in combination with a pharmaceutically suitable carrier.

DEFINITIONS

As used throughout this specification and the appended claims, the following terms have the following meanings:

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkyl-C(O)—," as used herein, refers to an alkyl group, as defined herein, appended to the parent molecular moiety through a C(O)-group, as defined herein.

The term "alkyl-C(O)—NH—," as used herein, refers to a alkyl-C(O) group, as defined herein, appended to the parent molecular moiety through a —NH-group, as defined herein.

The term "alkyl-NH—," as used herein, refers to a alkyl group, as defined herein, appended to the parent molecular moiety through an —NH-group, as defined herein.

The term "alkyl-NH—C(O)—," as used herein, refers to a alkyl-NH-group, as defined herein, appended to the parent molecular moiety through a —C(O)-group, as defined herein.

The term "alkyl-NH—S(O)$_2$—," as used herein, refers to a alkyl-NH-group, as defined herein, appended to the parent molecular moiety through a —S(O)$_2$-group, as defined herein.

The term "alkyl-S—," as used herein, refers to a alkyl group, as defined herein, appended to the parent molecular moiety through a—S-group, as defined herein.

The term "alkyl-S(O)$_2$—," as used herein, refers to an alkyl group, as defined herein, appended to the parent molecular moiety through a —S(O)$_2$-group, as defined herein.

The term "alkyl-S(O)$_2$—NH—," as used herein, refers to a alkyl-S(O)$_2$-group, as defined herein, appended to the parent molecular moiety through a —NH-group, as defined herein.

The term "alkylene," denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 0, 1, 2, or 3 substituents independently selected from alkenyl, alkoxy, alkoxyalkyl, alkoxycarbonyl, alkyl, alkylcarbonyl, alkylcarbonyloxy, alkynyl, aryloxy, arylalkenyl, carboxy, carboxyalkyl, cyano, cyanoalkyl, formyl, halogen, haloalkyl, haloalkoxy, heterocycle, hydroxy, hydroxyalkyl, nitro, R$_e$R$_f$N—, R$_e$R$_f$N—C(O)—, aryl and heterocycle, wherein the aryl of aryloxy, the substituent aryl and the substituent heterocycle can each be substituted with 0, 1, 2, or 3 substituents selected from the group consisting of alkenyl, alkoxy, alkoxycarbonyl, alkyl, alkylcarbonyl, carboxy, carboxyalkyl, cyano, cyanoalkyl, halogen, haloalkyl, haloalkoxy, hydroxy, hydroxyalkyl and nitro, wherein R$_e$ and $R_f$ are each individually selected from the group consisting of hydrogen, alkyl and alkylcarbonyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkenyl" as used herein, refers to an aryl group, as defined herein, appended to the parent molecular moiety through an alkenyl group, as defined herein. Representative examples of arylalkenyl include, but are not limited to, prop-1-enylbenzene, 1-(prop-1-enyl)naphthalene and the like.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, refers to an arylcarbonyl group, as defined herein, appended to the parent molecular moiety through a carbonyl group, as defined herein. Representative examples of arylcarbonylalkyl include, but are not limited to, propiophenone, 1-(1-naphthyl)propan-1-one and the like.

The term "aryloxy," as used herein, refers to an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl," as used herein, refers to an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylsulfonyl" as used herein, refers to an aryl group, as defined herein, appended to the parent molecular moiety through a sulfonyl group, as defined herein. Representative examples of arylsulfonyl include but are not limited to (ethylsulfonyl)benzene, 1-(ethylsulfonyl)naphthalene and the like.

The term "aryl-C(O)—," as used herein, refers to a aryl group, as defined herein, appended to the parent molecular moiety through an —C(O)— group, as defined herein.

The term "aryl-C(O)—NH—," as used herein, refers to a aryl-C(O)— group, as defined herein, appended to the parent molecular moiety through a —NH— group, as defined herein.

The term "aryl-C=N—O—," as used herein, refers to a aryl group, as defined herein, appended to the parent molecular moiety through a —C=N—O— group, as defined herein.

The term "aryl-NH—," as used herein, refers to a aryl group, as defined herein, appended to the parent molecular moiety through a —NH— group, as defined herein.

The term "aryl-NH—C(O)—," as used herein, refers to a aryl-NH-group, as defined herein, appended to the parent molecular moiety through an —C(O)-group, as defined herein.

The term "aryl-NH—S(O)$_2$—," as used herein, refers to a aryl-NH— group, as defined herein, appended to the parent molecular moiety through a —S(O)$_2$-group, as defined herein.

The term "aryloxy," as used herein, refers to an aryl group, as defined herein, appended to the parent molecular moiety through an oxy group, as defined herein.

The term "aryl-S—," as used herein, refers to a aryl group, as defined herein, appended to the parent molecular moiety through an —S— group, as defined herein.

The term "aryl-S-alkyl-C(O)—," as used herein, refers to a aryl-S-alkyl group, as defined herein, appended to the parent molecular moiety through a —C(O)— group, as defined herein.

The term "aryl-S(O)$_2$—," as used herein, refers to a aryl group, as defined herein, appended to the parent molecular moiety through a —S(O)$_2$-group, as defined herein.

The term "aryl-S(O)$_2$—NH—," as used herein, refers to a aryl-S(O)$_2$— group, as defined herein, appended to the parent molecular moiety through a —NH-group, as defined herein.

The term "arylalkyl-C(O)—," as used herein, refers to a arylalkyl group, as defined herein, appended to the parent molecular moiety through a —C(O)-group, as defined herein.

The term "arylalkyl-C(O)—NH—," as used herein, refers to a arylalkyl-C(O)— group, as defined herein, appended to the parent molecular moiety through a —NH— group, as defined herein.

The term "arylalkyl-NH—," as used herein, refers to a arylalkyl group, as defined herein, appended to the parent molecular moiety through a —NH— group, as defined herein.

The term "arylalkyl-NH—C(O)—," as used herein, refers to a arylalkyl-NH— group, as defined herein, appended to the parent molecular moiety through a —C(O)— group, as defined herein.

The term "arylalkyl-NH—S(O)$_2$—," as used herein, refers to a arylalkyl-NH— group, as defined herein, appended to the parent molecular moiety through a —S(O)$_2$— group, as defined herein.

The term "arylalkoxy," as used herein, refers to a aryl group, as defined herein, appended to the parent molecular moiety through a alkoxy group, as defined herein.

The term "arylalkyl-S—," as used herein, refers to a arylalkyl group, as defined herein, appended to the parent molecular moiety through a —S-group, as defined herein.

The term "arylalkyl-S(O)$_2$—," as used herein, refers to a arylalkyl group, as defined herein, appended to the parent molecular moiety through an —S(O)$_2$-group, as defined herein.

The term "arylalkyl-S(O)$_2$—NH—," as used herein, refers to an arylalkyl-S(O)$_2$—NH— group, as defined herein, appended to the parent molecular moiety through a —NH— group, as defined herein.

The term "biarylalkyl" as used herein, refers to two aryl groups, as defined herein, appended to the parent molecular moiety through an alkyl group, as defined herein. Representative examples of biarylalkyl include but are not limited to (1-phenylbutyl)benzene and the like.

The term "carbonyl," as used herein, refers to a —C(O)— group.

The term "carbonylalkyl," as used herein, refers to a carbonyl group, as defined herein, appended to the parent molecular moiety through an alkyl group, as defined herein.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo(3.1.1)heptane, bicyclo(2.2.1)heptane, bicyclo(2.2.2)octane, bicyclo(3.2.2)nonane, bicyclo(3.3.1) nonane, and bicyclo(4.2.1)nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo$(3.3.1.0^{3,7})$nonane and tricyclo$(3.3.1.1^{3,7})$decane (adamantane).

The cycloalkyl groups of this invention can be substituted with 0, 1, 2, or 3 substituents independently selected from alkenyl, alkoxy, alkoxyalkyl, alkoxycarbonyl, alkyl, alkylcarbonyl, alkylcarbonyloxy, alkynyl, aryl, aryloxy, arylalkenyl, carboxy, carboxyalkyl, cyano, cyanoalkyl, formyl, halogen, haloalkyl, haloalkoxy, heterocycle, hydroxy, hydroxyalkyl, nitro, $R_eR_fN$— and $R_eR_fN$—C(O)—, wherein $R_e$ and $R_f$ are each individually selected from the group consisting of hydrogen, alkyl and alkylcarbonyl.

The term "cycloalkyl-C(O)—," as used herein, refers to a cycloalkyl group, as defined herein, appended to the parent molecular moiety through a —C(O)— group, as defined herein.

The term "cycloalkyl-C(O)—NH—," as used herein, refers to a cycloalkyl-C(O)— group, as defined herein, appended to the parent molecular moiety through a —NH— group, as defined herein.

The term "cycloalkyl-NH—," as used herein, refers to a cycloalkyl group, as defined herein, appended to the parent molecular moiety through a —NH—, group, as defined herein.

The term "cycloalkyl-NH—C(O)—," as used herein, refers to a cycloalkyl-NH— group, as defined herein, appended to the parent molecular moiety through a —C(O)— group, as defined herein.

The term "cycloalkyl-NH—S(O)$_2$—," as used herein, refers to a cycloalkyl-NH— group, as defined herein, appended to the parent molecular moiety through a —S(O)$_2$— group, as defined herein.

The term "cycloalkoxy," as used herein, refers to a cycloalkyl group, as defined herein, appended to the parent molecular moiety through an oxy group, as defined herein.

The term "cycloalkyl-S—," as used herein, refers to a cycloalkyl group, as defined herein, appended to the parent molecular moiety through an —S— group, as defined herein.

The term "cycloalkyl-S(O)$_2$—," as used herein, refers to a cycloalkyl group, as defined herein, appended to the parent molecular moiety through a —S(O)$_2$— group, as defined herein.

The term "cycloalkyl-S(O)$_2$—NH—," as used herein, refers to a cycloalkyl-S(O)$_2$— group, as defined herein, appended to the parent molecular moiety through a —NH— group, as defined herein.

The term "cycloalkenyl" as used herein, refers to a cycloalkyl group, as defined herein, which contains 1 or 2 double bonds. Examples of cycloalkenyl groups include cyclobutenyl, cyclopentenyl, cyclohexenyl, cycloheptenyl, and cyclooctenyl.

The cycloalkenyl groups of this invention can be substituted with 0, 1, 2, or 3 substituents independently selected from the group consisting of alkenyl, alkoxy, alkoxycarbonyl, alkyl, alkylcarbonyl, alkylcarbonyloxy, alkynyl, carboxy, carboxyalkyl, cyano, cyanoalkyl, formyl, halogen, haloalkyl, hydroxy, hydroxyalkyl, nitro and $R_eR_fN$—, wherein $R_e$ and $R_f$ are defined herein.

The term "cycloalkenylalkyl," as used herein, refers to a cycloalkenyl group, as defined herein, appended to the parent molecular moiety through an alkyl group, as defined herein.

The term "cycloalkenyl-C(O)—," as used herein, refers to a cycloalkenyl group, as defined herein, appended to the parent molecular moiety through a —C(O)— group, as defined herein.

The term "cycloalkenyl-C(O)—NH—," as used herein, refers to a cycloalkenyl-C(O)— group, as defined herein, appended to the parent molecular moiety through a —NH— group, as defined herein.

The term "cycloalkenyl-NH—," as used herein, refers to a cycloalkenyl group, as defined herein, appended to the parent molecular moiety through a —NH— group, as defined herein.

The term "cycloalkenyl-NH—C(O)—," as used herein, refers to a cycloalkenyl-NH— group, as defined herein, appended to the parent molecular moiety through a —C(O)- group, as defined herein.

The term "cycloalkenyl-NH—S(O)$_2$—," as used herein, refers to a cycloalkenyl-NH— group, as defined herein, appended to the parent molecular moiety through a —S(O)$_2$— group, as defined herein.

The term "cycloalkenyloxy," as used herein, refers to a cycloalkenyl group, as defined herein, appended to the parent molecular moiety through an oxy group, as defined herein.

The term "cycloalkenyl-S—," as used herein, refers to a cycloalkenyl group, as defined herein, appended to the parent molecular moiety through an —S— group, as defined herein.

The term "cycloalkenyl-S(O)$_2$—," as used herein, refers to a cycloalkenyl group, as defined herein, appended to the parent molecular moiety through a —S(O)$_2$— group, as defined herein.

The term "cycloalkenyl-S(O)$_2$—NH—," as used herein, refers to a cycloalkenyl-S(O)$_2$— group, as defined herein, appended to the parent molecular moiety through a —NH— group, as defined herein.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl and xanthenyl.

The heterocycles of this invention can be substituted with 0, 1, 2, or 3 substituents independently selected from alkenyl, alkoxy, alkoxyalkyl, alkoxycarbonyl, alkyl, alkylcarbonyl, alkylcarbonyloxy, alkynyl, aryl, aryloxy, arylalkenyl, carboxy, carboxyalkyl, cyano, cyanoalkyl, formyl, halogen, haloalkyl, haloalkoxy, heterocycle, hydroxy, hydroxyalkyl, nitro, $R_eR_fN$—, and $R_eR_fN$—C(O)—, wherein the aryl of aryloxy, the aryl of arylalkenyl, the substituent aryl and the substituent heterocycle can be substituted with 0, 1, 2, or 3 substitutents selected from the group consisting of alkenyl, alkoxy, alkoxycarbonyl, alkyl, alkylcarbonyl, carboxy, carboxyalkyl, cyano, cyanoalkyl, halogen, haloalkyl, haloalkyl, haloalkoxy, hydroxy, hydroxyalkyl, nitro, $R_eR_fN$— and $R_eR_fN$—C(O)—, wherein $R_e$ and $R_f$ are each individually selected from the group consisting of hydrogen, alkyl and alkylcarbonyl.

The term "heterocycle-alkyl," as used herein, refers to a heterocycle, as defined herein, appended to the parent molecular moiety through an alkyl group, as defined herein. Representative examples of heterocycle-alkyl include, but are not limited to, pyridin-3-ylmethyl and 2-pyrimidin-2-ylpropyl.

The term "heterocycle-C(O)—," as used herein, refers to a heterocycle group, as defined herein, appended to the parent molecular moiety through a —C(O)— group, as defined herein.

The term "heterocycle-C(O)—NH—," as used herein, refers to a heterocycle-C(O)— group, as defined herein, appended to the parent molecular moiety through a —NH— group, as defined herein.

The term "heterocycle-NH—," as used herein, refers to a heterocycle group, as defined herein, appended to the parent molecular moiety through a —NH— group, as defined herein.

The term "heterocycle-NH—C(O)—," as used herein, refers to a heterocycle-NH— group, as defined herein, appended to the parent molecular moiety through a —C(O)— group, as defined herein.

The term "heterocycle-NH—S(O)$_2$—," as used herein, refers to a heterocycle-NH— group, as defined herein, appended to the parent molecular moiety through a —S(O)$_2$— group, as defined herein.

The term "heterocycle-O—," as used herein, refers to a heterocycle group, as defined herein, appended to the parent molecular moiety through an —O— group, as defined herein.

The term "heterocycle-S—," as used herein, refers to a heterocycle group, as defined herein, appended to the parent molecular moiety through an —S— group, as defined herein.

The term "heterocycle-S(O)$_2$—," as used herein, refers to a heterocycle group, as defined herein, appended to the parent molecular moiety through a —S(O)$_2$— group, as defined herein.

The term "heterocycle-S(O)$_2$—NH—," as used herein, refers to a heterocycle-S(O)$_2$— group, as defined herein, appended to the parent molecular moiety through an —NH— group, as defined herein.

The term "heterocycle-alkyl-C(O)—," as used herein, refers to a heterocycle-alkyl group, as defined herein, appended to the parent molecular moiety through an —C(O)— group, as defined herein.

The term "heterocycle-alkyl-C(O)—NH—," as used herein, refers to a heterocycle-alkyl-C(O)— group, as defined herein, appended to the parent molecular moiety through a —NH— group, as defined herein.

The term "heterocycle-alkyl-NH—," as used herein, refers to a heterocycle-alkyl group, as defined herein, appended to the parent molecular moiety through a —NH— group, as defined herein.

The term "heterocycle-alkyl-NH—C(O)—," as used herein, refers to a heterocycle-alkyl-NH— group, as defined herein, appended to the parent molecular moiety through a —C(O)— group, as defined herein.

The term "heterocycle-alkyl-NH—S(O)$_2$—," as used herein, refers to a heterocycle-alkyl-NH— group, as defined herein, appended to the parent molecular moiety through a —S(O)$_2$— group, as defined herein.

The term "heterocycle-alkyl-O—," as used herein, refers to a heterocycle-alkyl group, as defined herein, appended to the parent molecular moiety through a —O— group, as defined herein.

The term "heterocycle-alkyl-S—," as used herein, refers to a heterocycle-alkyl group, as defined herein, appended to the parent molecular moiety through a —S— group, as defined herein.

The term "heterocycle-alkyl-S(O)$_2$—," as used herein, refers to a heterocycle-alkyl group, as defined herein, appended to the parent molecular moiety through a —S(O)$_2$— group, as defined herein.

The term "heterocycle-alkyl-S(O)$_2$—NH—," as used herein, refers to a heterocycle-alkyl-S(O)$_2$— group, as defined herein, appended to the parent molecular moiety through a —NH— group, as defined herein.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxybutyl, hydroxypentyl and hydroxyhexyl.

The term "—NR$_b$-alkyl," as used herein, refers to a —NR$_b$— group, as defined herein, appended to the parent molecular moiety through an alkyl group, as defined herein.

The term "oxo," as used herein, refers to a =O moiety.

The term "sulfonyl," as used herein, refers to a —SO$_2$— group.

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isothionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically suitable esters and prodrugs. The term "therapeutically suitable esters and prodrug," refers to those esters and prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to the parent compounds of formula (I-II) for example, by hydrolysis in blood. The term "therapeutically suitable ester," refers to compounds which are rapidly transformed in vivo to the parent compounds of formula (I-II) for example, by hydrolysis in blood. The term "therapeutically suitable ester," refers to alkoxycarbonyl groups appended to the parent molecule on an available carbon atom. More specifically, a "therapeutically suitable ester," may exist on one or more available aryl, cycloalkyl and heterocycle group as defined herein.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein below and resolved by techniques well-known in the art.

Geometric isomers can exist in the present compounds The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents which dissolve or disperse in the injectable media.

Antagonism of the effects of MCH through the MCH receptor by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders caused or exacerbated by MCH are treated or prevented in a patient by administering to the patient, a therapeutically effective amount of compound of the present invention in such an amount and for such time as is necessary to achieve the desired result. The term "therapeutically effective amount," refers to a sufficient amount of a compound to effectively emeliorate disorders mediated by MCH, by antagonizing the effect of MCH through the MCH receptor at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. In general, treatment regimens comprise administration to a patient in need of such treatment from about 10 mg to about 1000 mg of the compounds per day in single or multiple doses.

DETERMINATION OF BIOLOGICAL ACTIVITY

Assay for Release of Intracellular Calcium

Activation of the melanin concentrating hormone receptor (MCHR) by MCH induces the release of $Ca^{++}$ from intracellular stores. This intracellular calcium release is measured using a fluorometric imaging plate reader (FLIPR™, Molecular Devices Corp.) in conjunction with the $Ca^{++}$-sensitive dye Fluo-4. Release of $Ca^{++}$ from intracellular stores causes an increase in fluorescence of the dye that is proportional to $Ca^{++}$ concentration. Briefly, the assays are performed as follows. HEK293 cells expressing the murine MCHR are plated overnight at 50,000 cells/well in 96-well plates. The following day, culture medium is removed and replaced with 100 µl/well of D-PBS (+glucose and sodium pyruvate) containing 2.5 µM Fluo-4AM (Molecular Probes), 0.01% Pluronic F-127 and 2.5 mM probenecid. Cells are loaded with the Fluo-4 dye for at least one hour at room temp. After loading, the cells are washed gently to remove extracellular dye and 100 µl of D-PBS (+glucose and sodium pyruvate) is added to each well. Test compounds are prepared at 40 µM in 4% DMSO. The cell plate is placed in the FLIPR™ and 50 µl/well of test compound is delivered. The calcium signal is followed for 3 minutes to assay for potential agonist activity by the test compounds. Then 50 µl/well of 12 nM human MCH (in D-PBS containing 0.1% BSA) is added and the ligand-induced calcium signal is followed for an additional 3 minutes. Antagonist activity as determined by the test compounds ability to inhibit MCH induced $Ca^{++}$ flux is calculated as % inhibition as described by the following formula:

$$\% \text{ inhibition} = (1-((fTC-fB) \div (fMCH-fB))) \times 100.$$

fTC=MCH-induced fluorescence in the presence of test compound;
FMCH=MCH-induced fluorescence in the absence of test compound;
fB=Baseline fluorescence.
MCH (3 nM) usually elicits a response of 30,000–40,000 relative fluorescence units (RFU) with a baseline of ~1000 RFU. Fluo-4 fluorescence is measured at 488 nm, with an exposure of 0.40 sec. and F-stop=2.0 and the laser set at 0.40–0.60 W constant light output.

The compounds of the present invention inhibit MCH induced fluorescence at a dose of 10 µM. In a preferred range, compounds of the present invention inhibit MCH induced fluorescence in a range of 75–100% inhibition of MCH at a dose of 10 µM. In a more preferred range, compounds of the present invention inhibit MCH induced fluorescence in a range of 90–100% inhibition of MCH at a dose of 10 µM.

Within the disclosures of another patent application (Aventis WO-2003015769), compounds have been reported to effectively block the action of MCH at MCHr1 as determined by the reduction in MCH-initiated $Ca^{2+}$ flux in cellular assays. In addition, compounds of this publication demonstrate an acute anorectic response in vivo measured by the compounds effect on reducing the volume of sweetened milk consumed after oral administration of a single dose of the compound.

However, for sustained in vivo efficacy, there is not only a requirement that the compounds demonstrate potent inhibition of MCH-mediated effects by blockade of MCHr1, but also that they demonstrate a desirable pharmacokinetic profile after oral administration. Specifically, since the highest level of expression of the MCHr1 receptor is in the lateral hypothalamus region of the brain, it is expected that to achieve efficacy in a chronic model, the compounds need to demonstrate high and/or prolonged effective concentrations in the brain. It is expected that an effective concentration would require drug levels in the brain that exceed the $IC_{50}$ for blockade of MCH-initiated $Ca^{2+}$ flux measured in cellular assays.

The compounds of the present invention demonstrate high intrinsic activity as MCHr1 antagonists, and favorable pharmacokinetic profiles resulting in high and/or prolonged effective concentrations in the brain after oral dosing as shown in Table 1. Furthermore, a direct comparison of the concentration of compound entering the brain between the compounds of the present invention and the compounds disclosed in the Aventis publication show that while high concentrations of compounds of the present invention are attained following oral administration, the Aventis compounds do not. In addition, the administration of compounds of the present invention resulted in a >5% weight loss when administered for 2 weeks with twice a day, oral dosing in mice. Compounds of the present invention also demonstrate improved potency for MCHr1 antagonism and improved pharmacokinetic properties when compared to compounds (Example 4) described in patent publication WO-2003015769. The unexpected properties demonstrated by the compounds of the present invention results in examples that deliver efficacy in a chronic model of weight loss in diet-induced obese mice, whereas the compounds described in WO-2003015769 (Example 4) are not effective in this model.

TABLE 1

$Ca^{2+}$ flux inhibition, Pharmacokinetic drug levels in whole brain after 10 mpk oral dose, and Efficacy (% weight loss in DIO mice after two weeks of dosing @ 100 mpk BID).

| Compound | $Ca^{2+}$ flux Inh.[a] $IC_{50}$ | Brain Conc.[b] (10 mpk PO) | | DIO Mice[c] (100 mpk BID, PO) % weight loss @ 14 days[d] |
|---|---|---|---|---|
| | | $C_{max}$ | AUC | |
| Aventis Ex. 4 | 298 nM | 0 ng/g | 0 ng · hr/g | <5% |
| Example 24 | 104 nM | 260 ng/g | 1428 ng · hr/g | 15% |

[a]Inhibition of MCH-induced fluorescence in IMR-32 neuroblastoma cells. Details of this assay are described in the "Determination of Biological Activity".
[b]Compounds are dosed in DIO-mice orally @ 10 mpk in a vehicle containing 1% Tween-80 and water. Whole brains are harvested at 0.5, 1, 2, 4, 6, 8, 12, and 24 h after the dose, and drug-concentrations are determined by mass spectroscopy analysis in comparison with a standard curve.
[c]Generation of diet-induced obese (DIO) mice: Male C57Bl/6J mice are placed on a 60% kcal lard diet for 3–4 months, during which time they become obese (45 g vs. 30 g for lean controls on normal chow).
[d]Compounds are orally dosed twice a day @ 100 mpk in a vehicle containing 1% Tween-80 and water. The animals are weighed after 14 days of dosing to determine % weight loss relative to control animals that received only the vehicle.

As antagonists of MCH action upon the MCH receptor, therefore, the compounds of the present invention are useful in treating disorders that are mediated by MCH through the MCH receptor. Disorders that are mediated by MCH through the MCH receptor are obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Therefore the compounds of the present invention are useful in treating obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders.

Therapeutic agents acting through MCH receptor may also be useful in treatment of abnormalities in reproduction and sexual behavior (Murray, J. F.; Mercer J. G., Adan R. A., Datta J. J., Aldairy C, Moar K M, Baker B I, Stock M J, Wilson, C. A.; The effect of leptin on luteinizing hormone release is exerted in the zona incerta and mediated by melanin-concentrating hormone. J Neuroendocrinol 12:1133–1139, 2000; Gonzalez, M. I., Baker, B. I., Wilson, C. A.; Stimulatory effect of melanin-concentrating hormone on luteinising hormone release. Neuroendocrinology 66:254–262, 1997.; Murray, J. F., Adan, R. A., Walker, R., Baker, B. I., Thody, A. J., Nijenhuis, W. A., Yukitake, J., Wilson, C. A.; Melanin-concentrating hormone, melanocortin receptors and regulation of luteinizing hormone release. J Neuroendocrinol 12:217–223, 2000.; Nahon, J. L.; The melanin-concentrating hormone: from the peptide to the gene. Crit Rev Neurobiol 8:221–262, 1994.)

Therapeutic agents acting through MCH receptor may also be useful in treatment of thyroid hormone secretion (Kennedy, A. R., Todd, J. F., Stanley, S. A., Abbott, C. R., Small, C. J., Ghatei, M. A., Bloom, S. R.; Melanin-concentrating hormone (MCH) suppresses thyroid stimulating hormone (TSH) release, in vivo and in vitro, via the hypothalamus and the pituitary. Endocrinology 142:3265–3268. 2001).

Therapeutic agents acting through MCH receptor may also be useful in treatment of diuresis and water/electrolyte homeostasis (Hervieu, G., Volant, K., Grishina, O., Descroix-Vagne, M., Nahon, J. L.; Similarities in cellular expression and functions of melanin-concentrating hormone and atrial natriuretic factor in the rat digestive tract. Endocrinology 137:561–571, 1996.; and Parkes, D. G.; Diuretic and natriuretic actions of melanin concentrating hormone in conscious sheep. J Neuroendocrinol 8:57–63, 1996).

Therapeutic agents acting through MCH receptor may also be useful in treatment of sensory processing (Miller, C. L., Hruby, V. J., Matsunaga, T. O., Bickford, P. C.; Alpha-MSH and MCH are functional antagonists in a CNS auditory gating paradigm. Peptides 14:431–440, 1993.; Kokkotou, E. G., Tritos, N. A., Mastaitis, J. W., Slieker, L., Maratos-Flier, E.; Melanin-concentrating hormone receptor is a target of leptin action in the mouse brain. Endocrinology 142:680–686, 2001).

Therapeutic agents acting through MCH receptor may also be useful in treatment of memory (Monzon, M. E., De Barioglio, S. R.; Response to novelty after i.c.v. injection of melanin-concentrating hormone (MCH) in rats. Physiol Behav 67:813–817, 1999).

Therapeutic agents acting through MCH receptor may also be useful in treatment of sleeping and arousal (Bittencourt, J. C., Presse, F., Arias, C., Peto, C., Vaughan, J., Nahon, J. L., Vale, W., Sawchenko, P. E.; The melanin-concentrating hormone system of the rat brain: an immuno- and hybridization histochemical characterization. J Comp Neurol 319:218–245, 1992.; Nahon, J. L.; The melanin-concentrating hormone: from the peptide to the gene. Crit Rev Neurobiol 8:221–262, 1994).

Therapeutic agents acting through MCH receptor may also be useful in treatment of anxiety and depression (Monzon, M. E., Varas, M. M., De Barioglio, S. R.; Anxiogenesis induced by nitric oxide synthase inhibition and anxiolytic effect of melanin-concentrating hormone (MCH) in rat brain. Peptides 22:1043–1047, 2001.; Monzon, M. E., De Barioglio, S. R.; Response to novelty after i.c.v. injection of melanin-concentrating hormone (MCH) in rats. Physiol Behav 67:813–817, 1999; Borowsky, B., Durkin, M. M., Ogozalek, K., Marzabadi, M. R., DeLeon, J., Lagu, B., Heurich, R., Lichtblau, H., Shaposhnik, Z., Daniewska, I., Blackburn, T. P., Branchek, T. A., Gerald, C., Vaysse, P. J., Forray, C.; Antidepressant, anxiolytic and anorectic effects of a melanin-concentrating hormone-1 receptor antagonist. Nat. Med. 8:825–830, 2002).

Therapeutic agents acting through MCH receptor may also be useful in treatment of seizure (Knigge, K. M., Wagner, J. E;. Melanin-concentrating hormone (MCH) involvement in pentylenetetrazole (PTZ)-induced seizure in rat and guinea pig. Peptides 18:1095–1097, 1997) and in treatment of neurodegeneration or psychiatric disorders (Nahon, J. L.; The melanin-concentrating hormone: from the peptide to the gene. Crit Rev Neurobiol 8:221–262, 1994).

Synthetic Methods

Abbreviations which have been used in the descriptions of the scheme and the examples that follow are: dba for dibenzylideneacetone; DMSO for dimethylsulfoxide; NMP for N-methylpyrrolidinone; DMF for N,N-dimethylformamide; DCC for 1,3-dicyclohexylcarbodiimide, DIC for 2-dimethylaminoisopropyl chloride hydrochloride, HATU for O-(7-azabenzotriazol-1-yl)-N,N,N',N'-tetramethyluronium hexafluorophosphate, HBTU for O-benzotriazole-1-yl)-N,N,N',N'-tetramethyluronium hexafluorophosphate, MTBE for methyl tert butyl ether, TFA for trifluoroacetic acid; THF for tetrahydrofuran; EDCI for 1-(3-dimethylaminopropyl)-3-ethylcarbodiimide hydrochloride; HOAt for 1-hydroxy-7-azabenzotriazole, and HOBt for 1-hydroxybenzotriazole hydrate.

The compounds and processes of the present invention will be better understood in connection with the following synthetic schemes which together illustrate the methods by which the compounds of the invention may be prepared. The groups $R_1$, $R_2$, $R_3$, $R_4$, $R_5$, $R_6$, $R_7$, $R_8$, $R_9$, $R_{10}$ are as defined above unless otherwise noted below.

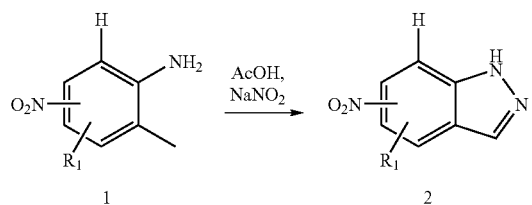

As shown in Scheme 1, compounds of formula 1 (wherein $R_1$ is hydrogen, halogen, alkyl or alkoxy) can be treated with acetic acid and $NaNO_2$ at room temperature to provide compounds of formula 2.

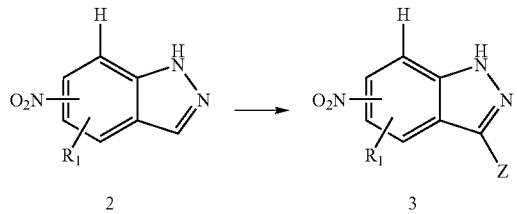

As shown in Scheme 2, compounds of formula 2 can be treated with sodium hydroxide and reagents such as but not limited to sodium hypochlorite or bromine to provide compounds of formula 3, where Z is chlorine or bromine respectively.

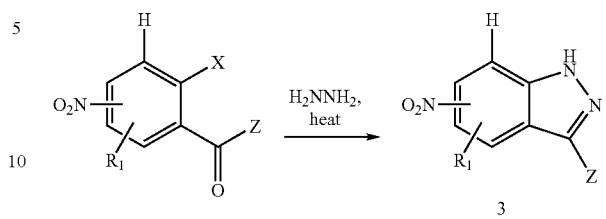

As shown in Scheme 3, nitro benzene compounds (wherein X is halogen, and $R_1$ is alkoxy or alkyl) can be treated with hydrazine hydrate under heated conditions to provide compounds of formula 3 where Z is alkyl or hydrogen.

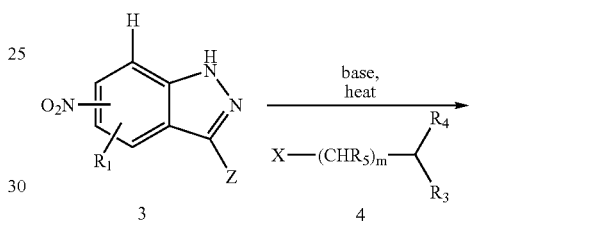

As shown in Scheme 4, compounds of formula 2 or 3 can be treated under heated conditions with base and compounds of formula 4 (wherein $R_3$, $R_4$ and m are described herein and X is halogen, methanesulfonate, toluenesulfonate or triflourosulfonate), to provide compounds of formula 5. Typical bases include but are not limited to cesium carbonate and potassium carbonate, and solvents include but are not limited to N,N-dimethylformamide, N,N-dimethylacetamide and tetrahydrofuran.

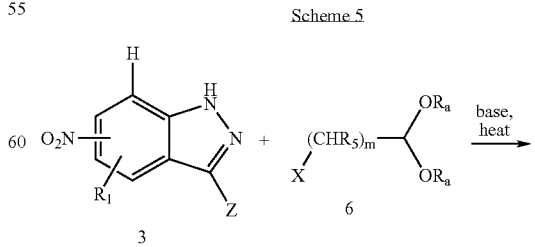

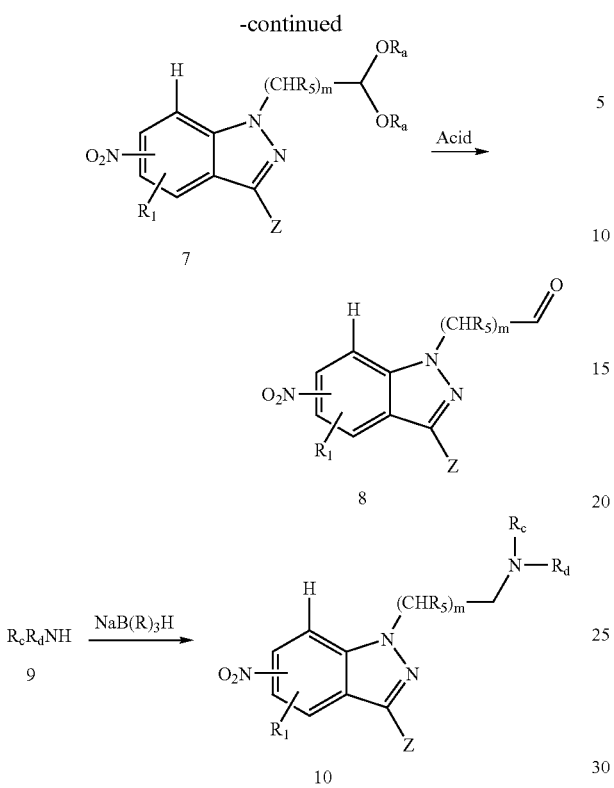

Alternatively, compounds of formula 3 can be treated under heated conditions with compounds of formula 6 (wherein $R_a$ is methyl or ethyl; X is halogen, methanesulfonate, toluenesulfonate or triflourosulfonate and m is defined herein) and base to provide compounds of formula 7. Typical bases include but are not limited to cesium carbonate and potassium carbonate, and solvents include but are not limited to N,N-dimethylformamide, N,N-dimethylacetamide and tetrahydrofuran. Compounds of formula 7 can be treated under heated conditions with acid to afford compounds of formula 8. Typical acids include but are not limited to dilute hydrochloric acid or toluenesulfonic acid and the like, in solvents such as aqueous tetrahydrofuran or aqueous methanol. Compounds of formula 8 can then be treated with primary or secondary amines of formula 9 and a reducing agent to afford compounds of formula 10. Typical reducing agents include but are not limited to sodium triacetoxyborohydride, sodium cyanoborohydride, and the like; and typical solvents include but are not limited to tetrahydrofuran, isopropyl acetate, methanol, dichloroethane and mixtures thereof.

As shown in Scheme 6, compounds of formula 5 can be treated according to conditions commonly known to those skilled in the art that will reduce a nitro group to an amine group such as but not limited to ammonium chloride and iron, hydrogen and Pd/C, and the like to afford compounds of formula 11. Solvents include but are not limited to ethanol, methanol, ethyl acetate, $H_2O$ and mixtures thereof.

As shown in Scheme 7, amines of formula 11 can be treated with carboxylic acids of formula 12 under conditions know to those skilled in the art that will form amide bonds to provide compounds of formula 13 which are representative of compounds of the present invention. Typical reaction conditions include stirring a compound of formula 11 and a compound of formula 12 with a coupling reagent such as but not limited to EDCI, DCC, DIC, HATU, HBTU, an auxiliary nucleophile such as but not limited to HOBt and HOAt and a base such as but not limited to diisopropylethylamine, triethylamine, N-methylmorpholine in solvents such as but not limited to N,N-dimethylformamide and methylene chloride.

Scheme 8

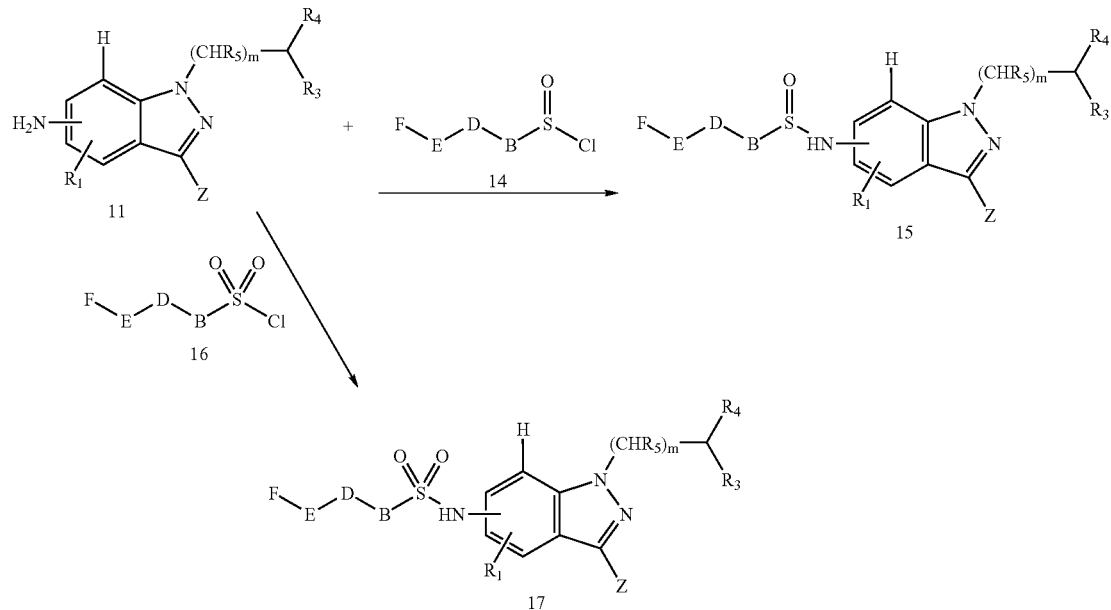

As shown in Scheme 8, compound of formula 11 may also be treated with compounds of formula 14 and a base such as triethylamine in solvents such as tetrahydrofuran to provide compounds of formula 15 which are representative of compounds of the present invention. Similarly, compounds of formula 11 may be treated with compounds of formula 16 and a base such as triethylamine in solvents such as tetrahydrofuran to provide compounds of formula 17 which are representative of compounds of the present invention.

Scheme 9

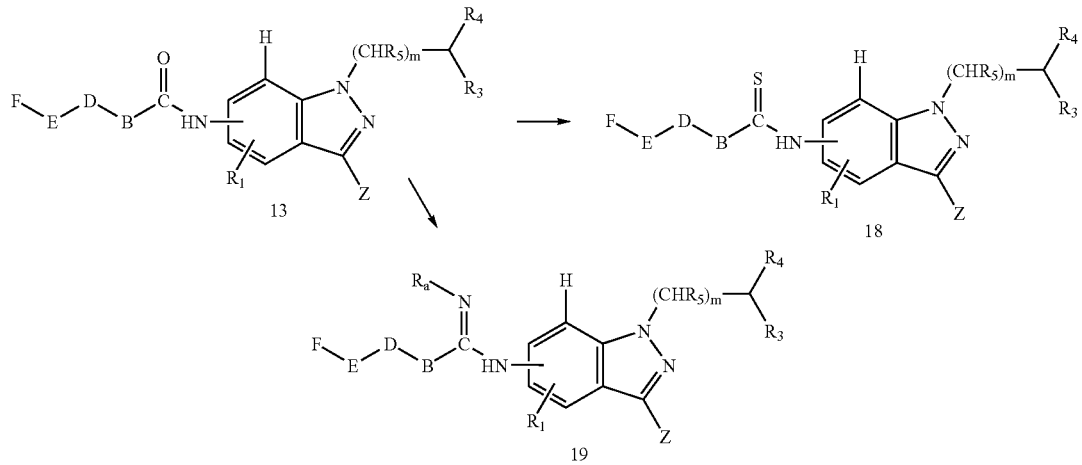

In addition, compounds of formula 13 may be further converted into compounds of formula 18 and 19 as described in Scheme 9. The treatment of compound of formula 13 with Lawessons reagent in solvents such as tetrahydrofuran or toluene will provide compounds of formula 18 which are representative of compounds of the present invention. Alternatively, the treatment of compounds of formula 13 with amines of formula $R_a$—$NH_2$ in a solvent such as toluene under refluxing conditions with a Dean-Stark trap will provide compounds of formula 19 which are representative of compounds of the present invention.

Scheme 10

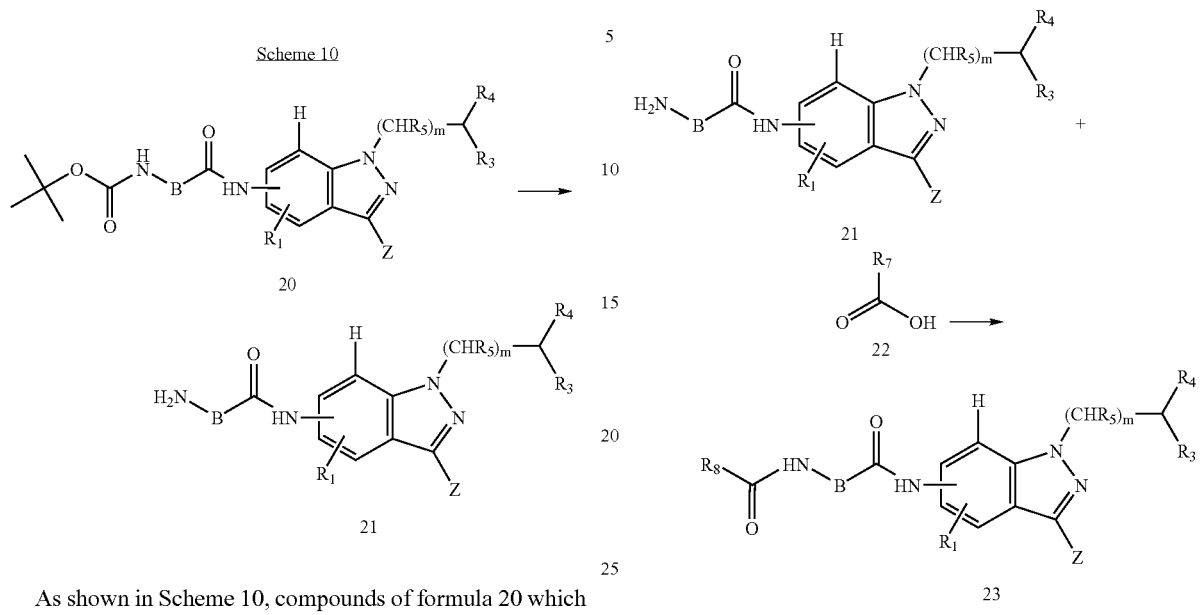

As shown in Scheme 10, compounds of formula 20 which are representative of the compounds of the present invention, where D is a bond and E is —NH— can be prepared from the above mentioned schemes. Compounds of formula 20 can be treated according to conditions known to deprotect amine protecting groups such as hydrochloric acid in acetic acid or trifluoroacetic acid methylene chloride to provide compounds of formula 21.

Scheme 11

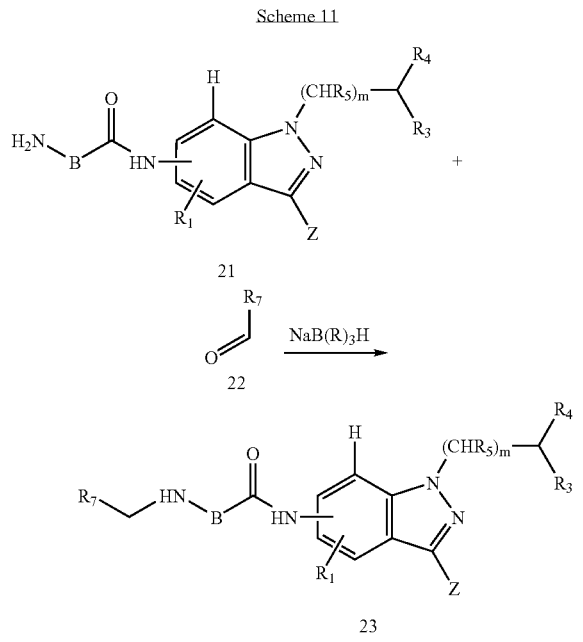

As shown in Scheme 11, compounds of formula 21 can be treated with compounds of formula 22 in the presence of a reducing agent such as but not limited to sodium triacetoxy-borohydride, sodium cyanoborohydride to provide compounds of formula 23 which are representative of compounds of the present invention.

Alternatively, compounds of formula 21 can be treated with carboxylic acids of formula 22 under conditions for amide bond formation to afford compounds of formula 23 which are representative of compounds of the present invention. Typical coupling conditions include stirring compounds of formula 21 and compounds of formula 22 in the presence of EDCI, DCC, DIC, HATU, HBTU and an auxiliary nucleophile such as but not limited to HOBt and HOAt and a base such as diisopropylethylamine, triethylamine, N-methylmorpholine. Typical solvents include but are not limited to N,N-dimethylformamide and methylene chloride.

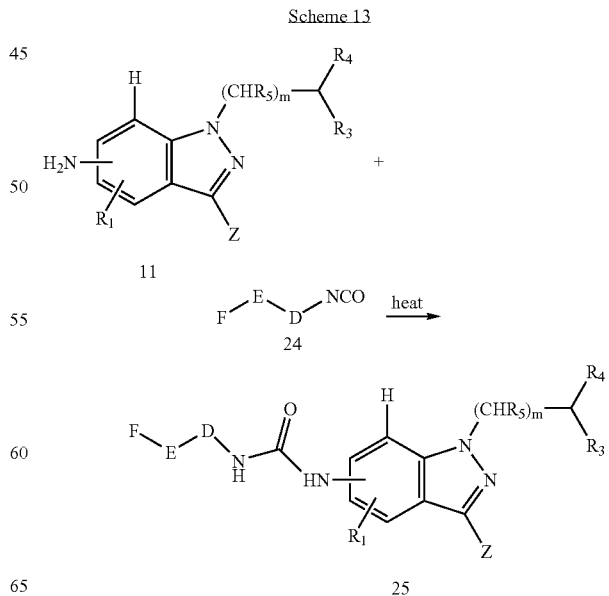

As shown in Scheme 13, compounds of formula 11 can be treated with isocyanates of formula 24 at elevated temperatures in solvents such as but not limited to tetrahydrofuran and dioxane to provide compounds of formula 25, which are representative of compounds of the present invention.

Scheme 14

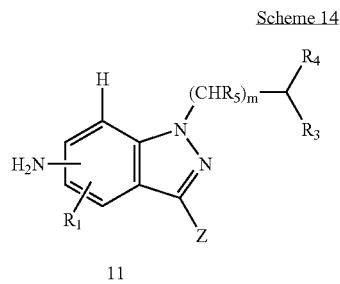

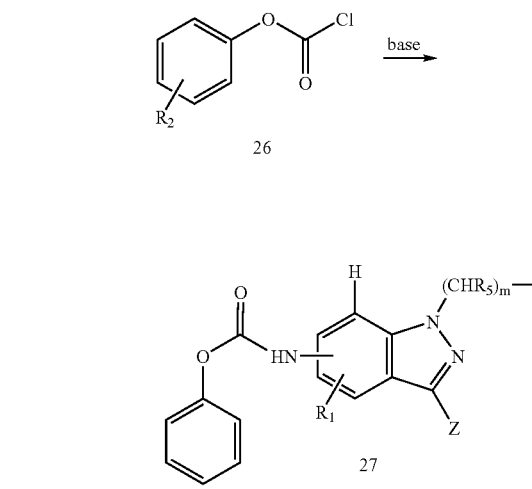

Alternatively, compounds of formula 11 can be treated with phenyl chloroformates of formula 26 in the presence of a base such as but not limited to triethylamine and potassium carbonate in solvents such as but not limited to dichloroethane, methylene chloride and chloroform to provide carbamates of formula 27.

Scheme 15

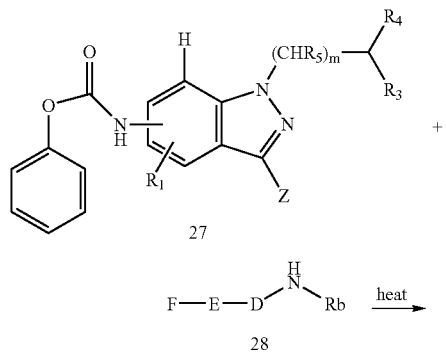

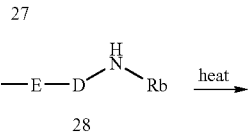

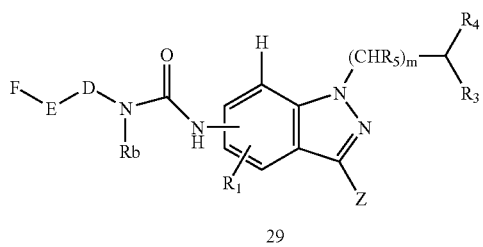

As shown in Scheme 15, carbamates of formula 27 can be treated with primary or secondary amines of formula 28 in the presence of a base such as triethylamine or potassium carbonate in solvents such as N-methylpyrolidinone or tetrahydrofurane at elevated temperatures to afford compounds of formula 29, which are representative of compounds of the present invention.

Scheme 16

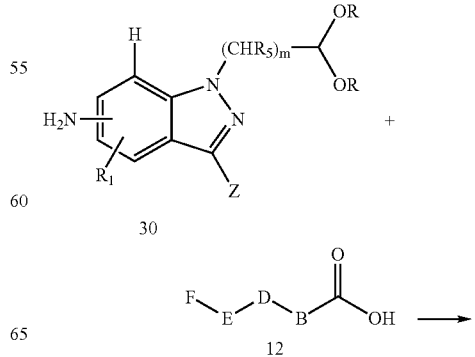

As shown in Scheme 16, the reduction of the nitro functional group of compounds of formula 7 can be achieved utilizing the same conditions described in Scheme 6 to provide compounds of formula 30.

Scheme 17

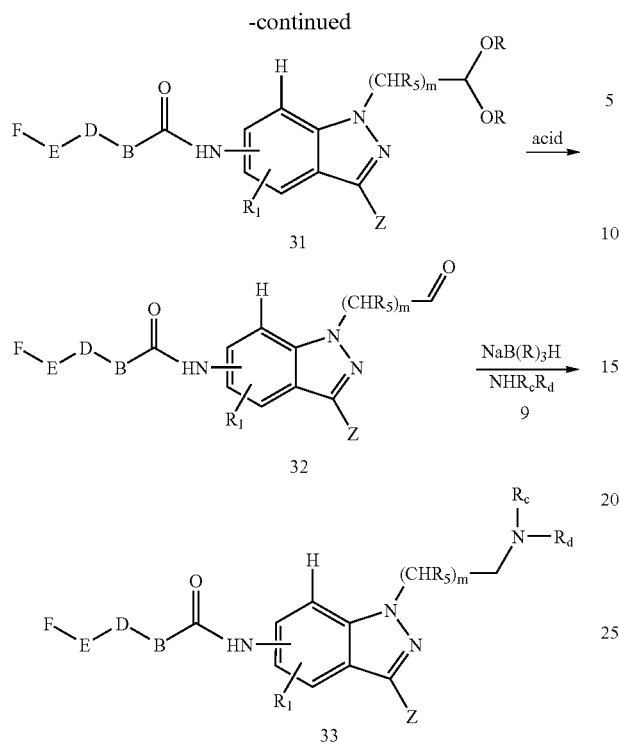

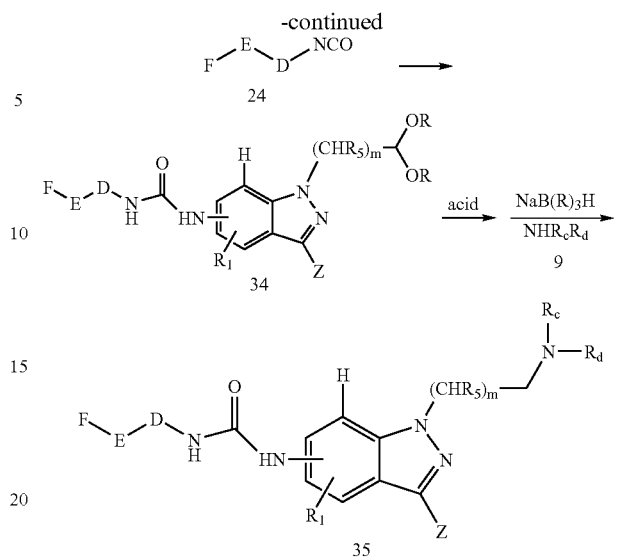

As shown in Scheme 17, compounds of formula 30 can be treated with carboxylic acids of formula 12 under conditions for amide bond formation to afford compounds of formula 31. Typical reaction conditions include stirring a compound of formula 30 and a compound of formula 12 with a coupling reagent such as but not limited to EDCI, DCC, DIC, HATU, HBTU, an auxiliary nucleophile such as but not limited to HOBt and HOAt and a base such as but not limited to diisopropylethylamine, triethylamine, N-methylmorpholine in solvents such as but not limited to N,N-dimethylformamide and methylene chloride. Compounds of formula 31 when treated with an acid such as but not limited to hydrochloric acid and toluenesulfonic acid under heated conditions will provide compounds of formula 32. Compounds of formula 32 can then be treated with primary or secondary amines of formula 9 and a reducing agent such as but not limited to sodium triacetoxyborohydride, sodium cyanoborohydride in solvents such as tetrahydrofuran, IPA, MeOH, DCE and mixtures thereof to provide compounds of formula 33 which are representative of the compounds of the present invention.

Scheme 18

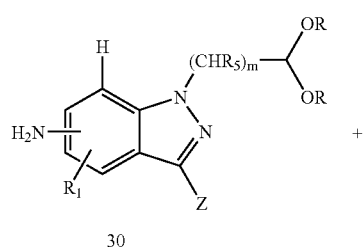

As shown in Scheme 18, compounds of formula 30 can be treated with isocyanates of formula 24 at elevated temperatures to afford compounds of formula 34. Solvents include but are not limited to tetrahydrofuran, dioxane, and ether, and the like. Compounds of formula 34 can be treated with acid and with compounds of formula 9 under reductive amination conditions as outlined in Scheme 17 to provide compounds of formula 35 which are representative of the compounds of the present invention.

Scheme 19

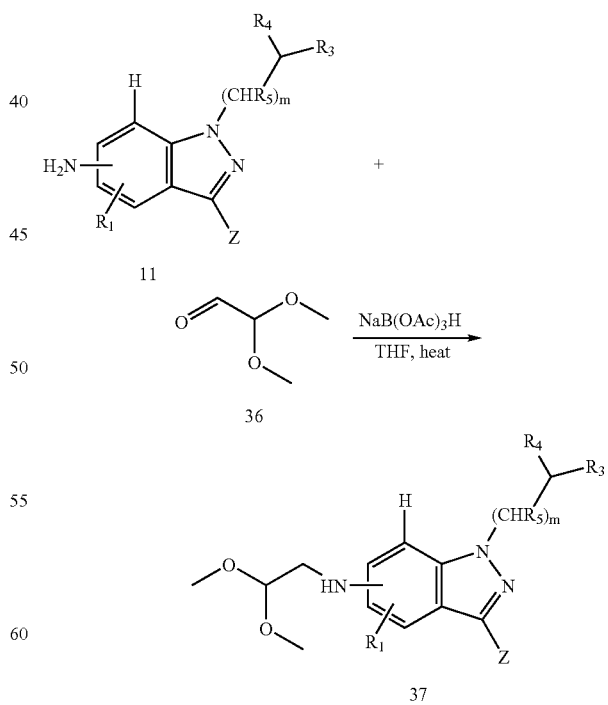

As shown in Scheme 19, compounds of formula 11 can be treated with compounds of formula 36 and a reducing agent under heated conditions to provide compounds of formula 37. Typical reducing agents include but are not limited to sodium triacetoxyborohydride, sodium cyanoborohydride, and the like; and typical solvents include but are not limited to THF, IPA, MeOH, DCE and mixtures thereof.

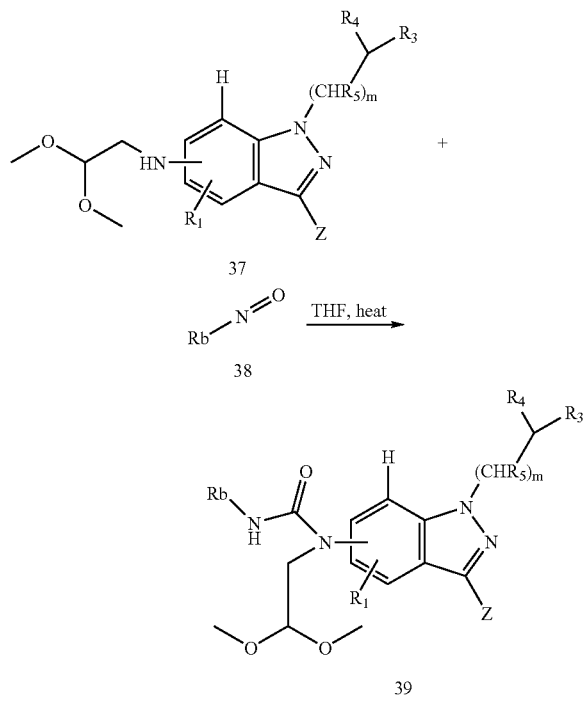

As shown in Scheme 20, compounds of formula 37 can be treated with isocyanates of formula 38 in solvents such as but not limited to THF, dioxane and ether at elevated temperatures to provide compounds of formula 39.

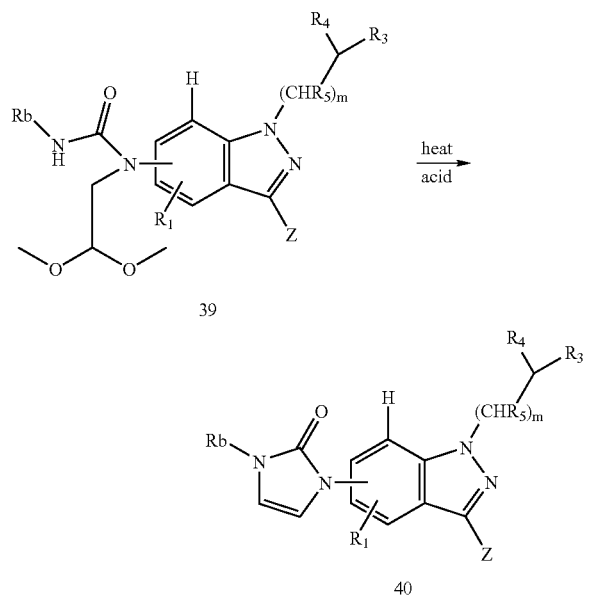

As shown in Scheme 21, compounds of formula 39 can be heated with catalytic amounts of acid to provide compounds of formula 40. Solvents include but are not limited to THF, dioxane and ether, and acids include but are not limited to sulfuric acid and toluenesulfonic acid.

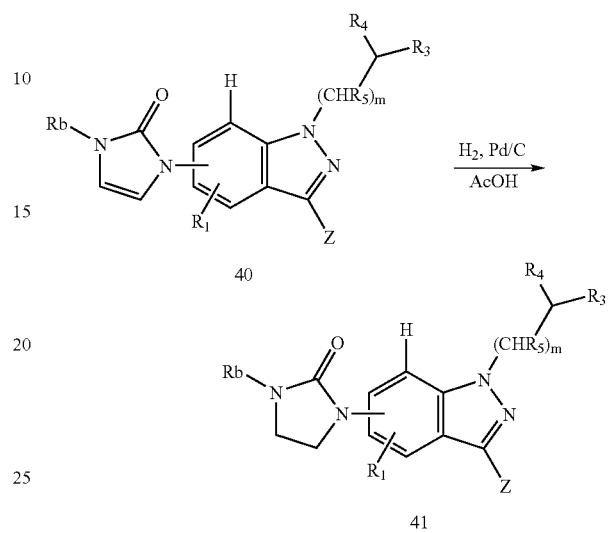

As shown in Scheme 22, compounds of formula 40 can be treated to hydrogen gas at a pressure of 30–90 psi and in the presence of a catalyst such as 5–10% palladium on carbon to provide compounds of formula 41. Typical reducing catalysts include but are not limited to palladium on carbon and platinum on carbon. Typical solvents include but are not limited to AcOH, EtOH, EtOAc, MeOH. Reactions are performed at refluxing temperature and are typically complete within 6 hours.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.01 (developed by Advanced Chemistry Development, Inc., Toronto, ON, Canada) or were given names consistent with ACD nomenclature.

EXPERIMENTALS

EXAMPLE 1

N-(2-oxo-2-{[1-(2-pyrrolidin-1-ylethyl)-1H-indazol-4-yl]amino}ethyl)-4-phenoxybenzamide

EXAMPLE 1A 4-nitro-1H-indazole

A mixture of 2-methyl-3-nitro-aniline (5.00 g, 32.9 mmol) and a solution of sodium nitrite (2.27 g, 32.9 mmol) in water (7.5 mL) in glacial acetic acid (750 mL) was was stirred for 15 minutes and allowed to stand at room temperature for 3 days. The mixture was concentrated under reduced pressure leaving a pale yellow solid which was dissolved in ethyl acetate (250 mL) and filtered through a plug of silica gel, rinsing with ethyl acetate. The combined ethyl acetate was concentrated under reduced pressure to provide a pale yellow solid. $^1$H NMR (300 MHz, DMSO-d$_6$) δ ppm 7.65 (m, 1H), 8.10 (m, 1H), 8.16 (m, 1H), 8.54 (s, 1H), 13.9 (s, 1H); MS (DCI/NH$_3$) m/z 164 [M+H]$^+$.

EXAMPLE 1B 4-nitro-1-(2-pyrrolidin-1-yl-ethyl)-1H-indazole

4-Nitroindazole (3.00 g, 18.4 mmol) and potassium carbonate (7.50 g, 54.4 mmol) in 60 mL of DMF was stirred for 30 minutes after which 1-(2-chloro-ethyl)-pyrrolidine hydrochloride (4.80 g 28.4 mmol) was added. The mixture was heated to 60° C. for 6 hours, cooled to room temperature and filtered through a plug of silica gel. The silica gel was rinsed with triethylamine/ethyl acetate (1/4), the combined filtrate was concentrated under reduced pressure and the residue purified by flash chromatography (silica gel, triethylamine/ethyl acetate 1/30). $^1$H NMR (300 MHz, DMSO-d$_6$) δ ppm 1.60 (m, 4H), 2.45 (m, 4H), 2.92 (t, 2H, J=6.45), 4.65 (t, 2H, J=6.45), 7.65 (m, 1H), 8.10 (m, 1H), 8.30 (m, 1H), 8.52 (s, 1H); MS (DCI/NH$_3$) m/z 261 [M+H]$^+$.

EXAMPLE 1C 1-(2-pyrrolidin-1-yl-ethyl)-1H-indazol-4-ylamine

4-Nitro-1-(2-pyrrolidin-1-yl-ethyl)-1H-indazole (1.90 g, 7.30 mmol), iron powder (4.10 g, 73.4 mmol), and ammonium chloride (0.200 g, 3.65 mmol) were suspended in a 4:1 solution of ethanol/H$_2$O. The mixture was heated to reflux for 3 hours, cooled to room temperature and concentrated under reduced pressure. The residue was taken up and stirred in triethylamine/ethyl acetate (1/4, 30 mL) for 15 minutes and filtered through a plug of silica gel. The silica gel was rinsing with triethylamine/ethyl acetate (1/4) and combined filtrate concentrated under reduced pressure to provide the title compound. $^1$H NMR (300 MHz, DMSO-d$_6$) δ ppm 1.62 (m, 4H), 2.44 (m, 4H), 2.81 (t, 2H, J=6.78), 4.34 (t, 2H, J=6.78), 5.73 (s, 2H), 6.13 (m, 1H), 6.66 (m, 1H), 7.01 (m, 1H), 8.05 (s, 1H); MS (DCI/NH$_3$) m/z 231 [M+H]$^+$.

EXAMPLE 1D

{[1-(2-pyrrolidin-1-yl-ethyl)-1H-indazol-4-ylcarbamoyl]-methyl}-carbamic acid tert-butyl ester 1-(2-Pyrrolidin-1-yl-ethyl)-1H-indazol-4-ylamine (1.00 g, 4.34 mmol), tert-butoxycarbonylamino-acetic acid (0.836 g, 4.77 mmol), ethyldimethylpropylcarbodiimide hydrochloride (1.00 g, 5.24 mmol), N-hydroxybenzotriazole (0.707 g, 5.24 mmol) and N-methyl morpholine (1.10 g, 10.9 mmol) were dissolved in 30 mL of DMF, and stirred at room temperature for 6 hours. The mixture was concentrated under reduced pressure and the residue purified by flash chromatography to provide the title compound. $^1$H NMR (300 MHz, DMSO-d$_6$) δ ppm 1.41 (s, 9H), 1.62 (m, 4H), 2.44 (m, 4H), 2.86 (t, 2H, J=6.78), 3.86 (d, 2H, J=6.11), 4.47 (t, 2H, J=6.78), 7.08–7.65 (m, 3H), 8.24 (s, 1H), 9.97 (s, 1H); MS (DCI/NH$_3$) m/z 388 [M+H]$^+$.

EXAMPLE 1E 2-amino-N-[1-(2-pyrrolidin-1-yl-ethyl)-1H-indazol-4-yl]-acetamide {[1-(2-Pyrrolidin-1-yl-ethyl)-1H-indazol-4-ylcarbamoyl]-methyl}-carbamic acid tert-butyl ester (1.00 g, 2.58 mmol) and a solution of HCl (5 mL, 4M in dioxane) was in dichloromethane (30 mL) was stirred for 3 hours. The mixture was filtered and rinsed with dichloromethane to provide the title compound as the bis-HCl salt. $^1$H NMR (300 MHz, DMSO-d$_6$) δ ppm 1.78–2.00 (m, 4H), 2.88–3.00 (m, 2H), 3.45 (m, 2H), 3.67 (m, 2H), 4.09 (m, 2H), 4.85 (t, 2H, J=6.45), 7.40–7.77 (m, 3H), 8.30 (s, 3H), 8.59 (s, 1H), 10.9 (s, 1H), 11.11 (s, 1H); MS (DCI/NH$_3$) m/z 288 [M+H]$^+$.

EXAMPLE 1

N-(2-oxo-2-{[1-(2-pyrrolidin-1-ylethyl)-1H-indazol-4-yl]amino}ethyl)-4-phenoxybenzamide A mixture of 2-amino-N-[1-(2-pyrrolidin-1-yl-ethyl)-1H-indazol-4-yl]-acetamide (HCl salt, 0.0600 g, 0.186 mmol), (4-benzyloxy-phenyl)-acetic acid (0.0470 g, 0.190 mmol), ethyldimethylpropylcarbodiimide hydrochloride (0.0430 g, 0.225 mmol), N-hydroxybenzotriazole (0.0300 g, 0.222 mmol), N-methyl morpholine (0.0460 g, 0.455 mmol) in 2 mL of DMF was stirred for 6 hours. The mixture was concentrated under reduced pressure, the residue dissolved in 1.5 mL of a 1:1 mixture of DMSO/MeOH and purified by preparative reverse-phase HPLC. $^1$H NMR (300 MHz, DMSO-d$_6$) δ ppm 1.62 (m, 4H), 2.44 (m, 4H), 2.87 (t, 2H, J=6.78), 2.95 (s, 2H), 4.20 (d, 2H, J=5.76), 4.48 (t, 2H, J=6.78), 6.99–7.47 (m, 9H), 7.65 (m, 1H), 7.96 (m, 2H), 8.27 (m, 1H), 8.83 (m, 1H), 10.13 (s, 1H); MS (DCI/NH$_3$) m/z 484 [M+H]$^+$.

EXAMPLE 2

2-[(4-phenoxybenzyl)amino]-N-[1-(2-pyrrolidin-1-ylethyl)-1H-indazol-4-yl]acetamide A mixture of Example 1E (70.0 mg, 0.217 mmol), 4-phenoxy-benzaldehyde (65.0 mg, 0.328 mmol), NaCNBH$_3$ (41.0 mg, 0.652 mmol) in 4 mL of THF was shaken for 12 hours. The mixture was concentrated under reduced pressure and the residue was dissolved in 1.5 mL of a 1:1 mixture of dimethyl sulfoxide/MeOH and purified by preparative reverse-phase HPLC. $^1$H NMR (300 MHz, DMSO-d$_6$) δ ppm 1.61 (m, 4H), 2.44 (m, 4H), 2.86 (t, 2H, J=6.70), 3.41 (s, 2H), 3.78 (s, 2H), 4.47 (t, 2H, J=6.70), 6.96 (m, 4H), 7.11 (m, 1H), 7.29–7.41 (m, 6H), 7.67 (m, 1H), 8.14 (s, 1H), 9.94 (s, 1H); MS (DCI/NH$_3$) m/z 470 [M+H]$^+$.

EXAMPLE 3

2-[4-(benzyloxy)phenyl]-N-[1-(2-pyrrolidin-1-yl-ethyl)-1H-indazol-4-yl]acetamide A mixture of Example 1C (42.0 mg, 0.183 mmol), (4-benzyloxy-phenyl)-acetic acid (47.0 mg, 0.194 mmol), ethyldimethylpropylcarbodiimide hydrochloride (43.0 mg, 0.225 mmol), N-hydroxybenzotriazole (30.0 mg, 0.222 mmol), N-methyl morpholine (46.0 mg, 0.455 mmol) in 2 mL of DMF was shaken for 6 hour. The mixture was concentrated under reduced pressure and the residue dissolved in 1.5 mL of a 1:1 mixture of dimethyl sulfoxide/

MeOH and purified by preparative reverse-phase HPLC. $^1$H NMR (300 MHz, DMSO-d$_6$) δ ppm 1.66 (m, 4H), 2.49 (m, 4H), 2.91 (t, 2H, J=6.60), 3.76 (s, 2H), 4.42 (t, 2H, J=6.60), 5.14 (s, 2H), 7.03 (m, 2H), 7.31–7.50 (m, 9H), 7.68 (m, 1H), 8.30 (s, 1H), 10.16 (s, 1H); MS (DCI/NH$_3$) m/z 455 [M+H]$^+$.

EXAMPLE 4

2-(3-phenoxyphenyl)-N-[1-(2-pyrrolidin-1-ylethyl)-1H-indazol-4-yl]acetamide 1-(2-pyrrolidin-1-yl-ethyl)-1H-indazol-4-ylamine and (3-phenoxy-phenyl)-acetic acid were processed as described in Example 3 to provide the title compound. MS (DCI/NH$_3$) MS m/z 441 (M+H)$^+$; $^1$H NMR (500 MHz, DMSO-d$_6$) δ ppm 1.83 (m, 2 H), 2.01 (m, 2 H), 3.04 (m, 2 H), 3.52 (m, 2 H), 3.71 (q, J=5.72 Hz, 2 H), 3.79 (s, 2 H), 4.76 (t, J=6.24 Hz, 2 H), 6.90 (m, 1 H), 7.03 (m, 3 H), 7.15 (m, 2 H), 7.39 (m, 5 H), 7.66 (m, 1 H), 8.34 (s, 1 H), 9.67 (br s, 1H).

EXAMPLE 5

2-(4-phenoxyphenyl)-N-[1-(2-pyrrolidin-1-ylethyl)-1H-indazol-4-yl]acetamide 1-(2-pyrrolidin-1-yl-ethyl)-1H-indazol-4-ylamine and (4-phenoxy-phenyl)-acetic acid were processed as describe in Example 3 to provide the title compound. $^1$H NMR (300 MHz, DMSO-D6) δ ppm 1.61 (m, 4 H), 2.43 (m, J=5.43 Hz, 4 H), 2.86 (t, J=6.78 Hz, 2 H), 3.78 (s, 2 H), 4.47 (t, J=6.61 Hz, 2 H), 6.99 (m, 4 H), 7.12 (m, 1 H), 7.29 (m, 1 H), 7.39 (m, 5 H), 7.65 (m, 1 H), 8.27 (m, 1 H), 10.17 (m, 1 H); MS (DCI/NH$_3$) m/z 441 [M+H]$^+$.

EXAMPLE 6

3-(4-phenoxyphenyl)-N-[1-(2-pyrrolidin-1-ylethyl)-1H-indazol-4-yl]propanamide 1-(2-pyrrolidin-1-yl-ethyl)-1H-indazol-4-ylamine and 3-(4-phenoxy-phenyl)-propionic acid were processed according as described in Example 3 to provide the title compound. 1H NMR (500 MHz, DMSO-D6) δ ppm 1.84 (m, 2 H), 2.00 (m, 2 H), 2.64 (t, J=7.64 Hz, 2 H), 2.93 (t, J=7.64 Hz, 2 H), 3.06 (m, 2 H), 3.52 (m, 2 H), 3.71 (m, 2 H), 4.74 (t, J=6.08 Hz, 2 H), 6.95 (m, 4 H), 7.11 (m, 1 H), 7.28 (m, 2 H), 7.36 (m, 2 H), 7.49 (m, 1 H), 7.67 (m, 1 H), 8.13 (m, 2 H), 9.95 (s, 1 H); MS (DCI/NH$_3$) m/z 455 [M+H]$^+$.

EXAMPLE 7

2-{4-[(2,3-difluorobenzyl)oxy]phenyl}-N-[1-(2-pyrrolidin-1-ylethyl)-1H-indazol-4-yl]acetamide

EXAMPLE 7A 2-(4-hydroxy-phenyl)-N-[1-(2-pyrrolidin-1-yl-ethyl)-1H-indazol-4-yl]-acetamide 2-(4-Benzyloxy-phenyl)-N-[1-(2-pyrrolidin-1-yl-ethyl)-1H-indazol-4-yl]-acetamide (Example 3, 500 mg, 1.10 mmol) and Pd (50 mg, 10% on carbon) were suspended in ethanol (40 mL) and stirred under a hydrogen atmosphere at room temperature for 6 hours. The mixture was filtered and the filtrate was concentrated under reduced pressure to provide the title compound. $^1$H NMR (300 MHz, DMSO-d$_6$) δ ppm 1.62 (m, 4H), 2.45 (m, 4H), 2.87 (t, 2H, J=6.78), 3.65 (s, 2H), 4.47 (t, 2H, J=6.78), 6.72 (m, 2H), 7.16 (m, 2H), 7.25–7.65 (m, 3H), 8.26 (s, 1H), 9.26 (s, 1H), 10.09 (s, 1H); MS (DCI/NH$_3$) m/z 365 [M+H]$^+$.

EXAMPLE 7

2-{4-[(2,3-difluorobenzyl)oxy]phenyl}-N-[1-(2-pyrrolidin-1-ylethyl)-1H-indazol-4-yl]acetamide A mixture of 2-(4-hydroxy-phenyl)-N-[1-(2-pyrrolidin-1-yl-ethyl)-1H-indazol-4-yl]-acetamide (45.0 mg, 0.124 mmol), 1-bromomethyl-2,3-difluoro-benzene (38.0 mg, 0.185 mmol), Cs$_2$CO$_3$ (60.0 mg, 0.184 mmol) in 2 mL of DMF was shaken for 6 hours after which the mixture was concentrated under reduced pressure. The residue was dissolved in 1.5 mL of a 1:1 mixture of dimethyl sulfoxide/MeOH and purified by preparative reverse-phase HPLC. $^1$H NMR (300 MHz, DMSO-d$_6$) δ ppm 1.61 (m, 4H), 2.44 (m, 4H), 2.86 (t, 2H, J=6.78), 3.72 (s, 2H), 4.47 (t, 2H, J=6.78), 5.18 (s, 2H), 7.00 (m, 2H), 7.19–7.72 (m, 8H), 8.26 (s, 1H), 10.16 (s, 1H); MS (DCI/NH$_3$) m/z 491 [M+H]$^+$.

EXAMPLE 8

N-[1-(2-morpholin-4-ylethyl)-1H-indazol-4-yl]-2-[(4-phenoxybenzyl)amino]acetamide

EXAMPLE 8A 1-(2-morpholin-4-yl-ethyl)-4-nitro-1H-indazole

4-Nitroindazole (1.00 g, 6.13 mmol) and potassium carbonate (2.55 g, 18.4 mmol) in 15 mL of DMF was stirred for 30 min, after which 4-(2-chloro-ethyl)-morpholine hydrochloride (1.71 g, 9.19 mmol) was added. The reaction mixture was heated to 60° C. for 6 hours, cooled to room temperature and filtered through a plug of silica gel which was rinsed with triethylamine/ethyl acetate (1/4). The combined filtrate was concentrated under reduced pressure and the residue purified by flash chromatography (silica gel, triethylamine/ethyl acetate 1/30). 1H NMR (300 MHz, DMSO-D6) δ ppm 2.41 (m, 4 H), 2.79 (t, J=6.27 Hz, 2 H), 3.44 (m, 4 H), 4.66 (t, J=6.27 Hz, 2 H), 7.65 (m, 1 H), 8.17 (m, 1 H), 8.29 (m, 1 H), 8.52 (s, 1 H); MS (DCI/NH$_3$) m/z 277 [M+H]$^+$.

EXAMPLE 8B 1-(2-morpholin-1-yl-ethyl)-1H-indazol-4-ylamine

A mixture of 1-(2-Morpholin-4-yl-ethyl)-4-nitro-1H-indazole (0.700 g, 2.54 mmol), iron powder (1.42 g, 25.4 mmol), and ammonium chloride (0.0680 g, 1.27 mmol) in a 4:1 solution of ethanol/H$_2$O was heated to reflux for 2 hours, cooled to room temperature and concentrated under reduced pressure. The residue was taken up and stirred in triethylamine/ethyl acetate (1/4, 30 mL) for 15 minutes, filtered through a plug of silica gel. The silica gel was rinsed with triethylamine/ethyl acetate (1/4) and the combined filtrate concentrated under reduced pressure to provide the title compound. 1H NMR (300 MHz, DMSO-D6) δ ppm 2.41 (m, 4 H), 2.71 (t, J=6.78 Hz, 2 H), 3.51 (m, 4 H), 4.36 (t, J=6.78 Hz, 2 H), 5.73 (s, 2 H), 6.13 (m, 1 H), 6.68 (m, 1 H), 7.01 (m, 1 H), 8.05 (s, 1 H); MS (DCI/NH$_3$) m/z 247 [M+H]$^+$.

EXAMPLE 8C

{[1-(2-morpholin-4-yl-ethyl)-1H-indazol-4-ylcarbamoyl]-methyl}-carbamic acid tert-butyl ester A mixture of 1-(2-morpholin-1-yl-ethyl)-1H-indazol-4-ylamine (0.150 g, 0.609 mmol), tert-butoxycarbonylaminoacetic acid (0.109 g, 0.548 mmol), ethyldimethylpropylcarbodiimide hydrochloride (0.126 g, 0.660 mmol), N-hydroxybenzotriazole (0.0884 g, 0.657 mmol) and N-methyl morpholine (0.150 mL, 1.33 mmol) in 3.6 mL of DMF was stirred at room temperature for 6 hours. The mixture was concentrated under reduced pressure and the residue purified by flash chromatography to provide the title compound. 1H NMR (300 MHz, DMSO-D6) δ ppm 1.41 (s, 9 H), 2.41 (m, 4 H), 2.75 (t, J=6.61 Hz, 2 H), 3.49 (m, 4 H), 3.86 (d, J=6.10 Hz, 2 H), 4.49 (t, J=6.61 Hz, 2 H), 7.08 (s, 1 H), 7.33 (m, 2 H), 7.64 (m, 1 H), 8.24 (s, 1 H), 9.97 (s, 1 H); MS (DCI/NH$_3$) m/z 404 [M+H]$^+$.

EXAMPLE 8

N-[1-(2-morpholin-4-ylethyl)-1H-indazol-4-yl]-2-[(4-phenoxybenzyl)amino]acetamide Example 8C (0.150 g, 0.372 mmol) and 2 mL of 4M HCl in dioxane in 2 mL of dichloromethane was stirred for 1 hour after which the resulting precipitate was filtered and washed with diethyl ether. The precipitate was dissolved in 2 mL of 1:1 methanol/dichloroethane (containing 1% acetic acid) after which 4-phenoxy-benzaldehyde (9.0550 g, 0.278 mmol) and macroporous cyanoborohydride resin (0.264 g, 2.10 mmol/g, 1.99 equiv) was added. The mixture was shaken at room temperature for 6 hours, after which the mixture was filtered and concentrated under reduced pressure. The residue was purified via column chromatography ((30/1 ethyl acetate/triethylamine)/hexanes) to provide the title compound. 1H NMR (300 MHz, DMSO-D6) δ ppm 2.41 (m, 4 H), 2.74 (t, J=6.61 Hz, 2 H), 3.48 (m, 6 H), 3.82 (s, 2 H), 4.49 (t, J=6.61 Hz, 2 H), 6.97 (m, 4 H), 7.12 (m, 1 H), 7.26–7.36 (m, 2 H), 7.36–7.45 (m, 5 H), 7.68 (m, 1 H), 8.15 (s, 1 H), 10.06 (s, 1 H); MS (DCI/NH$_3$) m/z 486 [M+H]$^+$.

EXAMPLE 9

2-[4-(benzyloxy)phenyl]-N-[1-(2-morpholin-4-yl-ethyl)-1H-indazol-4-yl]acetamide

The title compound was prepared according to the procedure for Example 8C substituting (4-benzyloxy-phenyl)-acetic acid for tert-butoxycarbonylamino-acetic acid. 1H NMR (300 MHz, DMSO-D6) δ ppm 1.34 (m, 2 H), 1.40 (m, 2 H), 2.37 (m, 4 H), 2.69 (t, J=6.61 Hz, 2 H), 3.71 (s, 2 H), 4.46 (t, J=6.78 Hz, 2 H), 5.09 (s, 2 H), 6.94 (m, 2 H), 7.23–7.47 (m, 9 H), 7.62 (m, 1 H), 8.25 (m, 1 H), 10.11 (m, 1H); MS (DCI/NH$_3$) m/z 469 [M+H]$^+$.

EXAMPLE 10

4-(1,1'-biphenyl-4-yl)-N-[1-(2-morpholin-4-ylethyl)-1H-indazol-4-yl]-4-oxobutanamide The title compound was prepared according to the procedure for Example 8C substituting 4-biphenyl-4-yl-4-oxo-butyric acid acid for tert-butoxycarbonylamino-acetic acid. 1H NMR (300 MHz, DMSO-D6) δ ppm 2.41 (m, 4 H), 2.75 (m, 2 H), 2.89 (m, 2 H), 3.43 (t, J=6.61 Hz, 2 H), 3.49 (m, 4 H), 4.49 (m, 2 H), 7.31 (m, 2 H), 7.44 (m, 1 H), 7.52 (m, 2 H), 7.67 (m, 1 H), 7.77 (m, 2 H), 7.84 (m, 2 H), 8.11 (m, 2 H), 8.32 (m, 1 H), 10.09 (s, 1 H); MS (DCI/NH$_3$) m/z 483 [M+H]$^+$.

EXAMPLE 11

2-[(4-phenoxybenzyl)amino]-N-[1-(2-piperidin-1-ylethyl)-1H-indazol-4-yl]acetamide

EXAMPLE 11A 4-nitro-1-(2-piperidin-1-yl-ethyl)-1H-indazole

4-Nitroindazole (mmol) and potassium carbonate (mmol) in 60 mL of DMF was added was stirred for 30 minutes, after which 4-(2-chloro-ethyl)-piperidine hydrochloride (mmol) was added. The mixture was heated to 60° C. for 6 hours, cooled to room temperature and the mixture filtered through a plug of silica gel which was rinsed with triethylamine/ethyl acetate (1/4). The filtrate was concentrated under reduced pressure, and the residue purified by flash chromatography (silica gel, triethylamine/ethyl acetate 1/30). 1H NMR (300 MHz, DMSO-D6) δ ppm 1.39 (m, 6 H), 2.36 (m, 4 H), 2.73 (t, J=6.44 Hz, 2 H), 4.63 (t, J=6.44 Hz, 2 H), 7.64 (m, 1 H), 8.16 (m, 1 H), 8.28 (m; 1 H), 8.51 (s, 1 H); MS (DCI/NH$_3$) m/z 275 [M+H]$^+$.

EXAMPLE 11B 1-(2-piperidin-1-yl-ethyl)-1H-indazol-4-ylamine

A mixture of 4-Nitro-1-(2-piperidin-1-yl-ethyl)-1H-indazole (mmol), iron powder (mmol), and ammonium chloride (mmol) in a 4:1 solution of ethanol/H$_2$O was heated to reflux for 2 hours, cooled to room temperature and concentrated under reduced pressure. The residue was stirred in triethylamine/ethyl acetate (1/4, 30 mL) for 15 minutes and filtered through a plug of silica gel which was rinsed with triethylamine/ethyl acetate (1/4). The filtrate was concentrated under reduced pressure to provide the title compound. 1H NMR (300 MHz, DMSO-D6) δ ppm 1.36 (m, 2 H), 1.44 (m, 4 H), 2.37 (m, 4 H), 2.66 (t, J=6.95 Hz, 2 H), 4.33 (t, J=6.95 Hz, 2 H), 5.71 (m, 2 H), 6.12 (m, 1 H), 6.66 (m, 1 H), 6.99 (m, 1 H), 8.02 (m, 1 H); MS (DCI/NH$_3$) m/z 245 [M+H]$^+$.

EXAMPLE 11C tert-butyl 2-oxo-2-{[1-(2-piperidin-1-ylethyl)-1H-indazol-4-yl]amino}ethylcarbamate A mixture of 1-(2-piperidin-1-yl-ethyl)-1H-indazol-4-ylamine (mmol), tert-butoxycarbonylamino-acetic acid (mmol), ethyldimethylpropylcarbodiimide hydrochloride (mmol), N-hydroxybenzotriazole (mmol) and N-methyl morpholine (mmol) were dissolved in 15 mL of DMF and stirred at room temperature for 6 hours. The mixture was concentrated under reduced pressure and the residue purified by flash chromatography to provide the title compound. 1H NMR (300 MHz, DMSO-D6) δ ppm 1.34 (m, J=4.41 Hz, 6 H), 1.41 (s, 9 H), 2.37 (m, 4 H), 2.69 (t, J=6.78 Hz, 2 H), 3.86 (d, J=6.10 Hz, 2 H), 4.46 (t, J=6.78 Hz, 2 H), 7.08 (s, 1 H), 7.32 (m, 2 H), 7.64 (m, 1 H), 8.23 (s, 1 H), 9.96 (s, 1 H); MS (DCI/NH$_3$) m/z 469 [M+H]$^+$.

EXAMPLE 11

2-[(4-phenoxybenzyl)amino]-N-[1-(2-piperidin-1-ylethyl)-1H-indazol-4-yl]acetamide Example 11C (0.144 g, 0.359 mmol) and 2 mL of 4M HCl in dioxane in 2 mL of dichloromethane was stirred for 1 hour after which the formed precipitate was filtered and washed with Et$_2$O. The filtered solid was taken up in 3 mL of 1:1 methanol/dichloroethane (1% acetic acid) along with 4-phenoxy-benzaldehyde (65.0 mg, 0.328 mmol) and macroporous cyanoborohydride resin (0.309 g, 2.10 mmol/g, 1.99 equiv) and the resulting mixture was shaken at room temperature for 6 hours. The mixture was filtered, concentrated under reduced pressure and the residue purified via column chromatography ((30/1 ethyl acetate/triethylamine)/hexanes) to provide the title compound. 1H NMR (300 MHz, DMSO-D6) δ ppm 1.29–1.38 (m, 2 H), 1.38–1.49 (m, 4 H), 2.30–2.47 (m, 4 H), 2.70 (t, J=6.78 Hz, 2 H), 3.42 (s, 2 H), 3.79 (s, 2 H), 4.46 (t, J=6.61 Hz, 2 H), 6.91–7.01 (m, 4 H), 7.12 (m, 1 H) 7.26–7.46 (m, 7 H), 7.68 (m, 1 H), 8.14 (s, 1 H), 9.97 (s, 1 H); MS (DCI/NH$_3$) m/z 484 [M+H]$^+$.

EXAMPLE 12

2-(4-phenoxyphenyl)-N-[1-(2-piperidin-1-ylethyl)-1H-indazol-4-yl]acetamide

The title compound was prepared according to the procedure for Example 11C substituting (4-benzyloxy-phenyl)-acetic acid for tert-butoxycarbonylamino-acetic acid. 1H NMR (300 MHz, DMSO-D6) δ ppm 2.40 (m, 4 H), 2.50 (m, 2 H), 2.74 (t, J=6.61 Hz, 2 H), 3.48 (m, 4 H), 3.71 (s, 2 H), 5.09 (m, 2 H), 5.09 (s, 2 H), 6.98 (m, 2 H), 7.28 (m, 4 H), 7.41 (m, 5 H), 7.63 (m, 1 H), 8.26 (s, 1 H), 10.13 (s, 1 H); MS (DCI/NH$_3$) m/z 469 [M+H]$^+$.

EXAMPLE 13

N-[1-(2-dimethylamino-ethyl)-1H-indazol-4-yl]-2-(4-phenoxy-phenyl)-acetamide

EXAMPLE 13A dimethyl-[2-(4-nitro-indazol-1-yl)-ethyl]-amine

A mixture of 4-nitroindazole (2.0 g, 12 mmol) and potassium carbonate (5.1 g 37 mmol) in DMF (40 mL) was stirred for 30 minutes, after which 2-(dimethylamino)ethylchloride hydrochloride (2.7 g 18 mmol) was added. The mixture was heated to 60° C. for 6 hours, cooled to room temperature and filtered through a plug of silica gel, which was rinsed with triethylamine/ethyl acetate (1/4). The combined filtrate was concentrated under reduced pressure and purified by Flash Chromatography (silica gel, triethylamine/ethyl acetate 1/30) to provide the title compound (1.6g, 50% yield). $^1$H NMR (300 MHz, DMSO-d$_6$) ppm 2.74(t, J=6.44, 2H), 3.31 (s, 6H), 4.63 (t, J=6.44, 2H), 7.64 (m, 1H), 8.16 (m, 1H), 8.30 (m, 1H), 8.51(m, 1H); MS (DCI/NH$_3$) m/z 235 [M+H]$^+$.

EXAMPLE 13

N-[1-(2-dimethylamino-ethyl)-1H-indazol-4-yl]-2-(4-phenoxy-phenyl)-acetamide

A mixture of dimethyl-[2-(4-nitro-indazol-1-yl)-ethyl]-amine (1.6 g, 6.8 mmol), iron powder (3.8 g, 68 mmol), and ammonium chloride (0.18 g, 3.4 mmol) in a 4:1 ethanol/H$_2$O solution (20 mL) was heated to reflux for 3 hours, cooled to room temperature and concentrated under reduced pressure. The residue was taken up and stirred in triethylamine/ethyl acetate (1/4, 10 mL) for 15 minutes and then filtered through a plug of silica gel which was rinsed with triethylamine/ethyl acetate (1/4). The combined filtrate was concentrated under reduced pressure to provide a play yellow oil. This material was then processed with (4-phenoxy-phenyl)-acetic acid according to the procedure described in Example 5 to provide the title compound. $^1$H NMR (300 MHz, DMSO-d$_6$) ppm 2.85 (s, 6H), 3.62 (t, J=6.24, 2H), 3.80 (s, 2H), 4.78 (t, J=6.24, 2H), 6.99–7.01 (m, 3H), 7.13 (m, 2H), 7.36–7.40 (m, 5H), 7.45 (m, 1H), 7.71 (m, 1H), 8.40 (s, 1H), 9.61 (s, 1H); MS (DCI/NH$_3$) m/z 415 [M+H]$^+$.

EXAMPLE 14

2-[4-(benzyloxy)phenyl]-N-(1-{2-[(2R)-2-methylpyrrolidin-1-yl]ethyl}-1H-indazol-4-yl)acetamide

EXAMPLE 14A

1-{2-[(2R)-2-methylpyrrolidin-1-yl]ethyl}-4-nitro-1H-indazole

A mixture of 1.50 g (9.20 mmol) of 4-nitroindazole and 2.79 g (20.2 mmol) of Cs$_2$CO$_3$ in 23 mL of DMF was stirred for 15 minutes after which 1.31 mL (11.1 mmol) of 2-bromo-1,1-dimethoxy-ethane was added. The mixture was heated to 55° C. for 12 hours, cooled to room temperature and the contents filtered through a bed of celite. The filtrate was concentrated under reduced pressure and the residue purified via column chromatography (30–80% ethyl acetate/hexanes with 1% triethylamine) to provide 1.31 g as a mixture of N1 and N2-alkylated 4-nitroindazoles.

800 mg (3.49 mmol) of the residue and 5 mL of 3M HCl (aqueous) in 5 mL THF was heated to 60° C. for 16 hours. The mixture was cooled to room temperature and concentrated under reduced pressure. 240 mg (1.17 mmol) of this material was taken up in methanol (1% acetic acid) and 123 mg (1.17 mmol) of 2-methylpyrrolidine was added, followed by 1.38 g of macroporous cyanoborohydride resin (2.10 mmol/g, 2.48 equiv). The mixture was shaken at room temperature for 16 hour, filtered and concentrated under reduced pressure and the residue purified by Column chromatography (50–80% ethyl acetate/hexanes with 1% triethylamine) to provide the title compound. 1H NMR (300 MHz, DMSO-D6) δ ppm 0.78 (d, J=6.10 Hz, 3 H), 1.13 (m, 1 H), 1.57 (m, 2 H), 1.79 (m, 1 H), 2.13 (q, J=8.82 Hz, 1 H), 2.32 (m, 1 H), 2.56 (m, 1 H), 3.08 (m, 1 H), 3.22 (m, 1 H), 4.61 (m, 2 H), 7.64 (m, 1 H), 8.17 (m, 1 H), 8.28 (m, 1 H), 8.52 (s, 1 H); MS (DCI/NH$_3$) m/z 275 [M+H]$^+$.

EXAMPLE 14

2-[4-(benzyloxy)phenyl]-N-(1-{2-[(2R)-2-methylpyrrolidin-1-yl]ethyl}-1H-indazol-4-yl)acetamide To a solution of 68.0 (0.250 mmol) of Example 13A, 0.0070 g (0.13 mmol) of NH$_4$Cl in 2.5 mL of 80% ethanol was added 138.0 mg (2.47 mmol) of Fe, and the mixture heated to reflux for 3 hours. The mixture was cooled to room temperature, concentrated under reduced pressure and the residue taken up in 30:1 ethyl acetate:triethylamine and filtered through a plug of silica gel, eluting with the same mixture. The filtrate was concentrated under reduced pressure to provide 55.0 mg of a pale yellow oil.

The residue, 46.0 mg N-hydroxybenzotriazole (0.341 mmol), 0.170 mL of diisopropylethylamine (0.976 mmol), and 65.0 mg (0.269 mmol) of (4-benzyloxy-phenyl)-acetic acid was dissolved in 4 mL of DMF followed by the addition of 0.520 mg of PS-DCC resin (1.3 mmol/g, 0.676 mmol, 2.83 equiv) after which it was shaken and heated to 55° C. for 12 hours. The mixture was cooled to room temperature and the contents filtered through a sintered glass funnel. The filtrate was concentrated under reduced pressure and the residue prurified by silica gel column chromatography eluting with 50–100% ethyl acetate (3.5% triethylamine) to provide the title compound. 1H NMR (300 MHz, DMSO-D6) δ ppm 0.88 (d, J=6.10 Hz, 3 H), 1.20 (m, 1 H), 1.59 (m, 2 H), 1.80 (m, 1 H), 2.11 (q, J=8.81 Hz, 1 H), 2.30 (m, 1 H), 2.46 (m, 1 H), 3.06 (m, 1 H), 3.20 (m, 1 H), 3.71 (s, 2 H), 4.44 (t, J=6.78 Hz, 2 H), 5.09 (s, 2 H), 6.98 (m, 2 H), 7.36 (m, 9 H), 7.63 (m, 1 H), 8.26 (s, 1 H), 10.11 (s, 1 H); MS (DCI/NH$_3$) m/z 469 [M+H]$^+$.

EXAMPLE 15

2-[4-(benzyloxy)phenyl]-N-(1-{2-[(2R)-2-methylpiperidin-1-yl]ethyl}-1H-indazol-4-yl)acetamide The title compound was prepared according to the procedure for Example 14 substituting 2-methylpiperidine for 2-methylpyrrolidine. 1H NMR (300 MHz, DMSO-D6) δ ppm 0.87 (d, J=6.44 Hz, 3 H), 1.06 (m, 1 H), 1.31 (m, 2 H), 1.46 (m, 3 H), 2.18 (m, 2 H), 2.29 (m, 1 H), 2.64 (m, 1 H), 2.82 (m, 1 H), 3.70 (s, 2 H), 4.41 (t, J=6.61 Hz, 2 H), 5.09 (s, 2 H), 6.98 (m, 2 H), 7.35 (m, 9 H), 7.64 (m, 1 H), 8.26 (s, 1 H), 10.11 (s, 1 H); MS (DCI/NH$_3$) m/z 483 [M+H]$^+$.

EXAMPLE 16

2-[4-(benzyloxy)phenyl]-N-(1-{2-[(3R)-3-methylpiperidin-1-yl]ethyl}-1H-indazol-4-yl)acetamide The title compound was prepared according to the procedure for Example 14 substituting 3-methylpiperidine for 2-methylpyrrolidine. 1H NMR (300 MHz, DMSO-D6) δ ppm 0.78 (d, J=6.44 Hz, 3 H), 1.35 (m, 2 H), 1.54 (m, 4 H), 1.87 (m, 1 H), 2.69 (t, J=6.78 Hz, 2 H), 2.78 (m, 2 H), 3.70 (s, 2 H), 4.46 (t, J=6.78 Hz, 2 H), 5.08 (s, 2 H), 6.98 (m, 2 H), 7.35 (m, 9 H), 7.63 (m, 1 H), 8.25 (s, 1 H), 10.11 (s, 1 H); MS (DCI/NH$_3$) m/z 483 [M+H]$^+$.

EXAMPLE 17

2-[4-(benzyloxy)phenyl]-N-[1-(2-pyrrolidin-1-yl-ethyl)-1H-indazol-5-yl]acetamide

EXAMPLE 17A 5-nitro-1-(2-pyrrolidin-1-yl-ethyl)-1H-indazole

A mixture of 5-nitroindazole (3.00 g, 18.4 mmol) and potassium carbonate (7.50 g, 54.4 mmol) in DMF (60 mL) was stirred for 30 minutes after which 1-(2-chloro-ethyl)-pyrrolidine hydrochloride (4.80 g, 28.4 mmol) was added. The mixture was heated to 60° C. for 6 hours, cooled to room temperature and filtered through a plug of silica gel which was rinsed with triethylamine/ethyl acetate (1/4). The filtrate was concentrated under reduced pressure and the residue purified by flash chromatography (silica gel, triethylamine/ethyl acetate 1/30) to provide the title compound. 1H NMR (300 MHz, DMSO-d$_6$) δ ppm 1.60 (m, 4H), 2.44 (m, 4H), 2.90 (t, 2H, J=6.45), 4.59 (t, 2H, J=6.45), 7.90 (m, 1H), 8.20 (m, 1H), 8.39 (s, 1H), 8.80 (s, 1H); MS (DCI/NH$_3$) m/z 261 [M+H]$^+$.

EXAMPLE 17B 1-(2-pyrrolidin-1-yl-ethyl)-1H-indazol-5-ylamine

A mixture of 5-Nitro-1-(2-pyrrolidin-1-yl-ethyl)-1H-indazole (3.00 g, 11.5 mmol), iron powder (6.50 g, 116 mmol), and ammonium chloride (310 mg, 5.85 mmol) in a 4:1 mixture of ethanol/H$_2$O was heated to reflux for 3 hours, cooled to room temperature and concentrated under reduced pressure. The residue was taken up and stirred in triethylamine/ethyl acetate (1/4, 30 mL) for 15 minutes, filtered through a plug of silica gel which was rinsed with triethylamine/ethyl acetate (1/4). The filtrate was concentrated under reduced pressure to provide the title compound. 1H NMR (300 MHz, DMSO-d$_6$) δ ppm 1.62 (m, 4H), 2.44 (m, 4H), 2.81 (t, 2H, J=6.78), 4.36 (t, 2H, J=6.78), 4.77 (s, 2H), 6.72 (m, 1H), 6.79 (m, 1H), 7.35 (m, 1H), 7.68 (s, 1H); MS (DCI/NH$_3$) m/z 231 [M+H]$^+$.

EXAMPLE 17

2-[4-(benzyloxy)phenyl]-N-[1-(2-pyrrolidin-1-yl-ethyl)-1H-indazol-5-yl]acetamide A mixture of 1-(2-pyrrolidin-1-yl-ethyl)-1H-indazol-5-ylamine (60 mg, 0.26 mmol), (4-benzyloxy-phenyl)-acetic acid (63 mg, 0.26 mmol), ethyldimethylpropylcarbodiimide hydrochloride (60 mg g, 0.31 mmol), N-hydroxybenzotriazole (42 mg, 0.31 mmol), and N-methyl morpholine (66 mg, 0.62 mmol) in 2 mL of DMF was shaken for 6 hours. The mixture was concentrated under reduced pressure and the residue was dissolved in 1.5 mL of a 1:1 mixture of dimethyl sulfoxide/methanol and purified by preparative reverse-phase HPLC. 1H NMR (300 MHz, DMSO-d$_6$) δ ppm 1.61 (m, 4H), 2.43 (m, 4H), 2.86 (t, 2H, J=6.78), 3.56 (s, 2H), 4.45 (t, 2H, J=6.78), 5.08 (s, 2H), 6.97 (m, 2H), 7.25–7.31 (m, 6H), 7.27 (m, 2H), 7.59 (m, 1H), 7.97 (s, 1H), 8.08 (s, 1H), 10.10 (s, 1H); MS (DCI/NH$_3$) m/z 455 [M+H]$^+$.

EXAMPLE 18

3-(4-phenoxyphenyl)-N-[1-(2-pyrrolidin-1-ylethyl)-1H-indazol-5-yl]propanamide 1-(2-pyrrolidin-1-yl-ethyl)-1H-indazol-5-ylamine and 3-(4-phenoxy-phenyl)-propionic acid were processed as described in Example 17 to provide the title compound. 1H NMR (500 MHz, DMSO-D6) δ ppm 1.83 (m, 2 H), 1.99 (m, 2 H), 2.60 (t, J=7.64 Hz, 2 H), 2.87 (t, J=7.49 Hz, 2 H), 3.04 (m, 2 H), 3.52 (m, 2 H), 3.70 (m, 2 H), 4.73 (t, J=6.08 Hz, 2 H), 5.06 (s, 2 H), 6.92 (m, 2 H), 7.17 (m, 2 H), 7.32 (m, 1 H), 7.40 (m, 4 H), 7.49 (m, 1 H), 7.66 (m, 1 H), 8.13 (m, 2 H), 9.93 (s, 1 H); MS (DCI/NH$_3$) m/z 469 [M+H]$^+$.

EXAMPLE 19

2-(3-phenoxyphenyl)-N-[1-(2-pyrrolidin-1-ylethyl)-1H-indazol-5-yl]acetamide 1-(2-pyrrolidin-1-yl-ethyl)-1H-indazol-5-ylamine and (3-phenoxy-phenyl)-acetic acid were processed as described in Example 17 to provide the title compound. MS (DCI/NH$_3$) MS m/z 441 (M+H)$^+$; $^1$H NMR (500 MHz, DMSO-d$_6$) δ ppm 1.83 (m, 2 H), 1.99 (m, 2 H), 3.04 (m, 2 H), 3.52 (m, 2 H), 3.65 (s, 2 H), 3.71 (q, J=5.61 Hz, 2 H), 4.74 (t, J=6.24 Hz, 2 H), 6.89 (m, 1 H), 7.02 (m, 3 H), 7.14 (m, 2 H), 7.37 (m, 3 H), 7.51 (m, 1 H), 7.68 (m, 1 H), 8.12 (m, 2 H), 9.68 (br s, N H).

EXAMPLE 20

4-(4-chlorophenyl)-N-[1-(2-pyrrolidin-1-ylethyl)-1H-indazol-5-yl]cyclohexanecarboxamide 1-(2-pyrrolidin-1-yl-ethyl)-1H-indazol-5-ylamine and 4-(4-chloro-phenyl)-cyclohexanecarboxylic acid were processed as described in Example 17 to provide the title compound. MS (DCI/NH$_3$) MS m/z 451 (M+H)$^+$; $^1$H NMR (500 MHz, DMSO-d$_6$) δ ppm 1.48 (m, 2 H), 1.64 (m, 2 H), 1.75–2.06 (m, 8 H), 2.42 (m, 1 H), 2.57 (m, 1 H), 3.03 (m, 2 H), 3.52 (m, 2 H), 3.71 (q, J=5.82 Hz, 2 H), 4.74 (t, J=6.24 Hz, 2 H), 7.29 (m, 2 H), 7.35 (m, 2 H), 7.55 (m, 1 H), 7.67 (m, 1 H), 8.13 (s, 1 H), 8.18 (s, 1 H), 9.69 (br s, N H).

EXAMPLE 21

3-(4-phenoxyphenyl)-N-[1-(2-pyrrolidin-1-ylethyl)-1H-indazol-5-yl]propanamide 1-(2-pyrrolidin-1-yl-ethyl)-1H-indazol-5-ylamine and 3-(4-phenoxy-phenyl)-propionic acid were processed as described in Example 17 to provide the title compound. MS (DCI/NH$_3$) MS m/z 455 (M+H)$^+$; $^1$H NMR (500 MHz, DMSO-d$_6$) δ ppm 1.83 (m, 2 H), 1.99 (m, 2 H), 2.79 (t, J=7.64 Hz, 2 H), 2.96 (t, J=7.49 Hz, 2 H), 3.06 (m, 2 H), 3.52 (m, 2 H), 3.71 (q, J=5.61 Hz, 2 H), 4.74 (t, J=6.24 Hz, 2 H), 6.95 (m, 4 H), 7.11 (m, 1 H), 7.30 (m, 2 H), 7.37 (m, 3 H), 7.43 (m, 1 H), 7.68 (m, 1 H), 8.31 (s, 1 H), 9.67 (br s, N H).

EXAMPLE 22

2-(4-phenoxyphenyl)-N-[1-(2-pyrrolidin-1-ylethyl)-1H-indazol-5-yl]acetamide 1-(2-pyrrolidin-1-yl-ethyl)-1H-indazol-5-ylamine and (4-phenoxy-phenyl)-acetic acid were processed as described in Example 17 to provide the title compound. MS (DCI/NH$_3$) MS m/z 441 (M+H)$^+$; $^1$H NMR (500 MHz, DMSO-d$_6$) δ ppm 1.83 (m, 2 H), 1.99 (m, 2 H), 3.05 (m, 2 H), 3.52 (m, 2 H), 3.65 (s, 2 H), 3.71 (q, J=5.93 Hz, 2 H), 4.74 (t, J=6.24 Hz, 2 H), 6.99 (m, 4 H), 7.13 (m, 1 H), 7.37 (m, 4 H), 7.54 (m, 1 H), 7.69 (m, 1 H), 8.14 (m, 2 H), 9.63 (br s, N H).

EXAMPLE 23

(2E)-3-(1,1'-biphenyl-4-yl)-N-[1-(2-pyrrolidin-1-ylethyl)-1H-indazol-5-yl]acrylamide 1-(2-pyrrolidin-1-yl-ethyl)-1H-indazol-5-ylamine and 3-biphenyl-4-yl-acrylic acid were processed as described in Example 17 to provide the title compound. MS (DCI/NH$_3$) MS m/z 437 (M+H)$^+$; $^1$H NMR (500 MHz, DMSO-d$_6$) δ ppm 1.84 (m, 2 H), 1.99 (m, 2 H), 3.06 (m, 2 H), 3.53 (m, 2 H), 3.72 (m, 2 H), 4.76 (t, J=5.93 Hz, 2 H), 6.91 (m, 1 H), 7.40 (m, 1 H), 7.50 (m, 2 H), 7.64 (m, 2 H), 7.75 (m, 7 H), 8.18 (s, 1 H), 8.31 (s, 1 H), 9.56 (br s, N H)

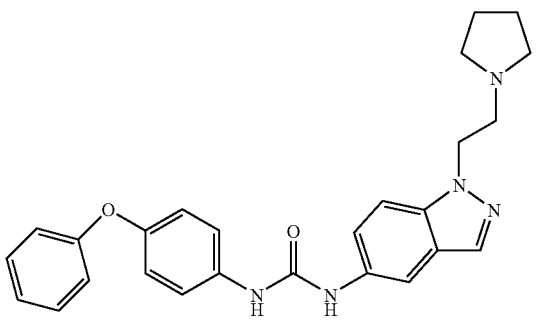

EXAMPLE 24

N-(4-phenoxyphenyl)-N'-[1-(2-pyrrolidin-1-ylethyl)-1H-indazol-5-yl]urea

A mixture of 2-(2-pyrrolidin-1-yl-ethyl)-1H-indazol-5-ylamine (0.100 g, 0.434 mmol) and 4-phenoxyphenyl isocyanate (0.0917 g, 0.434 mmol) in 6 mL of THF was stirred at 50° C. for 1 hour, cooled to room temperature and concentrated under reduced pressure. The residue was triturated in diethyl ether and collected by filtration to provide the title compound. 1H NMR (300 MHz, DMSO-D6) δ ppm 1.63 (m, 4 H), 2.44 (m, J=6.44 Hz, 4 H), 2.86 (t, J=6.61 Hz, 2 H), 4.46 (t, J=6.78 Hz, 2 H), 6.97 (m, 4 H), 7.09 (m, 1 H), 7.35 (m, 3 H), 7.49 (m, 2 H), 7.59 (m, 1 H), 7.88 (m, 1 H), 7.96 (s, 1 H), 8.65 (m, 2 H); MS (ESI) m/z 442 [M+H]$^+$.

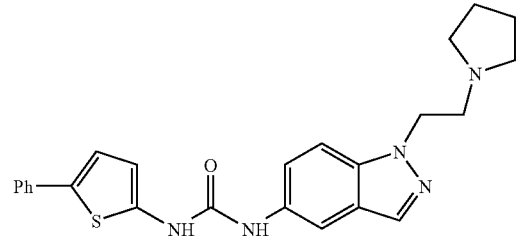

EXAMPLE 25

N-(5-phenylthien-2-yl)-N'-[1-(2-pyrrolidin-1-ylethyl)-1H-indazol-5-yl]urea

The title compound was prepared according to the procedure for Example 24 substituting 5-phenyl-2-thienyl isocyanate for 4-phenoxyphenyl isocyanate. 1H NMR (300 MHz, DMSO-D6) δ ppm 1.83 (m, 2 H), 2.01 (m, 2 H), 3.06 (m, 2 H), 3.55 (m, 2 H), 3.71 (m, 2 H), 4.75 (t, J=6.27 Hz, 2 H), 6.56 (m, 1 H), 7.21 (m, 2 H), 7.37 (m, 2 H), 7.47 (m, 1 H), 7.56 (m, 2 H), 7.69 (m, 1 H), 7.97 (m, 1 H), 8.13 (s, 1 H), 8.90 (s, 1 H), 9.85 (s, 1 H); MS (DCI/NH$_3$) m/z 432 (M+H)$^+$.

EXAMPLE 26

1-(4-phenylamino-phenyl)-3-[1-(2-pyrrolidin-1-yl-ethyl)-1H-indazol-5-yl]-urea

EXAMPLE 26A 1-(4-nitro-phenyl)-3-[1-(2-pyrrolidin-1-yl-ethyl)-1H-indazol-5-yl]-urea A mixture of 1-(2-pyrrolidin-1-yl-ethyl)-1H-indazol-5-ylamine (2.0 g, 8.7 mmol) and 4-nitrophenyl isocyanate (1.5 g, 8.8 mmol) in 150 mL of THF was heated to reflux for 2 hours. The solution was cooled to room temperature and concentrated under reduced pressure. The residue was taken up in 100 mL of ethyl acetate and tritutrated to provide a precipitate which was collected filtration to provide the title compound (3.1 g, 91%). $^1$H NMR (300 MHz, DMSO-d$_6$) ppm 1.64 (m, 4H), 2.45 (m, 4H), 2.86 (d, J=6.44, 2H), 4.48 (d, J=6.44, 2H), 7.37 (m, 1H), 7.63 (m, 1H), 7.70 (m, 2H), 7.90 (m, 1H), 7.99 (s, 1H), 8.19 (m, 2H), 8.89 (s, 1H), 9.43 (s, 1H); MS (DCI/NH$_3$) m/z 395 [M+H]$^+$.

EXAMPLE 26B 1-(4-amino-phenyl)-3-[1-(2-pyrrolidin-1-yl-ethyl)-1H-indazol-5-yl]-urea A mixture of 1-(4-nitro-phenyl)-3-[1-(2-pyrrolidin-1-yl-ethyl)-1H-indazol-5-yl]-urea (3.1 g, 7.8 mmol), iron powder (3.5 g, 63 mmol), and ammonium chloride (0.21 g, 3.9 mmol) in a 4:1 ethanol/H$_2$O solution (50 mL) was heated to reflux for 3 hours, cooled to room temperature and concentrated under reduced pressure. The residue was taken up and stirred in triethylamine/ethyl acetate (1/4, 30 mL) for 15 minutes followed by filteration through a plug of silica gel which was rinsed with triethylamine/ethyl acetate (1/4). The filtrate was concentrated under reduced pressure to provide the title compound (2.6 g, 92%). $^1$H NMR (300 MHz, DMSO-d$_6$) ppm 1.89 (m, 4H), 3.06 (m, 4H), 3.64(m, 2H), 4.75 (d, J=6.44, 2H), 6.52 (m, 2H), 7.09 (m, 2H), 7.39 (m, 1H), 7.66 (m, 1H), 7.92 (m, 1H), 8.06 (s, 1H), 8.31 (m, 1H), 8.70 (s, 1H); MS (DCI/NH$_3$) m/z 365 [M+H]$^+$.

EXAMPLE 26

1-(4-phenylamino-phenyl)-3-[1-(2-pyrrolidin-1-yl-ethyl)-1H-indazol-5-yl]-urea

A mixture of 1-(4-amino-phenyl)-3-[1-(2-pyrrolidin-1-yl-ethyl)-1H-indazol-5-yl]-urea (364 mg, 1 mmol), phenylboronic acid (244 mg, 2 mmol), copper(II) acetate (364 mg, 2 mmol), triethylamine (0.2 mL, 2 mmol), in 20 mL of dichloromethane was refluxed overnight. The mixture was concentrated under reduced pressure and the residue was purified by flash chromatography (acetonitrile/ethyl acetate/triethylamine, 10/4/1) to provide the title compound as a pale white solid (200 mg, 45%). $^1$H NMR (300 MHz, DMSO-d$_6$) ppm 1.63 (m, 4H), 2.45 (m, 4H), 2.86 (d, J=6.44, 2H), 4.46 (d, J=6.44, 2H), 6.74 (m, 1H), 6.98 (m, 2H), 7.03 (m, 2H), 7.18 (m, 1H), 7.33–7.36 (m, 3H), 7.58 (m, 1H), 7.88 (m, 1H), 7.90 (s, 1H), 7.95 (s, 1H), 8.44 (s, 1H), 8.55 (s, 1H); MS (DCI/NH$_3$) m/z 441 [M+H]$^+$.

EXAMPLE 27

N-[1-(2-dimethylamino-ethyl)-1H-indazol-5-yl]-2-(4-phenoxy-phenyl)-acetamide

EXAMPLE 27A dimethyl-[2-(5-nitro-indazol-1-yl)-ethyl]-amine

A mixture of 5-nitroindazole (2 g, 12 mmol) and potassium carbonate (5.1 g 37 mmol) in DMF (40 mL) was stirred for 30 minutes after which 2-(dimethylamino)ethylchloride hydrochloride (2.65 g 18.4 mmol) was added. The mixture was heated to 60° C. for 6 hours, cooled to room temperature and was filtered through a plug of silica gel, which was rinsed with triethylamine/ethyl acetate (1/4). The filtrate was concentrated under reduced pressure and purified by flash chromatography (silica gel, triethylamine/ethyl acetate 1/30) to provide the title compound (1.8 g, 64% yield). $^1$H NMR (300 MHz, DMSO-d$_6$) ppm 2.73(t, J=6.44, 2H), 3.33 (s, 6H), 4.57 (t, J=6.44, 2H), 7.93 (m, 1H), 8.21 (m, 1H), 8.40 (m, 1H), 8.82 (m, 1H); MS (DCI/NH$_3$) m/z 235 [M+H]$^+$.

EXAMPLE 27B 1-(2-dimethylamino-ethyl)-1H-indazol-5-ylamine

A mixture of dimethyl-[2-(5-nitro-indazol-1-yl)-ethyl]-amine (1 g, 4.3 mmol), iron powder (1.9 g, 34 mmol), and ammonium chloride (120 mg, 2.2 mmol) in a 4:1 ethanol/H$_2$O solution (20 mL) was heated to reflux for 3 hours, cooled to room temperature and concentrated under reduced pressure. The residue was stirred in triethylamine/ethyl acetate (1/4, 10 mL) for 15 minutes and then filtered through a plug of silica gel which was rinsed with triethylamine/ethyl acetate (1/4). The filtrate was concentrated under reduced pressure to provide the title compound (0.80 g, 92%). $^1$H NMR (300 MHz, DMSO-d$_6$) ppm 2.15 (s, 6H), 2.64 (t, J=6.44, 2H), 4.34 (t, J=6.44, 2H), 4.77 (s, 2H), 6.72 (m, 1H), 6.79 (m, 1H), 7.35 (m, 1H), 7.67 (m, 1H); MS (DCI/NH$_3$) m/z 205 [M+H]$^+$.

EXAMPLE 27

N-[1-(2-dimethylamino-ethyl)-1H-indazol-5-yl]-2-(4-phenoxy-phenyl)-acetamide

A mixture of 1-(2-dimethylamino-ethyl)-1H-indazol-5-ylamine (42 mg, 0.20 mmol), 4-phenoxy-phenylacetic acid (47 mg, 0.21 mmol), ethyldimethylpropylcarbodiimide hydrochloride (43 mg g, 0.22 mmol), N-hydroxybenzotriazole (30 mg, 0.22 mmol), N-methyl morpholine (46 mg, 0.44 mmol) in 2 mL of DMF was shaken for 6 hours. The mixture was concentrated under reduced pressure, the residue taken up in 1.5 mL of a 1:1 mixture of DMSO/MeOH and purified by preparative reverse-phase HPLC. $^1$H NMR (300 MHz, DMSO-d$_6$) ppm 2.84 (s, 6H), 3.65 (s, 2H), 3.62 (t, J=6.24, 2H), 4.76 (t, J=6.24, 2H), 6.97–7.00 (m, 4H), 7.11–7.14 (m, 1H), 7.36–7.40 (m, 4H), 7.64 (m, 1H), 7.69 (m, 1H), 8.12 (m, 1H), 8.15 (m, 1H), 9.58 (s, 1H); MS (DCI/NH$_3$) m/z 415 [M+H]$^+$.

EXAMPLE 28

1-[1-(2-dimethylamino-ethyl)-1H-indazol-5-yl]-3-(4-phenoxy-phenyl)-urea

A mixture of 1-(2-dimethylamino-ethyl)-1H-indazol-5-ylamine (42 mg, 0.17 mmol), 4-phenoxyphenyl isocyanate (36 mg, 0.17 mmol) in 2 mL of THF was heated to 50° C. for 6 hours, cool to room temperature and concentrated under reduced pressure. The residue was dissolved in 1.5 mL of a 1:1 mixture of dimethyl sulfoxide/methanol and purified by preparative reverse-phase HPLC. $^1$H NMR (300 MHz, DMSO-$d_6$) ppm 2.85 (s, 6H), 3.63 (t, J=6.40, 2H), 4.77 (t, J=6.40, 2H), 7.09 (m, 2H), 6.97 (m, 4H), 7.36 (m, 2H), 7.47 (m, 1H), 7.57 (m, 2H), 7.67 (m, 1H), 7.97 (s, 1H), 8.10 (s, 1H), 8.98 (s, 1H); MS (DCI/NH$_3$) m/z 416 [M+H]$^+$.

EXAMPLE 29

2-(4-phenoxy-phenyl)-N-[1-(2-piperidin-1-yl-ethyl)-1H-indazol-5-yl]-acetamide

EXAMPLE 29A 5-nitro-1-(2-piperidin-1-yl-ethyl)-1H-indazole

A mixture of 5-nitroindazole (4.0 g, 24 mmol) and potassium carbonate (10 g 74 mmol) in DMF (60 mL) was stirred for 30 minutes after which 1-(2-chloro-ethyl)-piperidine hydrochloride (6.8 g 37 mmol) was added. The mixture was heated to 60° C. for 6 hours, cooled to room temperature and filtered through a plug of silica gel which was rinsed with triethylamine/ethyl acetate (1/4). The filtrate was concentrated under reduced pressure and purified by flash chromatography (silica gel, triethylamine/ethyl acetate 1/30) to provide the title compound (4.3 g, 64% yield). $^1$H NMR (300 MHz, DMSO-$d_6$) ppm 1.34 (m, 6H), 2.36 (m, 4H), 2.72 (t, J=6.44, 2H), 4.58 (t, J=6.44, 2H), 7.90 (m, 1H), 8.21 (m, 1H), 8.40 (m, 1H), 8.82 (m, 1H); MS (DCI/NH$_3$) m/z 275 [M+H]$^+$.

EXAMPLE 29B 1-(2-piperidin-1-yl-ethyl)-1H-indazol-5-ylamine

A mixture of 5-nitro-1-(2-piperidin-1-yl-ethyl)-1H-indazole (4.3 g, 16 mmol), iron powder (8.8 g, 157 mmol), and ammonium chloride (430 mg, 8 mmol) in a 4:1 ethanol/H$_2$O solution (75 mL) was heated to reflux for 3 hours, cooled to room temperature and concentrated under reduced pressure. The residue was stirred in triethylamine/ethyl acetate (1/4, 50 mL) for 15 minutes, filtered through a plug of silica gel which was rinsed with triethylamine/ethyl acetate (1/4). The filtrate was concentrated under reduced pressure to provide the title compound (3.4 g, 93%). $^1$H NMR (300 MHz, DMSO-$d_6$) ppm 1.34–1.45 (m, 6H), 2.36 (m, 4H), 2.64 (t, J=6.44, 2H), 4.35 (t, J=6.44, 2H), 4.76 (s, 2H), 6.71 (m, 1H), 6.79 (m, 11H), 7.35 (m, 1H), 7.67 (m, 1H); MS (DCI/NH$_3$) m/z 245 [M+H]$^+$.

EXAMPLE 29

2-(4-phenoxy-phenyl)-N-[1-(2-piperidin-1-yl-ethyl)-1H-indazol-5-yl]-acetamide

The title compound was prepared according to the procedure described in Example 27 substituting 1-(2-piperidin-1-yl-ethyl)-1H-indazol-5-ylamine for 1-(2-dimethylamino-ethyl)-1H-indazol-5-ylamine. $^1$H NMR (300 MHz, DMSO-$d_6$) ppm 1.35 (m, 1H), 1.65 (m, 3H), 1.81 (m, 2H), 2.96 (m, 2H), 3.51 (m, 2H), 3.58 (m, 2H), 3.65 (s, 2H), 4.78 (t, J=6.55, 2H), 6.98 (m, 4H), 7.13 (m, 1H), 7.38 (m, 4H), 7.55 (m, 1H), 7.69 (m, 1H), 8.12 (m, 1H), 8.15 (m, 1H), 10.23 (s, 1H); MS (DCI/NH$_3$) m/z 455 [M+H]$^+$.

EXAMPLE 30

1-(4-phenoxy-phenyl)-3-[1-(2-piperidin-1-yl-ethyl)-1H-indazol-5-yl]-urea

The title compound was prepared according to the procedure described in Example 28 substituting 1-(2-piperidin-1-yl-ethyl)-1H-indazol-5-ylamine for 1-(2-dimethylamino-ethyl)-1H-indazol-5-ylamine. $^1$H NMR (300 MHz, DMSO-$d_6$) ppm 1.38 (m, 1H), 1.65 (m, 3H), 1.81 (m, 2H), 2.95 (m, 2H), 3.56 (m, 4H), 4.78 (t, J=6.44, 2H), 6.97 (m, 4H), 7.09 (m, 1H), 7.36 (m, 2H), 7.47 (m, 3H), 7.67 (m, 1H), 7.94 (m, 1H), 8.11 (m, 1H), 8.77 (s, 2H); MS (DCI/NH$_3$) m/z 456 [M+H]$^+$.

EXAMPLE 31

N-[1-(2-morpholin-4-yl-ethyl)-1H-indazol-5-yl]-2-(4-phenoxy-phenyl)-acetamide

EXAMPLE 31A 1-(2-morpholin-4-yl-ethyl)-5-nitro-1H-indazole

A mixture of 5-nitroindazole (4 g, 24 mmol) and potassium carbonate (10.1 g 74 mmol) in DMF (60 mL) was stirred for 30 minutes, after which 1-(2-chloro-ethyl)-morpholine hydrochloride (6.8 g 37 mmol) was added. The mixture was heated to 60° C. for 6 hours, cooled to room temperature, filtered through a plug of silica gel, and rinsed with triethylamine/ethyl acetate (1/4). The filtrate was concentrated under reduced pressure and purified by flash fhromatography (silica gel, triethylamine/ethyl acetate 1/30) to provide the titled compound (4.5 g, 67% yield). $^1$H NMR (300 MHz, DMSO-$d_6$) ppm 2.41(t, J=4.74, 4H), 2.78 (t, J=6.44, 2H), 3.45 (t, J=4.74, 4H), 4.61 (t, J=6.44, 2H), 7.92 (m, 1H), 8.22 (m, 1H), 8.41 (m, 1H), 8.82 (m, 1H); MS (DCI/NH$_3$) m/z 277 [M+H]$^+$.

EXAMPLE 31B 1-(2-morpholin-4-yl-ethyl)-1H-indazol-5-ylamine

A mixture of 1-(2-morpholin-4-yl-ethyl)-5-nitro-1H-indazole (4.3 g, 16 mmol), iron powder (8.8 g, 157 mmol), and ammonium chloride (430 mg, 8 mmol) in a 4:1 ethanol/H$_2$O solution (75 mL) was heated to reflux for 3 hours, cooled to room temperature and concentrated under reduced pressure. The residue was taken up and stirred in triethylamine/ethyl acetate (1/4, 50 mL) for 15 minutes, filtered through a plug of silica gel and rinsed with triethylamine/ethyl acetate (1/4). The filtrate was concentrated under reduced pressure to provide the title compound (3.4 g, 93%). $^1$H NMR (300 MHz, DMSO-$d_6$) ppm 2.40 (t, J=4.75, 4H), 2.70 (t, J=6.78, 2H), 3.50 (t, J=4.75, 4H), 4.38 (t, J=6.78, 2H), 4.78 (s, 2H), 6.72 (m, 1H), 6.80 (m, 1H), 7.35 (m, 1H), 7.60 (m, 1H); MS (DCI/NH$_3$) m/z 247 [M+H]$^+$.

EXAMPLE 31

N-[1-(2-morpholin-4-yl-ethyl)-1H-indazol-5-yl]-2-(4-phenoxy-phenyl)-acetamide

The title compound was prepared according to the procedure described in Example 27 substituting 1-(2-morpholin-4-yl-ethyl)-1H-indazol-5-ylamine for 1-(2-dimethylamino-ethyl)-1H-indazol-5-ylamine. $^1$H NMR (300 MHz, DMSO-$d_6$) ppm 3.00–3.34 (m, 4H), 3.5–3.8 (m, 4H), 3.65 (s, 2H), 3.92 (m, 2H), 4.75 (m, 2H), 6.98 (m, 4H), 7.13 (m, 1H), 7.38 (m, 4H), 7.54 (m, 1H), 7.67 (m, 1H), 8.10 (s, 1H), 8.14 (m, 1H), 10.21 (s, 1H); MS (DCI/NH$_3$) m/z 457 [M+H]$^+$.

EXAMPLE 32

1-[1-(2-morpholin-4-yl-ethyl)-1H-indazol-5-yl]-3-(4-phenoxy-phenyl)-urea

The title compound was prepared according to the procedure described in Example 28 substituting 1-(2-morpholin-4-yl-ethyl)-1H-indazol-5-ylamine for 1-(2-dimethylamino-ethyl)-1H-indazol-5-ylamine. $^1$H NMR (300 MHz, DMSO-$d_6$) ppm 3.22 (m, 4H), 3.67 (m, 4H), 3.96 (m, 2H), 4.70 (t, J=6.44, 2H), 6.97 (m, 4H), 7.09 (m, 1H), 7.36 (m, 2H), 7.47 (m, 3H), 7.67 (m, 2H), 7.95 (m, 1H), 8.10 (m, 1H), 8.78 (s, 1H); MS (DCI/NH$_3$) m/z 458 [M+H]$^+$.

EXAMPLE 33

N-[1-(2-azepan-1-ylethyl)-1H-indazol-5-yl]-N'-(4-phenoxyphenyl)urea

EXAMPLE 33A 1-(2,2-dimethoxyethyl)-5-nitro-1H-indazole

To a stirred mixture of 3.00 g (18.4 mmol) of 5-nitroindazole and 5.08 g (36.9 mmol) of K$_2$CO$_3$ in 61 mL of DMF was slowly added 3.42 g (20.2 mmol) of 2-bromo-1,1-dimethoxy-ethane and the mixture heated to 55° C. for 12 hours. The mixture was cooled to room temperature, filtered through a bed of celite. The filtrate was evaporated to dryness and the residue purified via column chromatography (30–80% ethyl acetate/hexanes) to provide 1.08 g of the title compound. 1H NMR (300 MHz, DMSO-D6) δ ppm 3.25 (m, 6 H), 4.61 (d, J=5.43 Hz, 2 H), 4.78 (t, J=5.43 Hz, 1 H), 7.91 (m, 1 H), 8.23 (m, 1 H), 8.43 (s, 1 H), 8.82 (m, 1 H); MS (DCI/NH$_3$) m/z 252 [M+H]$^+$.

EXAMPLE 33B 1-(2,2-dimethoxyethyl)-1H-indazol-5-amine

A mixture of 1.00 g (3.98 mmol) of Example 24A, 0.105 g of NH$_4$Cl (1.98 mmol) and 2.19 g (39.2 mmol) of Fe in 34.5 mL of 80% ethanol was heated to reflux for 1 hour and cooled to room temperature and concentrated under reduced pressure. The residue was taken up in 10:1 ethyl acetate:triethylamine, filtered through a plug of silica gel, eluting with 10:1 ethyl acetate:triethylamine and the combined filtrate concentrated under reduced pressure to provide the title compound 0.900 mg. 1H NMR (300 MHz, DMSO-D6) δ ppm 3.23 (s, 6 H), 4.35 (d, J=5.43 Hz, 2 H), 4.71 (t, J=5.59 Hz, 1 H), 4.81 (s, 2 H), 6.72 (m, 1 H), 6.80 (m, 1 H), 7.35 (m, 1 H), 7.71 (m, 1 H); MS (DCI/NH$_3$) m/z 222 [M+H]$^+$.

EXAMPLE 33C

N-[1-(2,2-dimethoxyethyl)-1H-indazol-6-yl]-N'-(4-phenoxyphenyl)urea

A mixture of 0.600 g of 24B (2.71 mmol) and 0.573 g of 4-phenoxyphenyl isocyanate (2.72 mmol) in 36 mL of THF was heated to 60° C. for 1 hour, cooled to room temperature and concentrated under reduced pressure. The residue was triturated from boiling ether and filtered to provide 1.10 g of the title compound. 1H NMR (300 MHz, DMSO-D6) δ ppm 3.25 (s, 6 H), 4.46 (d, J=5.42 Hz, 2 H), 4.75 (t, J=5.42 Hz, 1 H), 6.97 (m, 4 H), 7.09 (m, 1 H), 7.35 (m, 3 H), 7.48 (m, 2 H), 7.60 (m, 1 H), 7.89 (m, 1 H), 7.99 (s, 1 H), 8.63 (s, 1 H), 8.67 (s, 1 H); MS (ESI) m/z 433 [M+H]$^+$.

EXAMPLE 33

N-[1-(2-azepan-1-ylethyl)-1H-indazol-5-yl]-N'-(4-phenoxyphenyl)urea

A mixture of example 24C (1.74 mmol) and 8 mL of 2 N HCl in 8 mL of THF was heated to 60° C. for 6 hours. The mixture was cooled to room temperature, concentrated under reduced pressure and the residue taken up in toluene concentrated three times. To a solution of 40.0 mg (0.104 mmol) of this residue, 12.9 mg (0.130 mmol) of hexamethyleneimine in 1.5 mL of 1:1 dichloroethane/methanol (1% acetic acid) was added 0.155 g of macroporous cyanoborohydride resin (2.1 mmol/g, 3 equiv). The mixture was shaken at 40° C. for 3 hours, cooled to room temperature, filtered and concentrated under vacou to provide a residue that was purified by preparative HPLC to provide the title compound. 1H NMR (300 MHz, DMSO-D6) δ ppm 1.62 (m, 4 H), 1.75 (m, 2 H), 1.81 (m, 2 H), 3.20 (m, 2 H), 3.66 (m, 4 H), 4.78 (t, J=6.78 Hz, 2 H), 6.98 (m, 4 H), 7.09 (m, 1 H), 7.37 (m, 2 H), 7.47 (m, 3 H), 7.68 (m, 1 H), 7.94 (m, 1 H), 8.11 (s, 1 H), 8.72 (m, 2 H); MS (ESI) m/z 470 [M+H]$^+$.

EXAMPLE 34

N-{1-[2-(2-methylpyrrolidin-1-yl)ethyl]-1H-indazol-5-yl}-N'-(4-phenoxyphenyl)urea The title compound was prepared according to the procedure for Example 33 substituting 2-methlypyrrolidine for hexamethyleneimine. 1H NMR (300 MHz, DMSO-D6) δ ppm 1.34 (d, J=6.44 Hz, 3 H), 1.58 (m, 1 H), 1.92 (m, 2 H), 2.19 (m, J=7.80 Hz, 1 H), 3.56 (m, 4 H), 3.86 (m, 1 H), 4.75 (t, J=6.10 Hz, 2 H), 6.97 (m, 4 H), 7.09 (m, 1 H), 7.36 (m, 2 H), 7.47 (m, 3 H), 7.68 (m, 1 H), 7.95 (m, 1 H), 8.11 (s, 1 H), 8.72 (m, 2 H); MS (ESI) m/z 456 [M+H]$^+$.

EXAMPLE 35

1-{2-[5-({[(4-phenoxyphenyl)amino]carbonyl}amino)-1H-indazol-1-yl]ethyl}piperidine-4-carboxamide The title compound was prepared according to the procedure for Example 33 substituting piperidine 4-carboxylic-acid amide for hexamethyleneimine. 1H NMR (300 MHz, DMSO-D6) δ ppm 1.76 (m, 2 H), 1.92 (m, 2 H), 2.31 (m, 1 H), 2.98 (m, 2 H), 3.60 (m, 4 H), 4.79 (m, 2 H), 6.97 (m, 5 H), 7.09 (m, 1 H), 7.38 (m, 3 H), 7.47 (m, 3 H), 7.67 (m, 1 H), 7.95 (m, 1 H), 8.10 (s, 1 H), 8.75 (s, 2 H); MS (ESI) m/z 499 [M+H]+.

EXAMPLE 36

N-(1-{2-[(2S)-2-(methoxymethyl)pyrrolidin-1-yl]ethyl}-1H-indazol-5-yl)-N'-(4-phenoxyphenyl)urea The title compound was prepared according to the procedure for Example 33 substituting (S)-2-methoxymethyl-pyrrolidine for hexamethyleneimine. 1H NMR (300 MHz, DMSO-D6) δ ppm 1.72 (m, 1 H), 1.86 (m, 1 H), 2.00 (m, 1 H), 2.12 (m, 1 H), 3.32 (s, 3 H), 3.52 (m, 3 H), 3.65 (m, 2 H), 3.80 (m, 1 H), 3.91 (m, 1 H), 4.74 (m, 2 H), 6.97 (m, 4 H), 7.09 (m, 1 H), 7.37 (m, 2 H), 7.47 (m, 3 H), 7.66 (m, 1 H), 7.94 (m, 1 H), 8.11 (s, 1 H), 8.71 (m, 2 H); MS (ESI) m/z 486 [M+H]+.

EXAMPLE 37

N-{1-[2-(4-methylpiperidin-1-yl)ethyl]-1H-indazol-5-yl}-N'-(4-phenoxyphenyl)urea The title compound was prepared according to the procedure for Example 33 substituting 4-methylpiperidine for hexamethyleneimine. 1H NMR (300 MHz, DMSO-D6) δ ppm 0.92 (d, J=6.44 Hz, 3 H), 1.33 (m, 2 H), 1.58 (m, 1 H), 1.83 (m, 2 H), 2.96 (m, 2 H), 3.48 (m, 2 H), 3.57 (m, 4 H), 6.97 (m, 4 H), 7.09 (m, 1 H), 7.36 (m, 2 H), 7.47 (m, 3 H), 7.66 (m, 1 H), 7.94 (m, 1 H), 8.09 (m, 1 H), 8.74 (m, 2 H); MS (ESI) m/z 470 [M+H]+.

EXAMPLE 38

N-{1-[2-(3-methylpiperidin-1-yl)ethyl]-1H-indazol-5-yl}-N'-(4-phenoxyphenyl)urea The title compound was prepared according to the procedure for Example 33 substituting 3-methylpiperidine for hexamethyleneimine. 1H NMR (300 MHz, DMSO-D6) δ ppm 0.89 (d, J=6.44 Hz, 3 H), 1.06 (m, 1 H), 1.70 (m, 2 H), 1.79 (m, 2 H), 2.63 (m, 1 H), 2.84 (m, 1 H), 3.57 (m, 4 H), 4.80 (t, J=6.61 Hz, 2 H), 6.97 (m, 4 H), 7.09 (m, 1 H), 7.36 (m, 2 H), 7.47 (m, 3 H), 7.67 (m, 1 H), 7.95 (m, 1 H), 8.11 (m, 1 H), 8.72 (m, 2 H); MS (ESI) m/z 470 [M+H]+.

EXAMPLE 39

N-{1-[2-(4-methylpiperazin-1-yl)ethyl]-1H-indazol-5-yl}-N'-(4-phenoxyphenyl)urea The title compound was prepared according to the procedure for Example 33 substituting 4-methylpiperazine for hexamethyleneimine. 1H NMR (300 MHz, DMSO-D6) δ ppm 2.75 (s, 3 H), 2.97 (m, 4 H), 3.12 (m, 2 H), 3.37 (m, 2 H), 4.53 (m, 4 H), 6.97 (m, 4 H), 7.09 (m, 1 H), 7.37 (m, 3 H), 7.49 (m, 2 H), 7.63 (m, 1 H), 7.88 (m, 1 H), 7.99 (s, 1 H), 8.72 (m, 2 H); MS (ESI) m/z 471 [M+H]+.

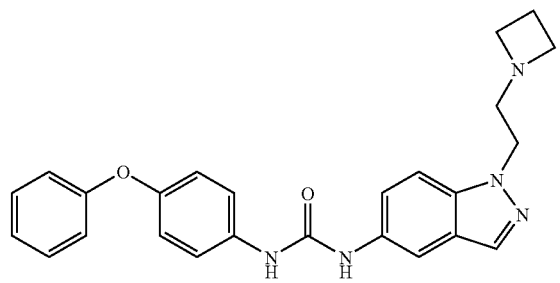

EXAMPLE 40

N-[1-(2-azetidin-1-ylethyl)-1H-indazol-5-yl]-N'-(4-phenoxyphenyl)urea

The title compound was prepared according to the procedure for Example 33 substituting azetidine for hexamethyleneimine. ¹H NMR (300 MHz, DMSO-d6) ppm 2.22 (m, 1H), 2.35 (m, 1H), 3.70 (m, 2H), 3.96 (m, 4H), 4.62 (t, 2H), 6.96 (m, 2H), 6.99 (m, 2H), 7.09 (m, 1H), 7.36 (m, 2H), 7.45 (m, 1H), 7.50 (m, 2H), 7.65 (m, 1H), 7.96 (m, 1H), 8.10 (s, 1H), 8.89 (m, 2H); MS (ESI) m/z 428 [M+H]+.

EXAMPLE 41

N-{1-[2-(diethylamino)ethyl]-1H-indazol-5-yl}-N'-(4-phenoxyphenyl)urea

The title compound was prepared according to the procedure for Example 33 substituting diethylamine for hexamethyleneimine. ¹H NMR (300 MHz, DMSO-d6) ppm 1.18 (t, 6H), 3.21 (m, 4H), 3.62 (m, 2H), 4.76 (t, 2H), 6.96 (m, 2H), 6.99 (m, 2 H), 7.09 (m, 1H), 7.36 (m, 2H), 7.47 (m, 1H), 7.49 (m, 2H), 7.69 (m, 1H), 7.95 (m, 1 H), 8.11 (s, 1H), 8.75 (m, 2H); MS (ESI) m/z 444 [M+H]+.

EXAMPLE 42

N-{1-[2-(2-methylpiperidin-1-yl)ethyl]-1H-indazol-5-yl}-N'-(4-phenoxyphenyl)urea The title compound was prepared according to the procedure for Example 33 substituting 2-methyl-piperidine for hexamethyleneimine. ¹H NMR (300 MHz, pyridine-d5) ppm 1.61 (m, 5H), 1.90 (m, 4H), 2.73 (m, 1H), 2.93 (m, 1H), 3.05 (m, 1H), 4.19 (m, 2H), 4.80 (t, 2H), 7.07 (m, 2H), 7.11 (m, 2 H), 7.33 (m, 2H), 7.53 (m, 1H), 7.74 (m, 2H), 7.84 (m, 1H), 7.98 (m, 1 H), 8.13 (m, 1H), 8.56 (s, 1H), 8.73 (m, 2H); MS (ESI) m/z 470 [M+H]+.

EXAMPLE 43

N-(1-{2-[isobutyl(methyl)amino]ethyl}-1H-indazol-5-yl)-N'-(4-phenoxyphenyl)urea

The title compound was prepared according to the procedure for Example 33 substituting isobutyl-methyl-amine for hexamethyleneimine. $^1$H NMR (300 MHz, DMSO-d6) ppm 0.92 (d, 6H), 2.05 (m, 1H), 2.85 (s, 3H), 2.94 (m, 1H), 2.96 (m, 1H), 3.61 (m, 2H), 4.81 (t, 2H), 6.96 (m, 2H), 6.99 (m, 2 H), 7.09 (m, 1H), 7.36 (m, 2H), 7.47 (m, 1H), 7.49 (m, 2H), 7.69 (m, 1H), 7.95 (m, 1 H), 8.11 (s, 1H), 8.81 (m, 2H); MS (ESI) m/z 458 [M+H]$^+$.

EXAMPLE 44

N-(1-{2-[(2S)-2-(hydroxymethyl)pyrrolidin-1-yl]ethyl}-1H-indazol-5-yl)-N'-(4-phenoxyphenyl)urea The title compound was prepared according to the procedure for Example 33 substituting (S)-pyrrolidin-2-yl-methanol for hexamethyleneimine. $^1$H NMR (300 MHz, DMSO-d6) ppm 1.73 (m, 1H), 1.85 (m, 1H), 1.97 (m, 1H), 2.07 (m, 1H), 3.10 (m, 1H), 3.53 (m, 2H), 3.63 (m, 2H), 3.90 (m, 2H), 4.78 (m, 2H), 6.96 (d, 2H), 6.99 (m, 2 H), 7.09 (m, 1H), 7.36 (m, 2H), 7.47 (m, 1H), 7.49 (m, 2H), 7.66 (m, 1H), 7.95 (m, 1 H), 8.10 (s, 1H), 8.82 (m, 2H); MS (ESI) m/z 472 [M+H]$^+$.

EXAMPLE 45

N-{1-[2-(2,3-dihydro-1H-indol-1-yl)ethyl]-1H-indazol-5-yl}-N'-(4-phenoxyphenyl)urea The title compound was prepared according to the procedure for Example 33 substituting 2,3-dihydro-1H-indole for hexamethyleneimine. $^1$H NMR (300 MHz, DMSO-d6) ppm 1.92 (m, 1H), 2.09 (m, 1H), 2.78 (m, 1H), 3.26 (m, 2H), 3.98 (m, 1H), 4.81 (m, 2H), 7.09 (m, 6H), 7.11 (m, 2 H), 7.34 (m, 2H), 7.63 (m, 1H), 7.91 (m, 1 H), 8.05 (m, 4H), 8.53 (s, 1H), 8.73 (m, 2H); MS (ESI) m/z 490 [M+H]$^+$.

EXAMPLE 46

N-(1-{2-[isopropyl(methyl)amino]ethyl}-1H-indazol-5-yl)-N'-(4-phenoxyphenyl)urea The title compound was prepared according to the procedure for Example 33 substituting isopropyl-methyl-amine for hexamethyleneimine. $^1$H NMR (300 MHz, DMSO-d6) ppm 1.20 (d, 3H), 1.25 (d, 3H), 2.50 (s, 3H), 2.76 (d, 1H), 3.66 (m, 2H), 4.77 (t, 2H), 6.96 (d, 2H), 6.99 (m, 2 H), 7.09 (m, 1H), 7.36 (m, 2H), 7.47 (m, 1H), 7.50 (m, 2H), 7.69 (m, 1H), 7.96 (m, 1H), 8.11 (s, 1H), 8.87 (m, 2H); MS (ESI) m/z 444 [M+H]$^+$.

EXAMPLE 47

N-((3R)-1-{2-[5-({[(4-phenoxyphenyl)amino]carbonyl}amino)-1H-indazol-1-yl]ethyl}pyrrolidin-3-yl)acetamide The title compound was prepared according to the procedure for Example 33 substituting (R)-N-pyrrolidin-3-yl-acetamide for hexamethyleneimine. $^1$H NMR (300 MHz, DMSO-d6) ppm 1.87 (m, 1H), 2.01 (s, 3H), 2.22 (m, 1H), 2.69 (m, 1H), 3.14 (m, 2H), 3.20 (m, 2H), 3.37 (m, 2H), 4.70 (m, 2H), 7.09 (m, 4H), 7.33 (m, 2H), 7.55 (m, 1H), 7.92 (m, 1H), 8.05 (m, 3H), 8.53 (s, 1H), 8.73 (m, 2H), 8.76 (d, 1H); MS (ESI) m/z 499 [M+H]$^+$.

EXAMPLE 48

N-{1-[2-(3-hydroxypyrrolidin-1-yl)ethyl]-1H-indazol-5-yl}-N'-(4-phenoxyphenyl)urea The title compound was prepared according to the procedure for Example 33 substituting pyrrolidin-3-ol for hexamethyleneimine. $^1$H NMR (300 MHz, DMSO-d6) ppm 1.80 (m, 1H), 1.92 (m, 1H), 2.22 (m, 1H), 3.08 (m, 2H), 3.55 (m, 2H), 3.68 (m, 2H), 4.76 (m, 2H), 5.50 (s, 1H), 6.96 (d, 2H), 6.99 (m, 2 H), 7.09 (m, 1H), 7.36 (m, 2H), 7.47 (m, 1H), 7.50 (m, 2H), 7.66 (m, 1H), 7.96 (m, 1H), 8.10 (s, 1H), 8.89 (m, 2H); MS (ESI) m/z 458 [M+H]$^+$.

EXAMPLE 49

2-[4-(benzyloxy)phenyl]-N-[1-(2-pyrrolidin-1-yl-ethyl)-1H-indazol-6-yl]acetamide

EXAMPLE 49A 6-nitro-1-(2-pyrrolidin-1-yl-ethyl)-1H-indazole

A mixture of 6-nitroindazole (2.00 g, 12.3 mmol) and potassium carbonate (5.10 g 37.0 mmol) in DMF (40 mL) was stirred for 30 minutes, after which 1-(2-chloro-ethyl)-pyrrolidine hydrochloride (3.20 g 18.9 mmol) was added. The mixture was heated to 60° C. for 6 hours, cooled to room temperature, filtered through a plug of silica gel and rinsed with triethylamine/ethyl acetate (1/4). The filtrate was concentrated under reduced pressure and purified by flash chromatography (silica gel, triethylamine/ethyl acetate 1/30) to provide the title compound. $^1$H NMR (300 MHz, DMSO-d$_6$) δ ppm 1.61 (m, 4H), 2.47 (m, 4H), 2.90 (t, 2H, J=6.45), 4.68 (t, 2H, J=6.44), 7.94 (m, 1H), 8.00 (m, 1H), 8.31 (s, 1H), 8.77 (s, 1H); MS (DCI/NH$_3$) m/z 261 [M+H]$^+$.

EXAMPLE 49B 1-(2-pyrrolidin-1-yl-ethyl)-1H-indazol-6-ylamine

A mixture of 6-nitro-1-(2-pyrrolidin-1-yl-ethyl)-1H-indazole (1.60 g, 6.15 mmol), iron powder (3.40 g, 60.8 mmol), and ammonium chloride (166 mg, 3.13 mmol) in a 4:1 solution of ethanol/H$_2$O was heated to reflux for 3 hours, cooled to room temperature, concentrated under reduced pressure. The residue was stirred in triethylamine/ethyl acetate (1/4, 30 mL) for 15 minutes, filtered through a plug of silica gel which was rinsed with triethylamine/ethyl acetate (1/4), and the filtrate was concentrated under reduced pressure to provide the title compound. $^1$H NMR (300 MHz, DMSO-d$_6$) δ ppm 1.66 (m, 4H), 2.50 (m, 4H), 2.85 (t, 2H, J=6.78), 4.27 (t, 2H, J=6.78), 5.30 (s, 2H), 6.49 (m, 2H), 7.35 (m, 1H), 7.70 (m, 1H); MS (DCI/NH$_3$) m/z 231 [M+H]$^+$.

EXAMPLE 49

2-[4-(benzyloxy)phenyl]-N-[1-(2-pyrrolidin-1-yl-ethyl)-1H-indazol-6-yl]acetamide A mixture of 1-(2-pyrrolidin-1-yl-ethyl)-1H-indazol-6-ylamine (48 mg, 0.21 mmol), (4-benzyloxy-phenyl)-acetic acid (50 mg, 0.21 mmol), ethyldimethylpropylcarbodiimide hydrochloride (47 mg g, 0.25 mmol), N-hydroxybenzotriazole (33 mg, 0.25 mmol), N-methyl morpholine (50 mg, 0.50 mmol) in 2 mL of DMF was shaken for 6 hours. The mixture was concentrated under reduced pressure, the residue was dissolved in 1.5 mL of a 1:1 mixture of dimethyl sulfoxide/methanol and purified by preparative reverse-phase HPLC. $^1$H NMR (300 MHz, DMSO-$d_6$) δ ppm 1.62 (m, 4H), 2.44 (m, 4H), 2.82 (t, 2H, J=6.78), 3.60 (s, 2H), 4.38 (t, 2H, J=6.78), 5.09 (s, 2H), 6.97 (m, 2H), 7.11–7.45 (m, 8H), 7.65 (m, 1H), 7.93 (m, 1H), 8.12 (s, 1H), 10.27 (s, 1H); MS (DCI/NH$_3$) m/z 455 [M+H]$^+$.

EXAMPLE 50

2-(3-phenoxyphenyl)-N-[1-(2-pyrrolidin-1-ylethyl)-1H-indazol-6-yl]acetamide

According to the procedure for Example 49, 1-(2-pyrrolidin-1-yl-ethyl)-1H-indazol-6-ylamine and (3-phenoxyphenyl)-acetic acid were processed to provide the title compound. $^1$H NMR (500 MHz, DMSO-$d_6$) δ ppm 1.82 (m, 2 H), 1.99 (m, 2 H), 3.03 (m, 2 H), 3.51 (m, 2 H), 3.68 (m, 4 H), 4.66 (t, J=6.24 Hz, 2 H), 6.89 (m, 1 H), 7.03 (m, 3 H), 7.12 (m, 3 H), 7.37 (m, 3 H), 7.72 (m, 1 H), 8.08 (s, 1 H), 8.26 (s, 1 H), 9.55 (br s, N H); MS (DCI/NH$_3$) m/z 441 (M+H)$^+$.

EXAMPLE 51

4-(1,1'-biphenyl-4-yl)-4-oxo-N-[1-(2-pyrrolidin-1-ylethyl)-1H-indazol-6-yl]butanamide According to the procedure for Example 49, 1-(2-pyrrolidin-1-yl-ethyl)-1H-indazol-6-ylamine and 4-biphenyl-4-yl-4-oxo-butyric acid were processed to provide the title compound. $^1$H NMR (500 MHz, DMSO-$d_6$) δ ppm 1.80 (m, 2 H), 1.97 (m, 2 H), 2.83 (t, J=6.10 Hz, 2 H), 3.02 (m, 2 H), 3.41 (t, J=6.26 Hz, 2 H), 3.50 (m, 2 H), 3.69 (m, 2 H), 4.66 (t, J=6.26 Hz, 2 H), 7.11 (m, 1 H), 7.45 (m, 1 H), 7.52 (m, 2 H), 7.72 (m, 1 H), 7.77 (m, 2 H), 7.86 (m, 2 H), 8.10 (m, 3 H), 8.29 (s, 1 H), 9.56 (br s, N H); MS (DCI/NH$_3$) m/z 467 (M+H)$^+$.

EXAMPLE 52

3-(2-naphthylthio)-N-[1-(2-pyrrolidin-1-ylethyl)-1H-indazol-6-yl]propanamide

According to the procedure for Example 49, 1-(2-pyrrolidin-1-yl-ethyl)-1H-indazol-6-ylamine and 3-(naphthalen-2-ylsulfanyl)-propionic acid were processed to provide the title compound. $^1$H NMR (500 MHz, DMSO-$d_6$) δ ppm 1.84 (m, 2 H), 1.99 (m, 2 H), 2.79 (t, J=7.02 Hz, 2 H), 3.04 (m, 2 H), 3.40 (t, J=7.02 Hz, 2 H), 3.53 (m, 2 H), 3.71 (q, J=6.10 Hz, 2 H), 4.68 (t, J=6.26 Hz, 2 H), 7.06 (m, 1 H), 7.50 (m, 3 H), 7.70 (m, 1 H), 7.88 (m, 4 H), 8.09 (s, 1 H), 8.30 (s, 1 H), 9.62 (br s, N H); MS (DCI/NH$_3$) m/z 445 (M+H)$^+$.

EXAMPLE 53

2-(5-{[(4-methylphenyl)thio]acetyl}thien-2-yl)-N-[1-(2-pyrrolidin-1-ylethyl)-1H-indazol-6-yl]acetamide According to the procedure for Example 49, 1-(2-pyrrolidin-1-yl-ethyl)-1H-indazol-6-ylamine and [5-(2-p-tolylsulfanyl-acetyl)-thiophen-2-yl]-acetic acid were processed to provide the title compound. $^1$H NMR (500 MHz, DMSO-$d_6$) δ ppm 1.82 (m, 2 H), 1.98 (m, 2 H), 2.25 (s, 3 H), 3.02 (m, 2 H), 3.52 (m, 2 H), 3.70 (q, J=5.80 Hz, 2 H), 4.05 (s, 2 H), 4.41 (s, 2 H), 4.68 (t, J=6.26 Hz, 2 H), 7.12 (m, 4 H), 7.26 (m, 2 H), 7.74 (m, 1 H), 7.94 (m, 1 H), 8.11 (s, 1 H), 8.27 (s, 1 H), 9.56 (br s, N H); MS (DCI/NH$_3$) m/z 519 (M+H)$^+$.

EXAMPLE 54

3-(4-phenoxyphenyl)-N-[1-(2-pyrrolidin-1-ylethyl)-1H-indazol-6-yl]propanamide

According to the procedure for Example 49, 1-(2-pyrrolidin-1-yl-ethyl)-1H-indazol-6-ylamine and 3-(4-phenoxyphenyl)-propionic acid were processed to provide the title compound. MS (DCI/NH$_3$) MS m/z 455 (M+H)$^+$; $^1$H NMR (500 MHz, DMSO-$d_6$) δ ppm 1.84 (m, 2 H), 2.00 (m, 2 H), 2.70 (t, J=7.64 Hz, 2 H), 2.94 (t, J=7.64 Hz, 2 H), 3.05 (m, 2 H), 3.53 (m, 2 H), 3.71 (q, J=5.82 Hz, 2 H), 4.68 (t, J=6.24 Hz, 2 H), 6.95 (m, 4 H), 7.09 (m, 2 H), 7.29 (m, 2 H), 7.36 (m, 2 H), 7.70 (m, 1 H), 8.08 (s, 1 H), 8.28 (s, 1 H), 9.62 (br s, N H).

EXAMPLE 55

3-[5-(4-methylphenyl)-1,3-oxazol-2-yl]-N-[1-(2-pyrrolidin-1-ylethyl)-1H-indazol-6-yl]propanamide According to the procedure for Example 49, 1-(2-pyrrolidin-1-yl-ethyl)-1H-indazol-6-ylamine and 3-(5-p-tolyl-oxazol-2-yl)-propionic acid were processed to provide the title compound. MS (DCI/NH$_3$) MS m/z 444 (M+H)$^+$. $^1$H NMR (500 MHz, DMSO-$d_6$) δ ppm 1.82 (m, 2 H), 1.98 (m, 2 H), 2.32 (s, 3 H), 2.93 (t, J=7.02 Hz, 2 H), 3.03 (m, 2 H), 3.15 (t, J=7.02 Hz, 2 H), 3.52 (m, 2 H), 3.69 (q, J=5.93 Hz, 2 H), 4.67 (t, J=6.24 Hz, 2 H), 7.10 (m, 1 H), 7.25 (m, 2 H), 7.47 (s, 1 H), 7.55 (m, 2 H), 7.71 (m, 1 H), 8.08 (s, 1 H), 8.31 (s, 1 H), 9.60 (br s, N H).

EXAMPLE 56

2-[4-(benzyloxy)-3-methoxyphenyl]-N-[1-(2-pyrrolidin-1-ylethyl)-1H-indazol-6-yl]acetamide According to the procedure for Example 49, 1-(2-pyrrolidin-1-yl-ethyl)-1H-indazol-6-ylamine and (4-benzyloxy-3-methoxy-phenyl)-acetic acid were processed to provide the title compound. MS (DCI/NH$_3$) MS m/z 485 (M+H)$^+$. $^1$H NMR (500 MHz, DMSO-$d_6$) δ ppm 1.81 (m, 2 H), 1.97 (m, 2 H), 3.02 (m, 2 H), 3.51 (m, 2 H), 3.62 (s, 2 H), 3.69 (q, J=5.82 Hz, 2 H), 3.78 (s, 3 H), 4.66 (t, J=6.24 Hz, 2 H), 5.06 (s, 2 H), 6.84 (m, 1 H), 6.99 (m, 2 H), 7.12 (m, 1 H), 7.32 (m, 1 H), 7.40 (m, 4 H), 7.71 (m, 1 H), 8.08 (s, 1 H), 8.27 (s, 1 H), 9.59 (br s, N H).

EXAMPLE 57

3-[4-(benzyloxy)-3-methoxyphenyl]-N-[1-(2-pyrrolidin-1-ylethyl)-1H-indazol-6-yl]propanamide

EXAMPLE 57A (2E)-3-[4-(benzyloxy)-3-methoxyphenyl]-N-[1-(2-pyrrolidin-1-ylethyl)-1H-indazol-6-yl]acrylamide According to the procedure for Example 49, 1-(2-pyrrolidin-1-yl-ethyl)-1H-indazol-6-ylamine and 3-(4-benzyloxy-3-methoxy-phenyl)-acrylic acid were processed to provide the title compound. MS (DCI/NH$_3$) MS m/z 497 (M+H)$^+$; $^1$H NMR (500 MHz, DMSO-$d_6$) δ ppm 1.85 (m, 2 H), 2.01 (m, 2 H), 3.06 (m, 2 H), 3.55 (m, 2 H), 3.71 (m, 2H), 3.85 (s, 3 H), 4.71 (t, J=6.24 Hz, 2 H), 5.15 (s, 2 H), 6.79 (m, 1

H), 7.12 (m, 1 H), 7.18 (m, 2 H), 7.26 (m, 1 H), 7.35 (m, 1 H), 7.41 (m, 2 H), 7.46 (m, 2 H), 7.55 (m, 1 H), 7.74 (m, 1 H), 8.10 (s, 1 H), 8.41 (s, 1 H), 9.63 (br s, N H).

EXAMPLE 57

3-[4-(benzyloxy)-3-methoxyphenyl]-N-[1-(2-pyrrolidin-1-ylethyl)-1H-indazol-6-yl]propanamide A mixture of Example 57A (0.0373 g; 0.0750 mmol) and 10% of Pd/C (10 mg) in methanol (2 mL) was stirred under 60 psi of $H_2$ at room temperature for 42 hours. The mixture was filtered and concentrated under reduced pressure and the oil was purified by reverse phase HPLC to provide the title compound. MS (DCI/$NH_3$) MS m/z 499 (M+H)$^+$; $^1$H NMR (500 MHz, DMSO-$d_6$) δ ppm 1.84 (m, 2 H), 2.00 (m, 2 H), 2.67 (t, J=7.64 Hz, 2H), 2.89 (t, J=7.64 Hz, 2 H), 3.05 (m, 2 H), 3.53 (m, 2 H), 3.71 (m, 2 H), 3.75 (s, 3 H), 4.68 (t, J=6.08 Hz, 2 H), 5.03 (s, 2 H), 6.75 (m, 1 H), 6.91 (m, 2 H), 7.09 (m, 1 H), 7.31 (m, 1 H), 7.39 (m, 4 H), 7.70 (m, 1 H), 8.08 (s, 1 H), 8.28 (s, 1 H), 9.62 (br s, N H).

EXAMPLE 58

2-(4-phenoxyphenyl)-N-[1-(2-pyrrolidin-1-ylethyl)-1H-indazol-6-yl]acetamide

According to the procedure for Example 49, 1-(2-pyrrolidin-1-yl-ethyl)-1H-indazol-6-ylamine and (4-phenoxyphenyl)-acetic acid were processed to provide the title compound. 1H NMR (500 MHz, DMSO-D6) δ ppm 1.82 (m, 2 H), 1.98 (m, 2 H), 3.03 (m, 2 H), 3.52 (m, 2 H), 3.69 (m, 4 H), 4.67 (t, J=6.24 Hz, 2 H), 6.99 (m, 4 H), 7.13 (m, 2 H), 7.38 (m, 4 H), 7.72 (m, 1 H), 8.08 (m, 1 H), 8.29 (s, 1 H), 10.42 (s, 1 H); MS (DCI/$NH_3$) m/z 441 (M+H)$^+$.

EXAMPLE 59

3-[4-(benzyloxy)phenyl]-N-[1-(2-pyrrolidin-1-ylethyl)-1H-indazol-6-yl]propanamide According to the procedure for Example 49, 1-(2-pyrrolidin-1-yl-ethyl)-1H-indazol-6-ylamine and 3-(4-benzyloxyphenyl)-propionic acid were processed to provide the title compound. 1H NMR (500 MHz, DMSO-D6) δ ppm 1.83 (m, 2 H), 2.00 (m, 2 H), 2.66 (t, J=7.64 Hz, 2 H), 2.88 (t, J=7.49 Hz, 2 H), 3.05 (dd, J=10.45, 7.33 Hz, 2 H), 3.53 (m, 2 H), 3.69 (m, 2 H), 4.67 (t, J=6.24 Hz, 2 H), 5.06 (s, 2 H), 6.93 (m, 2 H), 7.07 (m, 1 H), 7.18 (m, 2 H), 7.32 (m, 1 H), 7.40 (m, 4 H), 7.70 (m, 1 H), 8.08 (m, 1 H), 8.28 (s, 1 H), 10.13 (s, 1 H); MS (DCI/$NH_3$) m/z 469 (M+H)$^+$;

EXAMPLE 60

3-(4-phenoxypyridin-3-yl)-N-[1-(2-pyrrolidin-1-ylethyl)-1H-indazol-6-yl]propanamide

EXAMPLE 60A (2E)-3-(4-phenoxypyridin-3-yl)-N-[1-(2-pyrrolidin-1-ylethyl)-1H-indazol-6-yl]acrylamide According to the procedure for Example 49, 1-(2-pyrrolidin-1-yl-ethyl)-1H-indazol-6-ylamine and 3-(4-phenoxypyridin-3-yl)-acrylic acid were processed to provide the title compound. MS (DCI/$NH_3$) MS m/z 454 (M+H)$^+$; $^1$H NMR (500 MHz, DMSO-$d_6$) δ ppm 1.84 (m, 2 H), 2.01 (m, 2 H), 3.07 (m, 2 H), 3.54 (m, 2 H), 3.73 (m, 2 H), 4.71 (t, J=6.08 Hz, 2 H), 6.88 (m, 1 H), 7.20 (m, 5 H), 7.45 (m, 2 H), 7.62 (m, 1 H), 7.75 (m, 1 H), 8.13 (m, 2 H), 8.40 (m, 2 H), 9.62 (br s, N H).

EXAMPLE 60

3-(4-phenoxypyridin-3-yl)-N-[1-(2-pyrrolidin-1-ylethyl)-1H-indazol-6-yl]propanamide According to procedure described in Example 57, Example 60A was processed to provide the title compound. MS (DCI/$NH_3$) MS m/z 456 (M+H)$^+$; $^1$H NMR (500 MHz, DMSO-$d_6$) δ ppm 1.83 (m, 2 H), 1.99 (m, 2 H), 2.71 (t, J=7.49 Hz, 2 H), 2.93 (t, J=7.33 Hz, 2 H), 3.05 (m, 2 H), 3.53 (m, 2 H), 3.71 (m, 2 H), 4.67 (t, J=6.24 Hz, 2 H), 6.96 (m, 1 H), 7.07 (m, 3 H), 7.18 (m, 1 H), 7.39 (m, 2 H), 7.70 (m, 1 H), 7.77 (m, 1 H), 8.06 (m, 2 H), 8.26 (s, 1 H), 9.63 (br s, N H).

EXAMPLE 61

2-{4-[(4-fluorobenzyl)oxy]phenyl}-N-[1-(2-pyrrolidin-1-ylethyl)-1H-indazol-6-yl]acetamide

EXAMPLE 61A 2-(4-hydroxy-phenyl)-N-[1-(2-pyrrolidin-1-yl-ethyl)-1H-indazol-6-yl]-acetamide A mixture of 1-(2-pyrrolidin-1-yl-ethyl)-1H-indazol-6-ylamine (0.620 g, 2.69 mmol), (4-hydroxy-phenyl)-acetic acid (0.242 g, 5.15 mmol), HATU (1.23 g, 3.23 mmol) and diisopropylethylamine (0.939 mL, 5.39 mmol) in 9 mL of DMF was stirred at room temperature for 6 hours, concentrated under reduced pressure and the residue dissolved in ethyl acetate and washed with aqueous $NaHCO_3$ (×3), brine (×2), and water. The organic layer was dried ($Na_2SO_4$), filtered, concentrated under reduced pressure and the residue purified by flash chromatography (60–90% ethyl acetate (1% triethylamine) in hexanes) to provide the title compound. 1H NMR (300 MHz, DMSO-D6) δ ppm 1.62 (m, 4 H), 2.45 (m, 4 H), 2.83 (t, J=6.78 Hz, 2 H), 3.53 (d, J=5.76 Hz, 2 H), 4.38 (t, J=6.78 Hz, 2 H), 6.71 (m, 2 H), 7.13 (m, 3 H), 7.64 (m, 1 H), 7.94 (s, 1 H), 8.13 (m, 1 H), 9.25 (s, 1 H), 10.24 (s, 1 H); MS (ESI) m/z 365 [M+H]$^+$.

EXAMPLE 61

2-{4-[(4-fluorobenzyl)oxy]phenyl}-N-[1-(2-pyrrolidin-1-ylethyl)-1H-indazol-6-yl]acetamide A mixture of 2-(4-hydroxy-phenyl)-N-[1-(2-pyrrolidin-1-yl-ethyl)-1H-indazol-6-yl]-acetamide (45.0 mg, 0.124 mmol), 1-bromomethyl-4-fluoro-benzene (35.0 mg, 0.185 mmol), $Cs_2CO_3$ (60.0 mg, 0.184 mmol) in 2 mL of DMF was shaken for 6 hours and concentrated under reduced pressure. The residue was dissolved in a 1:1 mixture of dimethyl sulfoxide/MeOH (1.5 mL) and purified by preparative reverse-phase HPLC. 1H NMR (500 MHz, DMSO-D6) δ ppm 1.82 (m, 2 H), 1.98 (m, J=7.02, 7.02 Hz, 2 H), 3.02 (m, 2 H), 3.48 (m, 2 H), 3.68 (m, 4 H), 4.65 (t, J=6.24 Hz, 2 H), 5.07 (s, 2 H), 6.97 (m, 2 H), 7.11 (m, 1 H), 7.21 (m, 2 H), 7.27 (m, 2 H), 7.48 (m, 2 H), 7.71 (m, 1 H), 8.08 (s, 1 H), 8.26 (s, 1 H), 10.35 (s, 1 H); MS (ESI) m/z 473 [M+H]$^+$.

EXAMPLE 62

2-{4-[(3-fluorobenzyl)oxy]phenyl}-N-[1-(2-pyrrolidin-1-ylethyl)-1H-indazol-6-yl]acetamide The title compound was prepared according to the procedure for Example 61 substituting 1-bromomethyl-3-fluoro-benzene for 1-bromomethyl-4-fluoro-benzene. 1H NMR (500 MHz, DMSO-D6) δ ppm 1.82 (m, 2 H), 1.98 (m, J=6.71, 6.71 Hz, 2 H), 3.02 (m, J=10.29, 7.17 Hz, 2 H), 3.51 (m, J=4.68 Hz, 2 H), 3.62 (s, 2 H), 3.69 (m, 2 H), 4.66 (t, J=6.24 Hz, 2 H), 5.12 (s, 2 H), 6.98 (m, 2 H), 7.13 (m, 2 H), 7.26 (m, 4 H), 7.43 (m, 1 H), 7.71 (m, 1 H), 8.08 (m, 1 H), 8.26 (s, 1 H), 10.35 (s, 1 H); MS (ESI) m/z 473 [M+H]$^+$.

EXAMPLE 63

2-(4-{[4-(difluoromethoxy)benzyl]oxy}phenyl)-N-[1-(2-pyrrolidin-1-ylethyl)-1H-indazol-6-yl]acetamide The title compound was prepared according to the procedure for Example 61 substituting 1-bromomethyl-4-difluoromethoxy-benzene for 1-bromomethyl-4-fluoro-benzene. 1H NMR (500 MHz, DMSO-D6) δ ppm 1.82 (m, 2 H), 1.98 (m, J=7.17, 7.17 Hz, 2 H), 3.02 (m, 2 H), 3.51 (m, 3 H), 3.62 (s, 2 H), 3.69 (m, 2 H), 4.65 (t, J=6.24 Hz, 2 H), 5.09 (s, 2 H), 6.97 (m, 2 H), 7.10 (m, 1 H), 7.19 (m, 2 H), 7.27 (m, 2 H), 7.49 (m, 2 H), 7.71 (m, 1 H), 8.08 (m, 1 H), 8.26 (s, 1 H), 10.34 (s, 1 H); MS (ESI) m/z 521 [M+H]$^+$.

EXAMPLE 64

2-{4-[(3,5-dichlorobenzyl)oxy]phenyl}-N-[1-(2-pyrrolidin-1-ylethyl)-1H-indazol-6-yl]acetamide The title compound was prepared according to the procedure for Example 61 substituting 1-bromomethyl-3,5-dichloro-benzene for 1-bromomethyl-4-fluoro-benzene. 1H NMR (300 MHz, DMSO-D6) δ ppm 1.81 (m, 2 H), 1.97 (m, 2 H), 3.02 (m, 2 H), 3.51 (m, 2 H), 3.63 (s, 2 H), 3.68 (m, J=5.76 Hz, 2 H), 4.64 (m, J=6.10 Hz, 2 H), 5.13 (s, 2 H), 6.98 (m, 2 H), 7.10 (m, 1 H), 7.28 (m, 2 H), 7.49 (m, 2 H), 7.57 (m, 1 H), 7.71 (m, 1 H), 8.08 (m, 1 H), 8.28 (s, 1 H), 10.36 (s, 1 H); MS (ESI) m/z 523 [M+H]$^+$.

EXAMPLE 65

2-{4-[(3-cyanobenzyl)oxy]phenyl}-N-[1-(2-pyrrolidin-1-ylethyl)-1H-indazol-6-yl]acetamide The title compound was prepared according to the procedure for Example 61 substituting 1-bromomethyl-3-cyano-benzene for 1-bromomethyl-4-fluoro-benzene. 1H NMR (500 MHz, DMSO-D6) δ ppm 1.62 (m, 4 H), 2.44 (m, 4 H), 2.83 (t, J=6.86 Hz, 2 H), 3.61 (s, 2 H), 4.38 (t, J=6.86 Hz, 2 H), 5.16 (s, 2 H), 6.99 (m, 2 H), 7.14 (m, 1 H), 7.28 (m, 2 H), 7.62 (m, 2 H), 7.78 (m, 2 H), 7.92 (m, 2 H), 8.12 (s, 1 H), 10.27 (s, 1 H); MS (ESI) m/z 480 [M+H]$^+$.

EXAMPLE 66

N-[2-(4-phenoxyphenyl)ethyl]-N'-[1-(2-pyrrolidin-1-ylethyl)-1H-indazol-6-yl]urea

EXAMPLE 66A phenyl 1-(2-pyrrolidin-1-ylethyl)-1H-indazol-6-ylcarbamate

To a mixture of 1-(2-pyrrolidin-1-yl-ethyl)-1H-indazol-6-ylamine (0.220 g, 0.955 mmol) and triethylamine (0.240 mL, 1.72 mmol) in 1 mL of THF at 0 C was slowly added phenyl chloroformate (0.246 ml, 1.72 mmol). The mixture was stirred cold for 1 hours and the formed precipitate collected by filtration with rinsing with ether to provide the title compound. 1H NMR (300 MHz, DMSO-D6) δ ppm 1.82 (m, 2 H), 1.97 (m, 2 H), 2.97 (m, 2 H), 3.49 (m, 2 H), 3.69 (m, 2 H), 4.71 (t, J=6.27 Hz, 2 H), 7.19 (m, 1 H), 7.28 (m, 3 H), 7.46 (m, 2 H), 7.74 (m, 1 H), 7.99 (m, 1 H), 8.10 (s, 1 H), 10.51 (s, 1 H); MS (DCI/NH$_3$) m/z 351 [M+H]$^+$.

EXAMPLE 66

N-[2-(4-phenoxyphenyl)ethyl]-N'-[1-(2-pyrrolidin-1-ylethyl)-1H-indazol-6-yl]urea A mixture of example 66A (30.0 mg, 0.086 mmol), NMP (0.8 mL), triethylamine (0.0143 mL, 0.103 mmol), and 2-(4-phenoxy-phenyl)-ethylamine (0.0220 g, 0.103 mmol) in a sealed vessel was heated to 200° C. for 20 minutes. The mixture was cooled to room temperature, concentrated under reduced pressure and the residue dissolved in a 1:1 solution of methanol/dimethyl sulfoxide and purified by reverse-phase preparative HPLC to provide the title compound. 1H NMR (300 MHz, DMSO-D6) δ ppm 1.83 (m, 2 H), 1.99 (m, 2 H), 2.75 (t, J=7.29 Hz, 2 H), 3.04 (m, 2 H), 3.35 (m, 2 H), 3.69 (m, 4 H), 4.71 (t, J=6.10 Hz, 2 H), 6.12 (t, J=5.76 Hz, 1 H), 6.97 (m, 4 H), 7.12 (m, 1 H), 7.26 (m, 2 H), 7.38 (m, 3 H), 7.60 (m, 1 H), 7.88 (m, 1 H), 8.05 (m, 1 H), 8.50 (m, 1 H); MS (ESI) m/z 470 [M+H]$^+$.

EXAMPLE 67

N-(4-phenoxybenzyl)-N'-[1-(2-pyrrolidin-1-ylethyl)-1H-indazol-6-yl]urea

The title compound was prepared according to the procedure for Example 66 substituting 4-phenoxy-benzylamine for 2-(4-phenoxy-phenyl)-ethylamine. 1H NMR (300 MHz, DMSO-D6) δ ppm 1.82 (m, 2 H), 1.99 (m, 2 H), 3.04 (m, 2 H), 3.35 (m, 2 H), 3.71 (m, 2 H), 4.32 (d, J=5.76 Hz, 2 H), 4.64 (t, J=6.27 Hz, 2 H), 6.78 (m, 1 H), 6.90 (m, 1 H), 7.00 (m, 4 H), 7.12 (m, 1 H), 7.36 (m, 4 H), 8.04 (m, 1 H), 8.04 (m, 2 H), 8.86 (s, 1 H); MS (ESI) m/z 456 [M+H]$^+$.

EXAMPLE 68

N-[4-(benzyloxy)phenyl]-N'-[1-(2-pyrrolidin-1-ylethyl)-1H-indazol-6-yl]urea

The title compound was prepared according to the procedure for Example 66 substituting 4-benzyloxy-phenylamine for 2-(4-phenoxy-phenyl)-ethylamine. 1H NMR (500 MHz, DMSO-D6) δ ppm 1.84 (m, 2 H), 1.99 (m, 2 H), 3.04 (m, 2 H), 3.52 (m, 2 H), 3.70 (m, 2 H), 4.67 (t, J=6.08 Hz, 2 H), 5.07 (s, 2 H), 6.96 (m, 3 H), 7.33 (m, 1 H), 7.39 (m, 4 H), 7.46 (m, 2 H), 7.67 (m, 1 H), 8.05 (m, 2 H), 8.70 (m, 1 H) 8.99 (m, 1 H); MS (ESI) m/z 456 [M+H]$^+$.

EXAMPLE 69

2-(3'-acetyl-1,1'-biphenyl-4-yl)-N-[1-(2-pyrrolidin-1-ylethyl)-1H-indazol-6-yl]acetamide

EXAMPLE 69A 2-(4-bromophenyl)-N-[1-(2-pyrrolidin-1-ylethyl)-1H-indazol-6-yl]acetamide A mixture of 1-(2-pyrrolidin-1-yl-ethyl)-1H-indazol-6-ylamine (480 mg, 2.09 mmol), (4-bromo-phenyl)-acetic acid (449 mg, 2.09 mmol), ethyldimethylpropylcarbodiimide hydrochloride (470 mg, 2.23 mmol), N-hydroxybenzotriazole (330 mg, 2.44 mmol), N-methyl morpholine (500 mg, 5.00 mmol) in 20 mL of DMF was shaken for 6 hours, concentrated under reduced pressure and the residue purified by preparative reverse-phase HPLC. 1H NMR (500 MHz, DMSO-D6) δ ppm 1.82 (m, 2 H), 1.98 (m, 2 H), 3.01 (m, 2 H), 3.50 (m, 2 H), 3.79 (m, 4 H), 4.66 (t, J=6.24 Hz, 2 H), 7.12 (m, 1 H), 7.32 (m, 2 H), 7.54 (m, 2 H), 7.72 (m, 1 H), 8.08 (s, 1 H), 8.25 (s, 1 H), 10.44 (s, 1 H); MS (DCI/NH$_3$) m/z 429 [M+H]$^+$.

EXAMPLE 69

2-(3'-acetyl-1,1'-biphenyl-4-yl)-N-[1-(2-pyrrolidin-1-ylethyl)-1H-indazol-6-yl]acetamide A solution of Example 65A (aryl bromide) (0.050 g, 0.12 mmol) in ethanol/1,2-dimethoxyethane/toluene (1 mL, 2:1:1) was added to 3-acetylphenylboronic acid (0.030 g, 0.18 mmol). A solution of Pd(PPh$_3$)$_4$ (0.0007 g, 0.0005 mmol) in 1,2-dimethoxyethane (0.5 mL) and aqueous Na$_2$CO$_3$ (24 mg in 0.3 mL H$_2$O, 0.24 mmol) were added. The mixture was heated with shaking to 90° C. for 15 minutes, concentrated, and purified by HPLC with acetonitrile/0.1% trifluoroacetic acid buffer to provide the title compound. $^1$H NMR (300 MHz, DMSO-d6) ppm 1.81 (m, 2H), 2.00 (m, 2H), 2.49 (s, 3 H), 3.02 (m, 2H), 3.51 (m, 2H), 3.68 (m, 2H), 3.70 (s, 1H), 3.77 (s, 1H), 4.66 (t, 2H), 7.12 (m, 1H), 7.32 (m, 1H), 7.49 (m, 2H), 7.54 (m, 1H), 7.62 (m, 1H), 7.72 (m, 2H), 7.73 (m, 1H), 7.94 (m, 1 H), 8.09 (s, 1H), 8.17 (m, 1H), 8.28 (m, 1H); MS (ESI) m/z 467 [M+H]$^+$.

EXAMPLE 70

N-[1-(2-pyrrolidin-1-ylethyl)-1H-indazol-6-yl]-2-[4'-(trifluoromethoxy)-1,1'-biphenyl-4-yl]acetamide The title compound was prepared according to the procedure described in Example 69 substituting 4-trifluoromethoxyphenylboronic acid for 3-acetylphenylboronic acid. $^1$H NMR (300 MHz, DMSO-d$_6$) ppm 1.81 (m, 2H), 1.97 (m, 2H), 3.05 (m, 2H), 3.50 (m, 2H), 3.69 (m, 2H), 3.70 (s, 2H), 4.66 (t, 2H), 7.13 (m, 1H), 7.45 (m, 1H), 7.47 (m, 2H), 7.59 (m, 2H), 7.66 (m, 2H), 7.73 (m, 1H), 7.78 (m, 2H), 8.09 (m, 1 H), 8.29 (s, 1H); MS (ESI) m/z 509 [M+H]$^+$.

EXAMPLE 71

2-(4'-fluoro-1,1'-biphenyl-4-yl)-N-[1-(2-pyrrolidin-1-ylethyl)-1H-indazol-6-yl]acetamide The title compound was prepared according to the procedure described in Example 69 substituting 4-fluorophenylboronic acid for 3-acetylphenylboronic acid. $^1$H NMR (300 MHz, DMSO-d6) ppm 1.80 (m, 2H), 1.97 (m, 2H), 3.00 (m, 2H), 3.50 (m, 2H), 3.69 (m, 2H), 3.75 (s, 2H), 4.66 (t, 2H), 7.13 (m, 1H), 7.28 (m, 2H), 7.32 (m, 1 H), 7.45 (m, 2H), 7.62 (m, 2H), 7.69 (m, 2H), 7.71 (m, 1H), 8.09 (m, 1H), 8.29 (s, 1H); MS (ESI) m/z 443 [M+H]$^+$.

EXAMPLE 72

3-[(1,1'-biphenyl-4-ylmethyl)amino]-N-[1-(2-pyrrolidin-1-ylethyl)-1H-indazol-6-yl]propanamide A mixture of 1-(2-pyrroldin-1-yl-ethyl)-1H-indazol-6-yl amine (0.200 g, 0.869 mmol) in 4 ml anhydrous DMF was treated with tert-butoxycarbonylamino propionic acid (0.200 g, 1.04 mmol), HOBt (0.117 g, 0.869 mmol) and ethyldimethylpropylcarbodiimide hydrochloride (0.166 g, 0.869 mmol) and stirred at room temperature for 4 hours. The mixture was diluted with 50 mL satd. NaHCO$_3$, extracted with ethyl acetate (3×25 ml) and the combined organics dried (MgSO$_4$), filtered and concentrated to provide an oil. To this oil was added 50 mL 4N HCl in dioxane and the mixture was stirred at room temperature for 16 hours. The formed solid was filtered and washed with hexanes to provide 0.20 g of a solid. To a mixture of 0.025 g (0.0670 mmol) of the solid and 4-phenyl-benzaldehyde (12 mgs, 0.080 mmols) in 1:1 methanol/dichloroethane containing 1% acetic acid was added macroporous cyanoborohydride resin (0.064 g, 2.1 mmol/g, 2.0 equiv). The mixture was heated and shaken at 50 C for 6 hours, cooled to room temperature and filtered. The filtrate was concentrated under reduced pressure and the residue purified via reverse phase HPLC to provide the titled compound. MS (ESI) MS m/z 468 (M+H)$^+$. $^1$H NMR (300 MHz, DMSO-d$_6$) δ ppm 1.85 (m, 2 H), 2.0 (m, 2 H), 2.85 (br s, 1 H), 3.05 (m, 2 H), 3.70 (m, 3 H), 3.82 (s, 3 H), 4.0 (m, 2 H), 4.25 (m, 2 H), 4.75 (m, 2 H), 7.15 (m, 1 H), 7.4 (m, 1 H), 7.5 (m, 2 H), 7.6 (m, 2 H), 7.72 (m, 3 H), 7.78 (m, 2 H), 8.1 (s, 1 H), 8.2 (s, 1 H), 9.0 (br s, 1 H).

EXAMPLE 73

3-[(3-phenoxybenzyl)amino]-N-[1-(2-pyrrolidin-1-ylethyl)-1H-indazol-6-yl]propanamide The title compound was prepared according to the procedure for Example 72 substituting 3-phenoxy benzaldehyde for 4-phenyl-benzaldehyde. MS (ESI) MS m/z 484 (M+H)$^+$. $^1$H NMR (300 MHz, DMSO-d$_6$) δ ppm 1.80 (m, 2 H), 1.90 (m, 2 H), 2.0 (m, 2 H), 2.15 (m, 2 H), 2.85 (m, 2 H), 3.0 (m, 2 H), 3.25 (m, 2 H), 3.3 (m, 2 H), 4.75 (m, 2 H), 7.05 (m, 3 H), 7.18 (m, 2 H), 7.30 (m, 2 H), 7.40 (m, 2 H), 7.5 (m, 1 H), 7.75 (m, 1 H), 8.1 (s, 1 H), 8.18 (s, 1 H), 9.0 (br s, 1 H), 9.8 (br s, 1 H).

EXAMPLE 74

N-[1-(2-pyrrolidin-1-ylethyl)-1H-indazol-6-yl]-3-[(4-thien-2-ylbenzyl)amino]propanamide The title compound was prepared according to the procedure for Example 72 substituting 4-thiophen-2-yl-benzaldehyde for 4-phenyl-benzaldehyde. $^1$H NMR (300 MHz, DMSO-d$_6$) δ ppm 1.85 (m, 2 H), 2.0 (m, 2 H), 3.05 (m, 2 H), 3.70 (m, 3 H), 3.82 (s, 3 H), 4.0 (m, 2 H), 4.25 (m, 2 H), 4.75 (m, 2 H), 7.2 (m, 2 H), 7.62 (m, 4 H), 7.75 (m, 3 H), 8.25 (m, 2 H), 9.80 (br s, 1 H), 10.5 (br s, 1 H); MS (ESI) MS m/z 474 (M+H)$^+$.

EXAMPLE 75

2-[(4-phenoxybenzyl)amino]-N-[1-(2-pyrrolidin-1-ylethyl)-1H-indazol-6-yl]acetamide A mixture of 1-(2-pyrroldin-1-yl-ethyl)-1H-indazol-6-yl amine (0.500 g, 2.17 mmol) tert-butoxycarbonylamino acetic acid (0.570 g, 3.26 mmol), HOBt (0.293 g, 2.17 mmols) and ethyldimethylpropylcarbodiimide hydrochloride (0.415 g, 2.17 mmol) in 4 mL anhydrous DMF was stirred at room temperature for 4 hours. 50 mL satd. NaHCO$_3$ was added and the mixture extracted with ethyl acetate (3×25 ml). The combined organics were dried (MgSO$_4$), filtered and concentrated to provide an oil. A mixture of this oil and 50 mL 4N HCl in dioxane was stirred at room temperature for 16 hours, filtered and washed with hexanes to provide 0.60 g of the deprotected amine. A mixture of 0.025 g (0.09 mmol) of the deprotected amine, 4-phenoxy benzaldehyde (0.026 g, 0.13 mmol), and PS-cyanoborohydride (2.3 mmol/g) in 2 ml of 1:1 dichloroethane:methanol containing 0.1 mL glacial acetic acid was heated to 50° C. for 6 hours. The mixture was cooled to room temperature, filtered and resulting filtrate concentrated under reduced pressure to provide a brown residue which was purified using reverse phase HPLC to provide the title compound. MS (ESI) MS m/z 470 (M+H)$^+$. $^1$H NMR (300 MHz, DMSO-d$_6$) δ ppm 1.85 (m, 2 H), 2.0 (m, 2 H), 2.85 (br s, 1 H), 3.05 (m, 2 H), 3.70 (m, 3 H), 4.0 (m, 2 H), 4.25 (m, 2 H), 4.75 (m, 2 H), 7.02 (m, 2 H), 7.07 (m, 2 H), 7.20 (m, 2 H), 7.40 (m, 2 H), 7.55 (m, 2 H), 7.78 (m, 1 H), 8.1 (m, 2 H), 9.40 (br s, 1 H), 9.80 (br s, 1 H).

EXAMPLE 76

2-{[(6-methoxy-2-naphthyl)methyl]amino}-N-[1-(2-pyrrolidin-1-ylethyl)-1H-indazol-6-yl]acetamide The title compound was prepared according to the procedure for Example 75 substituting 6-methoxy-napthalene-2-carbaldehyde for 4-phenoxy benzaldehyde. MS (ESI) MS m/z 458 (M+H)$^+$. $^1$H NMR (300 MHz, DMSO-d$_6$) δ ppm 1.85 (m, 2 H), 2.0 (m, 2 H), 2.85 (br s, 1 H), 3.05 (m, 2 H), 3.70 (m, 3 H), 3.82 (s, 3 H), 4.0 (m, 2 H), 4.25 (m, 2 H), 4.75 (m, 2 H), 7.1 (m, 1 H), 7.2 (m, 1 H), 7.3 (m, 1 H), 7.55 (m, 1 H), 7.75 (m, 1 H), 7.82 (m, 1 H), 7.90 (m, 1 H), 7.95 (m, 1 H), 8.07 (m, 1 H), 8.15 (m, 1 H), 9.40 (br s, 1 H), 9.80 (br s, 1 H).

EXAMPLE 77

2-[(1,1'-biphenyl-4-ylmethyl)amino]-N-[1-(2-pyrrolidin-1-ylethyl)-1H-indazol-6-yl]acetamide The title compound was prepared according to the procedure for Example 75 substituting 4-phenyl benzaldehyde for 4-phenoxy benzaldehyde. 1H NMR (300 MHz, DMSO-d6) ppm 1.85 (m, 2 H), 2.0 (m, 2 H), 2.85 (br s, 1 H), 3.05 (m, 2 H), 3.70 (m, 3 H), 4.0 (m, 2 H), 4.25 (m, 2 H), 4.75 (m, 2 H), 7.02 (t, 2 H), 7.17 (m, 2 H), 7.4 (m, 1 H), 7.62 (m, 4 H), 7.75 (m, 4 H), 9.40 (br s, 1 H), 9.80 (br s, 1 H); MS (ESI) MS m/z 454 (M+H)$^+$.

EXAMPLE 78

2-[(3-phenoxybenzyl)amino]-N-[1-(2-pyrrolidin-1-ylethyl)-1H-indazol-6-yl]acetamide The title compound was prepared according to the procedure for Example 75 substituting 3-phenoxybenzaldehyde for 4-phenoxy benzaldehyde. MS (ESI) MS m/z 470 (M+H)$^+$. $^1$H NMR (300 MHz, CD$_3$OD) δ ppm 2.00 (m, 2 H), 2.20 (m, 2 H), 3.25 (m, 2 H), 3.65 (m, 2 H), 3.82 (m, 2 H), 4.0 (m, 2 H), 4.25 (m, 2 H), 4.75 (m, 2 H), 7.00 (m, 2 H), 7.05–7.15 (m, 3 H), 7.2 (m, 1 H), 7.25 (m, 1 H), 7.35 (m, 2 H), 7.45 (m, 1 H), 7.78 (m, 1 H), 8.1 (m, 1 H), 8.2 (m, 1 H).

EXAMPLE 79

2-({[5-(2-chlorophenyl)-2-furyl]methyl}amino)-N-[1-(2-pyrrolidin-1-ylethyl)-1H-indazol-6-yl]acetamide The title compound was prepared according to the procedure for Example 75 substituting 5-2-(chlorophenyl)furan-2-carbaldehyde for 4-phenoxy benzaldehyde. MS (ESI) MS m/z 478 (M+H)$^+$. $^1$H NMR (300 MHz, DMSO-d$_6$) δ ppm 1.85 (m, 2 H), 2.0 (m, 2 H), 2.85 (br s, 1 H), 3.05 (m, 2 H), 3.70 (m, 3 H), 4.0 (m, 2 H), 4.25 (m, 2 H), 4.75 (m, 2 H), 6.85 (m, 1 H), 7.18 (m, 2 H), 7.38 (m, 1 H), 7.45 (m, 1 H), 7.58 (m, 1 H), 7.74 (m, 1 H), 7.90 (m, 1 H), 8.15 (m, 2 H), 9.8 (br s, 1 H), 10.5 (br s, 1 H).

EXAMPLE 80

N-[1-(2-dimethylamino-ethyl)-1H-indazol-6-yl]-2-(4-phenoxy-phenyl)-acetamide

EXAMPLE 80A dimethyl-[2-(6-nitro-indazol-1-yl)-ethyl]-amine

A mixture of 6-nitroindazole (2 g, 12 mmol) and potassium carbonate (5.1 g 37 mmol) in DMF (40 mL) for 30 minutes, followed by the addition of 2-(dimethylamino) ethylchloride hydrochloride (2.65 g 18.4 mmol) was added. The mixture was heated to 60° C. for 6 hours, cooled to room temperature, filtered through a plug of silica gel, which was rinsed with triethylamine/ethyl acetate (1/4). The filtrate was concentrated under reduced pressure and purified by flash chromatography (silica gel, triethylamine/ethyl acetate 1/30) to provide the title compound (1.8 g, 64% yield). $^1$H NMR (300 MHz, DMSO-d$_6$) ppm 2.16 (s, 6H), 2.73 (t, J=6.44, 2H), 4.66 (t, J=6.44, 2H), 7.94 (m, 1H), 8.00 (m, 1H), 8.31 (m, 1H), 8.79 (m, 1H); MS (DCI/NH$_3$) m/z 235 [M+H]$^+$.

EXAMPLE 80B 1-(2-dimethylamino-ethyl)-1H-indazol-6-ylamine

A mixture of dimethyl-[2-(6-nitro-indazol-1-yl)-ethyl]-amine (1 g, 4.3 mmol), iron powder (1.9 g, 34 mmol), and ammonium chloride (120 mg, 2.2 mmol) in a 4:1 Ethanol/H$_2$O solution (20 mL) was heated to reflux for 3 hours, cooled to room temperature and concentrated under reduced pressure. The residue was stirred in triethylamine/ethyl acetate (1/4, 10 mL) for 15 minutes, filtered through a plug of silica gel which was rinsed with triethylamine/ethyl acetate (1/4), and the filtrate concentrated under reduced pressure to provide the title compound (0.8 g, 92%). $^1$H NMR (300 MHz, DMSO-d$_6$) ppm 2.17 (s, 6H), 2.63(t, J=6.44, 2H), 4.23 (t, J=6.44, 2H), 5.28(s, 2H), 6.50 (m, 2H), 7.35 (m, 1H), 7.69 (m, 1H); MS (DCI/NH$_3$) m/z 205 [M+H]$^+$.

EXAMPLE 80

N-[1-(2-dimethylamino-ethyl)-1H-indazol-6-yl]-2-(4-phenoxy-phenyl)-acetamide

The title compound was prepared according to the procedure described in Example 27 substituting 1-(2-dimethylamino-ethyl)-1H-indazol-6-ylamine for 1-(2-dimethylamino-ethyl)-1H-indazol-5-ylamine. $^1$H NMR (300 MHz, DMSO-d$_6$) ppm 2.84 (s, 6H), 3.60 (t, J=6.24, 2H), 3.70 (s, 2H), 4.69 (t, J=6.24, 2H), 6.99 (m, 4H), 7.13 (m, 1H), 7.38 (m, 4H), 7.72 (m, 1H), 8.08 (s, 1H), 8.28 (s, 1H), 9.49 (s, 1H), 10.43 (s, 1H); MS (DCI/NH$_3$) m/z 415 [M+H]$^+$.

EXAMPLE 81

2-(4-benzyloxy-phenyl)-N-[1-(2-dimethylamino-ethyl)-1H-indazol-6-yl]-acetamide

A mixture of 1-(2-dimethylamino-ethyl)-1H-indazol-6-ylamine (484 mg, 2 mmol), 4-benzyloxy-phenylacetic acid (200 mg, 2 mmol), ethyldimethylpropylcarbodiimide hydrochloride (460 mg, 2.4 mmol), N-hydroxybenzotriazole (324 mg, 2.4 mmol), and N-methyl morpholine (513 mg, 4.8 mmol) in DMF (15 mL) was stirred at room temperature for 6 hours and concentrated under reduced pressure The residue was purified by flash chromatography (Silica gel, ethyl acetate/triethylamine, 30/1) to provide the title compound as a pale yellow solid (95%). $^1$H NMR (300 MHz, DMSO-$d_6$) ppm 2.15 (s, 6H), 2.66 (t, J=6.44, 2H), 3.60 (s, 2H), 4.35 (t, J=6.44, 2H), 5.09 (s, 2H), 6.98 (d, J=8.82, 2H), 7.14 (m, 1H), 7.25–7.45 (m, 6H), 7.65 (m, 1H), 7.94 (m, 1H), 7.94 (s, 1H), 7.95 (s, 1H), 8.12 (s, 1H); MS (DCI/NH$_3$) m/z 429 [M+H]$^+$.

EXAMPLE 82

N-{1-[2-(cyclopentylamino)ethyl]-1H-indazol-6-yl}-2-(4-phenoxyphenyl)acetamide

EXAMPLE 82A 1-(2,2-dimethoxyethyl)-6-nitro-1H-indazole

To a mixture of 6-nitroindazole (10.0 g, 61 mmol) and K$_2$CO$_3$ (9.31 g, 67.5 mmol) in DMF (60 mL) at room temperature was added 2-bromoacetaldehyde dimethylacetal (7.98 mL, 67.5 mmol), after which the mixture was heated to 50 C for 18 hours. The mixture was cooled to room temperature, diluted with diethyl ether (60 mL) and H$_2$O (50 mL) and extracted with diethyl ether (3×50 mL). The combined organic layers were dried (Na$_2$SO$_4$), filtered, and concentrated under reduced pressure to an orange oil. The residue was purified by MPLC (SiO$_2$, 9:1 Hexane:ethyl acetate to 4:1 Hexane:ethyl acetate) to provide 1-(2,2-dimethoxyethyl)-6-nitro-1H-indazole as an orange oil. $^1$H NMR (300 MHz, DMSO-D6) δ ppm 3.27 (s, 6H), 4.71 (d, J=4.75 Hz, 2H), 4.79 (m, 1H), 7.97 (m, 2H), 8.34 (s, 1H), and 8.76 (s, 1H); MS (ESI) 252 (M+H)$^+$.

EXAMPLE 82B 1-(2,2-dimethoxyethyl)-1H-indazole-6-ylamine

To a mixture of 1-(2,2-dimethoxyethyl)-6-nitro-2H-indazole (1.89 g, 7.52 mmol) and NH$_4$Cl (337 mg, 6.01 mmol) in ethanol/H$_2$O (2:1, 75 mL) at room temperature was added Fe (1.28 g, 23.7 mmol) and the mixture was heated for 2 hours at 70 C. The mixture was cooled to room temperature, filtered through celite, which was washed with hot methanol (5×20 mL), and the combined filtrate concentrated under reduced pressure. The residue was diluted with ethyl acetate (50 mL), filtered, the filtrate was concentrated under reduced pressure to provide 1-(2,2-dimethoxyethyl)-2H-indazol-6-ylamine as an amber oil. $^1$H NMR (300 MHz, DMSO-$d_6$) δ ppm 3.26 (m, 6H), 4.23 (d, J=5.42 Hz, 2H), 4.71 (t, J=5.42 Hz, 1H), 5.30 (s, 2H), 6.49 (m, 2H), 7.35 (m, 1H), and 7.73 (s, 1H); MS (ESI) 222 (M+H)$^+$.

EXAMPLE 82C

N-[-1-(2,2-dimethoxyethyl)-1H-indazol-6-yl]-2-(4-phenoxyphenyl)acetamide

A mixture of 1-(2,2-dimethoxyethyl)-2H-indazol-6-ylamine (1.89 g, 8.60 mmol), 4-phenoxyphenylacetic acid (2.06 g, 9.03 mmol), N-methyl morpholine (2.26 mL, 20.6 mmol), HOBt (1.45 g, 10.75 mmol), and ethyldimethylpropylcarbodiimide hydrochloride (2.06 g, 10.75 mmol) in DMF (40 mL) was stirred at room temperature for 3 hours, diluted with H$_2$O (40 mL) and diethyl ether (30 mL). The layers were separated, and the aqueous was extracted with additional diethyl ether (3×50 mL). The combined organic layers were dried (Na$_2$SO$_4$), filtered, and concentrated under reduced pressure to provide a yellow oil which was purified by MPLC (SiO$_2$, 1:1 hexane:ethyl acetate to 1:3 hexane:ethyl acetate) to provide N-[1-(2,2-dimethoxyethyl)-1H-indazol-6-yl]-2-(4-phenoxyphenyl)acetamide as a yellow solid. $^1$H NMR (300 MHz, DMSO-D6) δ ppm 3.26 (m, 6H), 3.68 (s, 2H), 4.37 (d, J=5.42 Hz, 2H), 4.73 (t, J=5.42 Hz, 1H), 6.98 (m, 4H), 7.15 (m, 2H), 7.38 (m, 4H), 7.66 (m, 1H), 7.97 (m, 1H), 8.11 (s, 1H), and 10.35 (s, 1H); MS (ESI) 431 (M–H)$^-$.

EXAMPLE 82D

N-[-(2-oxoethyl)-1H-indazol-6-yl]-2-(4-phenoxyphenyl)acetamide

A mixture of N-[1-(2,2-dimethoxyethyl)-1H-indazol-6-yl]-2-(4-phenoxyphenyl)acetamide (2.0 g, 4.64 mmol) and 2N aqueous HCl (6.0 mL) in acetone (40 mL) was heated to reflux for 3 hours, cooled and diluted with ethyl acetate (300 mL). The layers were separated, and the organic was dried (Na$_2$SO$_4$), filtered, and concentrated under reduced pressure to provide N-[1-(2-oxoethyl)-1H-indazol-6-yl]-2-(4-phenoxyphenyl)acetamide as a beige solid. $^1$H NMR (300 MHz, DMSO-$d_6$) δ ppm 3.55 (s, 2H), 3.7 (m, 2H), 7.0 (m, 4H), 7.1 (m, 2H), 7.3 (m, 1H), 7.4 (m, 4H), 8.0 (s, 1H), 8.15 (s, 1H), 10.4 (s, 1H), and 12.8 (s, 1H); MS (ESI) 384.1 (M–H)$^-$.

EXAMPLE 82

N-{1-[2-(cyclopentylamino)ethyl]-1H-indazol-6-yl}-2-(4-phenoxyphenyl)acetamide

A mixture of N-[1-(2-oxoethyl)-1H-indazol-6-yl]-2-(4-phenoxyphenyl)acetamide (20 mg, 0.05 mmol) and cyclopentylamine (10 μL, 0.10 mmol) in THF (1 mL) was stirred at room temperature for 0.5 hours after which NaCNBH$_3$ (0.104 mL, 0.010 mmol, 1 M in THF) was added and the mixture was stirred for an additional 18 hours. The mixture was diluted with ethyl acetate (2 mL), washed with H$_2$O (1 mL), concentrated under reduced pressure and purified by reverse phase-HPLC to provide the title compound. $^1$H NMR (300 MHz, DMSO-$d_6$) δ ppm 1.5 (m, 6H), 1.9 (m, 2H), 2.9 (m, 1H), 3.4 (m, 2H), 3.8 (m, 2H), 4.6 (t, 2H), 7.0 (m, 4H), 7.1 (m, 2H), 7.4 (m, 4H), 7.7 (m, 1H), 8.05 (s, 1H), 8.3 (s, 1H), 8.6 (m, 1H), and 10.4 (s, 1H); MS (ESI) 455.2 (M+H)$^+$.

EXAMPLE 83

N-(1-{2-[(2-morpholin-4-ylethyl)amino]ethyl}-1H-indazol-6-yl)-2-(4-phenoxyphenyl)acetamide The title compound was prepared by the method described for Example 82, substituting 2-morpholin-2-yl-ethylamine for cyclopentylamine. $^1$H NMR (300 MHz, DMSO-$d_6$) δ ppm 2.95 (m, 4H), 3.3 (m, 2H), 3.5 (t, 2H), 3.7 (m, 8H), 4.6 (t, 2H), 7.0 (m, 4H), 7.05 (m, 2H), 7.2 (m, 4H), 7.7 (m, 2H), 8.1 (s, 1H), 8.3 (s, 1H), and 10.4 (s, 1H); MS (ESI) 500.2 (M+H)$^+$.

EXAMPLE 84

2-(4-phenoxyphenyl)-N-(1-{2-[(tetrahydrofuran-2-ylmethyl)amino]ethyl}-1H-indazol-6-yl)acetamide The title compound was prepared by the method described for Example 82, substituting 2-methylamino-tetrahydrofuran for cyclopentylamine. $^1$H NMR (300 MHz, MeOH-d4) δ ppm 1.6 (m, 1 H), 2.0 (m, 2 H), 2.1 (m, 1 H), 3.0 (m, 1 H), 3.2 (m, 1 H), 3.6 (t, 2 H), 3.7 (s, 2 H), 3.8 (m, 2 H), 4.15 (m, 1 H), 4.7 (t, 2 H), 4.9 (m, 2 H), 7.0 (m, 4 H), 7.1 (m, 2 H), 7.4 (m, 4 H), 7.7 (m, 1 H), 8.05 (s, 1 H), and 8.25 (s, 1 H); MS (ESI) 471.2 (M+H)$^+$.

EXAMPLE 85

N-(1-{2-[(2-cyclohex-1-en-1-ylethyl)amino]ethyl}-1H-indazol-6-yl)-2-(4-phenoxyphenyl)acetamide The title compound was prepared by the method described for Example 82, substituting 2-(1-cyclohexenyl)ethylamine for cyclopentylamine. $^1$H NMR (300 MHz, DMSO-d$_6$) δ ppm 1.5 (m, 4 H), 1.9 (m, 3 H), 2.2 (m, 3H), 3.0 (m, 1 H), 3.4 (m, 2 H), 4.6 (t, 2 H), 5.4 (m, 2 H), 5.9, (m, 1 H), 7.0 (m, 4 H), 7.1 (m, 2 H), 7.25 (m, 1 H), 7.4 (m, 4 H), 7.7 (m, 1 H), 8.05 (s, 1 H), 8.3 (s, 1 H), 8.5 (m, 1 H), and 10.4 (s, 1 H); MS (ESI) 495.3 (M+H)$^+$.

EXAMPLE 86

N-{1-[2-(2-methylpiperidin-1-yl)ethyl]-1H-indazol-6-yl}-2-(4-phenoxyphenyl)acetamide The title compound was prepared by the method described for Example 82, substituting 2-methylpiperidine for cyclopentylamine. $^1$H NMR (300 MHz, MeOH-d$_4$) δ ppm 1.3 (d, 3 H), 1.6 (m, 2 H), 1.9 (m, 4 H), 3.1 (m, 1 H), 3.4 (m, 2 H), 3.65 (m, 2 H), 3.7 (s, 2 H), 3.9 (m, 1 H), 4.9 (m, 2 H), 7.0 (m, 4 H), 7.1 (m, 2 H), 7.4 (m, 4 H), 7.7 (m, 1 H), 8.05 (s, 1 H), and 8.25 (s, 1 H); MS (ESI) 469.2 (M+H)$^+$.

EXAMPLE 87

N-{1-[2-(3-methylpiperidin-1-yl)ethyl]-1H-indazol-6-yl}-2-(4-phenoxyphenyl)acetamide The title compound was prepared by the method described for Example 82, substituting 3-methylpiperidine for cyclopentylamine. $^1$H NMR (300 MHz, DMSO-d$_6$) δ ppm 0.9 (d, 3 H), 1.0 (m, 1H), 1.8 (m, 4 H), 2.6 (m, 1 H), 2.9 (m, 1 H), 3.5 (m, 4 H), 3.7 (s, 2 H), 4.7 (t, 2 H), 7.0 (m, 4 H), 7.1 (m, 2 H), 7.4 (m, 4 H), 7.7 (m, 1 H), 8.1 (s, 1 H), 8.3 (s, 1 H), and 10.4 (s, 1 H); MS (ESI) 469.2 (M+H)$^+$.

EXAMPLE 88

N-{1-[2-(4-methylpiperidin-1-yl)ethyl]-1H-indazol-6-yl}-2-(4-phenoxyphenyl)acetamide The title compound was prepared by the method described for Example 82, substituting 4-methylpiperidine for cyclopentylamine. $^1$H NMR (300 MHz, DMSO-d$_6$) δ ppm 0.9 (d, 3 H), 1.3 (m, 2 H), 1.6 (m, 1 H), 1.8 (m, 2 H), 3.0 (m, 2H), 3.5 (m, 4 H), 3.7 (s, 2 H), 4.7 (t, 2 H), 7.0 (m, 4 H), 7.1 (m, 2 H), 7.4 (m, 4 H), 7.7 (m, 1 H), 8.1 (s, 1 H), 8.3 (s, 1 H), and 10.4 (s, 1 H); MS (ESI) 469.2 (M+H)$^+$.

EXAMPLE 89

N-{1-[2-(2,5-dimethylpyrrolidin-1-yl)ethyl]-1H-indazol-6-yl}-2-(4-phenoxyphenyl)acetamide The title compound was prepared by the method described for Example 82, substituting 2,5-dimethylpyrrolidine for cyclopentylamine. $^1$H NMR (300 MHz, DMSO-d$_6$) δ ppm 1.1 (d, 3H), 1.3 (m, 4 H), 1.7 (m, 2 H), 2.2 (m, 2 H), 3.6 (m, 2 H), 3.7 (s, 2 H), 4.0 (m, 1 H), 4.7 (t, 2 H), 7.0 (m, 4 H), 7.1 (m, 2 H), 7.4 (m, 4 H), 7.7 (m, 1 H), 8.1 (s, 1 H), 8.3 (s, 1 H), and 10.4 (s, 1 H); MS (ESI) 469.2 (M+H)$^+$.

EXAMPLE 90

N-{1-[2-(2-methylpyrrolidin-1-yl)ethyl]-1H-indazol-6-yl}-2-(4-phenoxylphenyl)acetamide The title compound was prepared by the method described for Example 82, substituting 2-methylpyrrolidine for cyclopentylamine. $^1$H NMR (300 MHz, DMSO-d$_6$) δ ppm 1.1 (d, 3H), 1.6 (m, 1 H), 1.9 (m, 2 H), 2.2 (m, 1 H), 3.3 (m, 1 H), 3.8 (m, 5 H), 4.0 (m, 1 H), 4.7 (t, 2 H), 7.0 (m, 4 H), 7.1 (m, 2 H), 7.4 (m, 4 H), 7.7 (m, 1 H), 8.1 (s, 1 H), 8.3 (s, 1 H), and 10.4 (s, 1 H); MS (ESI) 455.2 (M+H)$^+$.

EXAMPLE 91

N-{1-[3-(3-methylpiperidin-1-yl)propyl]-1H-indazol-6-yl}-2-(4-phenoxyphenyl)acetamide

EXAMPLE 91A 1-(3,3-dimethoxypropyl)-6-nitro-1H-indazole

To a mixture of 6-nitroindazole (4.05 g, 24.8 mmol), K$_2$CO$_3$ (4.45 g, 32.2 mmol), and KI (411 mg, 2.48 mmol) in DMF (25 mL) at room temperature was added 3-bromopropoinaldehyde dimethylacetal (5.00 g, 27.3 mmol), after which the mixture was heated to 70 C for 18 hour. The mixture was cooled to room temperature, diluted with diethyl ether (25 mL) and H$_2$O (25 mL), the layers separated, and the aqueous layer extracted with additional diethyl ether (3×25 mL). The combined organic layers were dried (Na$_2$SO$_4$), filtered, and concentrated under reduced pressure and purified by MPLC (SiO2, 9:1 hexane:ethyl acetate to 4:1 hexane:ethyl acetate) to provide the title compound. $^1$H NMR (300 MHz, DMSO-D6) δ ppm 2.12 (m, 2 H), 3.19 (s, 6 H), 4.34 (t, J=5.76 Hz, 1H), 4.59 (t, J=6.95 Hz, 2 H), 7.97 (m, 2 H), 8.34 (s, 1 H), and 8.71 (s, 1 H); MS (ESI) 266 (M+H)$^+$.

EXAMPLE 91B 1-(3,3-dimethoxypropyl)-1H-indazole-6-ylamine

To a mixture of 2-(3,3-dimethoxypropyl)-6-nitro-2H-indazole (1.5 g, 5.66 mmol) and NH$_4$Cl (254 mg, 4.53 mmol) in ethanol/H$_2$O (2:1, 56 mL) at room temperature was added Fe (962 mg, 17.8 mmol) and the mixture was heated for 2 hours at 70 C. The mixture was cooled to room temperature, filtered through celite which was washed with hot methanol (5×20 mL), and the combined filtrate concentrated under reduced pressure. The residue was diluted with ethyl acetate (30 mL), filtered, concentrated under reduced pressure to provide the title compound. $^1$H NMR (300 MHz, DMSO-D6) δ ppm 2.01 (m, 2 H), 3.23 (s, 6 H), 4.17 (m, 2 H), 4.29 (t, J=5.59 Hz, 1 H), 5.35 (s, 2 H), 6.49 (m, 2 H), 7.35 (m, 1 H), and 7.72 (s, 1 H).

EXAMPLE 91C

N-[1-(3,3-dimethoxypropyl)-1H-indazol-6-yl]-2-(4-phenoxyphenyl)acetamide

A mixture of 1-(3,3-dimethoxypropyl)-1H-indazole-6-ylamine (1.32 g, 5.60 mmol), 4-phenoxyphenylacetic acid (1.34 g, 5.88 mmol), N-methyl morpholine (1.47 mL, 13.4 mmol), HOBt (945 mg, 7.0 mmol), and ethyldimethylpropylcarbodiimide hydrochloride (1.34 g, 7.0 mmol) in DMF (28 mL) was stirred at room temperature for 3 hours followed by the addition of H$_2$O (40 mL) and diethyl ether (30 mL). The layers were separated, and the aqueous was extracted with diethyl ether (3×30 mL). The combined organic layers were dried (Na$_2$SO$_4$), filtered, concentrated under reduced pressure and purified by MPLC (SiO$_2$, 1:1 hexane:ethyl acetate to 1:3 hexane:ethyl acetate) to provide the title compound. $^1$H NMR (300 MHz, DMSO-D6) δ ppm 2.05 (m, 2 H), 3.22 (m, 6 H), 3.68 (s, 2 H), 4.29 (m, 3 H), 6.99 (m, 4 H), 7.14 (m, 2 H), 7.38 (m, 4 H), 7.66 (m, 1 H), 7.97 (s, 1 H), 8.12 (s, 1 H), and 10.34 (s, 1 H); MS (ESI) 444 (M−H)$^-$.

EXAMPLE 91D

N-[1-(3-oxopropyl)-1H-indazol-6-yl]-2-(4-phenoxyphenyl)acetamide

A mixture of N-[1-(3,3-dimethoxypropyl)-1H-indazol-6-yl]-2-(4-phenoxyphenyl)acetamide (500 mg, 1.12 mmol) and 2N aqueous HCl (2.5 mL) in acetone (5 mL) was heated to 50 C for 3 hours, cooled to room temperature and concentrated under reduced pressure to a volume of ~2 mL. Diethyl ether (15 mL) was added with stirring and the mixture was filtered. The filtered solid was washed with additional diethyl ether (10 mL) and air-dried to provide the title compound. MS (ESI) 398 (M−H)$^-$.

EXAMPLE 91

N-{1-[3-(3-methylpiperidin-1-yl)propyl]-1H-indazol-6-yl}-2-(4-phenoxyphenyl)acetamide To a mixture of N-[1-(3-oxopropyl)-1H-indazol-6-yl]-2-(4-phenoxyphenyl)acetamide (20 mg, 0.05 mmol) and 3-methylpiperidine (10 mg, 0.10 mmol) in methanol containing 2% v/v acetic acid (1 mL) was added and MP-CNBH$_3$ (52 mg, 0.065 mmol). The mixture was shaken at 40 C for 18 hours, cooled to room temperature and filtered, eluting with additional methanol (3×0.5 mL). The filtrate was concentrated under reduced pressure and was purified by RP-HPLC to provide the title compound. $^1$H NMR (300 MHz, DMSO-D6) δ ppm 0.85 (d, J=6.44 Hz, 3 H), 0.99 (m, 1H), 1.71 (m, 4 H), 2.26 (m, 2H,) 2.73 (m, 1 H), 3.06 (m, 2 H), 3.35 (m, 3 H), 3.69 (s, 2 H), 4.38 (t, J=6.95 Hz, 2 H), 6.99 (m, 4 H), 7.10 (m, 2 H), 7.39 (m, 4 H), 7.69 (m, 1 H), 8.01 (s, 1 H), 8.26 (s, 1 H), and 10.39 (s, 1 H); MS (ESI) 483 (M+H)$^+$.

EXAMPLE 92

N-[1-(3-azepan-1-ylpropyl)-1H-indazol-6-yl]-2-(4-phenoxyphenyl)acetamide

The title compound was prepared by the method described for Example 91, substituting hexamethylenimine for 3-methylpiperidine. $^1$H NMR (300 MHz, DMSO-D6) δ ppm 1.62 (m, 8 H), 2.22 (m, 2 H), 3.12 (m, 4 H), 3.32 (m, 2 H), 3.69 (s, 2 H), 4.38 (t, J=6.78 Hz, 2 H), 6.99 (m, 4 H), 7.10 (m, 2 H), 7.39 (m, 4 H), 7.69 (m, 1 H), 8.01 (s, 1 H), 8.25 (s, 1 H), and 10.39 (s, 1 H); MS (ESI) 483 (M+H)$^+$.

EXAMPLE 93

N-{1-[3-(4-hydroxypiperidin-1-yl)propyl]-1H-indazol-6-yl}-2-(4-phenoxyphenyl)acetamide The title compound was prepared by the method described for Example 91, substituting 4-hydroxypiperidine for 3-methylpiperidine. $^1$H NMR (300 MHz, DMSO-D6) δ ppm 1.48 (m, 1 H), 1.76 (m, 2 H), 1.91 (m, 1 H), 2.24 (m, 2 H,) 2.90 (m, 1 H), 3.08 (m, 3 H), 3.26 (m, 1 H), 3.39 (m, 1 H), 3.59 (m, 1 H), 3.69 (s, 2 H), 4.23 (m, 1 H), 4.37 (t, J=6.61 Hz, 2 H), 6.99 (m, 4 H), 7.11 (m, 2 H), 7.39 (m, 4 H), 7.69 (m, 1 H), 8.01 (s, 1 H), 8.25 (s, 1 H), and 10.39 (s, 1 H); MS (ESI) 485 (M+H)$^+$.

EXAMPLE 94

N-{1-[3-(4-methylpiperidin-1-yl)propyl]-1H-indazol-6-yl}-2-(4-phenoxyphenyl)acetamide The title compound was prepared by the method described for Example 91, substituting 4-methylpiperidine for 3-methylpiperidine. $^1$H NMR (300 MHz, DMSO-D6) δ ppm 0.89 (d, J=6.44 Hz, 3 H), 1.26 (m, 2 H,) 1.57 (m, 1 H), 1.74 (m, 2 H), 2.24 (m, 2 H), 2.83 (m, 2 H), 3.07 (s, 2 H), 3.18 (m, 2 H,) 3.69 (s, 2 H), 4.38 (t, J=6.78 Hz, 2 H), 6.99 (m, 4 H), 7.10 (m, 2 H), 7.38 (m, 4 H), 7.69 (m, 1H,) 8.01 (s, 1 H), 8.25 (s, 1 H), and 10.39 (s, 1 H); MS (ESI) 483 (M+H)$^+$.

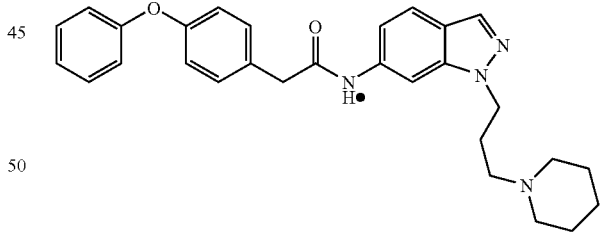

EXAMPLE 95

2-(4-phenoxyphenyl)-N-[1-(3-piperidin-1-ylpropyl)-1H-indazol-6-yl]acetamide

The title compound was prepared by the method described for Example 91, substituting piperidine for 3-methylpiperidine. $^1$H NMR (300 MHz, DMSO-D6) δ ppm 1.35 (m, 1 H), 1.59 (m, 3 H), 1.75 (m, 2 H), 2.23 (m, 2 H), 2.83 (m, 2 H), 3.05 (m, 2 H), 3.37 (m, 2 H), 3.69 (s, 2 H), 4.38 (t, J=6.61 Hz, 2 H), 6.99 (m, 4 H), 7.10 (m, 2 H), 7.37 (m, 4 H), 7.69 (m, 1 H), 8.01 (s, 1 H), 8.25 (s, 1 H), and 10.39 (s, 1 H); MS (ESI) 469 (M+H)$^+$.

EXAMPLE 96

2-(4-phenoxyphenyl)-N-[1-(3-pyrrolidin-1-ylpropyl)-1H-indazol-6-yl]acetamide

The title compound was prepared by the method described for Example 91, substituting pyrrolidine for 3-methylpiperidine. $^1$H NMR (300 MHz, DMSO-D6) δ ppm 1.81 (m, 2 H), 1.97 (m, 2 H), 2.19 (m, 2 H), 2.96 (m, 2 H), 3.15 (m, 2 H), 3.52 (m, 2 H), 3.69 (s, 2 H), 4.38 (t, J=6.78 Hz, 2 H), 6.99 (m, 4 H), 7.10 (m, 2 H), 7.39 (m, 4 H), 7.69 (m, 1 H), 8.01 (s, 1 H), 8.25 (s, 1 H), and 10.39 (s, 1 H); MS (ESI) 455 (M+H)$^+$.

EXAMPLE 97

N-(1-{3-[(2S)-2-(methoxymethyl)pyrrolidin-1-yl]propyl}-1H-indazol-6-yl)-2-(4-phenoxyphenyl)acetamide The title compound was prepared by the method described for Example 91, substituting (S)-2-methoxymethylpyrrolidine for 3-methylpiperidine. $^1$H NMR (300 MHz, DMSO-D6) δ ppm 1.63 (m, 1 H,) 1.75 (m, 1 H), 1.94 (m, 1 H), 2.05 (m, 1 H), 2.25 (m, 2 H), 3.09 (d, J=9.49 Hz, 2 H), 3.21 (s, 3 H), 3.30 (m, 1 H), 3.50 (m, 3 H), 3.62 (m, 1 H), 3.69 (s, 2 H), 4.37 (d, J=6.10 Hz, 2 H), 6.99 (m, 4 H), 7.10 (m, 2 H), 7.39 (m, 4 H), 7.69 (m, 1 H), 8.01 (s, 1 H), 8.25 (s, 1 H), and 10.39 (s, 1 H); MS (ESI) 499 (M+H)$^+$.

EXAMPLE 98

N-{1-[3-(diisopropylamino)propyl]-1H-indazol-6-yl}-2-(4-phenoxyphenyl)acetamide

The title compound was prepared by the method described for Example 91, substituting diisopropylamine for 3-methylpiperidine. $^1$H NMR (300 MHz, DMSO-D6) δ ppm 1.18 (m, 12 H), 2.24 (m, 2 H), 3.17 (m, 2 H), 3.57 (m, 2 H), 3.69 (s, 2 H), 4.40 (t, J=6.44 Hz, 2 H), 6.99 (m, 4 H), 7.09 (m, 2 H), 7.38 (m, 4 H), 7.69 (m, 1 H), 8.02 (s, 1 H), 8.27 (s, 1 H), and 10.38 (s, 1 H); MS (ESI) 485 (M+H)$^+$.

EXAMPLE 99

N-(1-{3-[(2S)-2-(hydroxymethyl)pyrrolidin-1-yl]propyl}-1H-indazol-6-yl)-2-(4-phenoxyphenyl)acetamide The title compound was prepared by the method described for Example 91, substituting (S)-2-pyrrolidinemethanol for 3-methylpiperidine. $^1$H NMR (300 MHz, DMSO-D6) δ ppm 1.73 (m, 2 H), 1.97 (m, 2 H), 2.26 (m, 2 H), 3.05 (d, J=3.73 Hz, 2 H), 3.37 (m, 1 H), 3.53 (m, 4 H), 3.69 (s, 3 H), 4.38 (t, J=6.61 Hz, 2 H), 6.99 (m, 4 H), 7.10 (m, 2 H), 7.39 (m, 4 H), 7.69 (m, 1 H), 8.00 (s, 1 H), 8.24 (s, 1 H), and 10.39 (s, 1 H); MS (ESI) 485 (M+H)$^+$.

EXAMPLE 100

N-{1-[3-(2-methylpyrrolidin-1-yl)propyl]-1H-indazol-6-yl}-2-(4-phenoxyphenyl)acetamide The title compound was prepared by the method described for Example 91, substituting 2-methylpyrrolidine for 3-methylpiperidine. $^1$H NMR (300 MHz, DMSO-D6) δ ppm 1.28 (d, J=6.44 Hz, 3 H), 1.54 (m, 1 H), 1.88 (m, 2 H), 2.18 (m, 3 H), 3.02 (m, 2 H), 3.37 (d, J=16.27 Hz, 2 H), 3.57 (m, 1 H), 3.69 (s, 2 H), 4.40 (t, J=6.78 Hz, 2 H), 6.99 (m, 4 H), 7.10 (m, 2 H), 7.39 (m, 4 H), 7.69 (m, 1 H), 8.02 (s, 1 H), 8.26 (s, 1 H), and 10.39 (s, 1 H); MS (ESI) 469 (M+H)$^+$.

EXAMPLE 101

N-{1-[3-(cyclopentylamino)propyl]-1H-indazol-6-yl}-2-(4-phenoxyphenyl)acetamide

The title compound was prepared by the method described for Example 91, substituting cyclopentylamine for 3-methylpiperidine. $^1$H NMR (300 MHz, DMSO-D6) δ ppm 1.54 (m, 4 H), 1.65 (s, 2 H), 1.90 (m, 2 H), 2.13 (m, 2 H), 2.92 (m, 2 H), 3.44 (m, 1 H), 3.69 (s, 2 H), 4.41 (t, J=6.78 Hz, 2 H), 6.99 (m, 4 H), 7.10 (m, 2 H), 7.38 (m, 4 H), 7.69 (m, 1 H), 8.00 (s, 1 H), 8.26 (s, 1 H), 8.37 (s, 1 H), and 10.39 (s, 1 H); MS (ESI) 469 (M+H)$^+$.

EXAMPLE 102

N-[1-(3-morpholin-4-ylpropyl)-1H-indazol-6-yl]-2-(4-phenoxyphenyl)acetamide

The title compound was prepared by the method described for Example 91, substituting morpholine for 3-methylpiperidine. $^1$H NMR (300 MHz, DMSO-D6) δ ppm 2.21 (m, 2 H), 3.17 (m, 3 H), 3.39 (s, 2 H), 3.58 (m, 3 H), 3.69 (s, 2 H), 3.96 (m, 2 H), 4.39 (t, J=6.61 Hz, 2 H), 7.00 (m, 4 H), 7.10 (m, 2 H), 7.39 (m, 4 H), 7.70 (m, 1 H), 8.02 (s, 1 H), 8.26 (s, 1 H), and 10.39 (s, 1 H); MS (ESI) 471 (M+H)$^+$.

EXAMPLE 103

N-(1-{3-[cyclohexyl(methyl)amino]propyl}-1H-indazol-6-yl)-2-(4-phenoxyphenyl)acetamide The title compound was prepared by the method described for Example 91, substituting N-methylcyclohexylamine for 3-methylpiperidine. $^1$H NMR (300 MHz, DMSO-D6) δ ppm 1.07 (m, 1 H), 1.25 (m, 4 H), 1.84 (m, 4 H), 2.19 (m, 3 H), 2.67 (d, J=4.75 Hz, 3 H), 3.06 (m, 1 H), 3.17 (m, 2 H), 3.69 (s, 2 H), 4.38 (t, J=6.78 Hz, 2 H), 6.99 (m, 4 H), 7.09 (m, 2 H), 7.38 (m, 4 H), 7.69 (m, 1 H), 8.01 (s, 1 H), 8.26 (s, 1 H), and 10.39 (s, 1 H); MS (ESI) 497 (M+H)$^+$.

EXAMPLE 104

N-{1-[3-(diisobutylamino)propyl]-1H-indazol-6-yl}-2-(4-phenoxyphenyl)acetamide

The title compound was prepared by the method described for Example 91, substituting diisobutylamine for 3-methylpiperidine. $^1$H NMR (300 MHz, DMSO-D6) δ ppm 0.89 (m, 12 H), 1.92 (m, 2 H), 2.23 (m, 2 H), 2.89 (m, 4 H), 3.14 (m, 2 H), 3.69 (s, 2 H), 4.41 (t, J=6.44 Hz, 2 H), 7.00 (m, 4 H), 7.10 (m, 2 H), 7.39 (m, 4 H), 7.70 (m, H), 8.02 (s, 1 H), 8.27 (s, 1 H), and 10.39 (s, 1 H); MS (ESI) 513 (M+H)$^+$.

EXAMPLE 105

2-[4-(benzyloxy)phenyl]-N-{1-[2-(2-oxo-1,3-oxazolidin-3-yl)ethyl]-1H-indazol-6-yl}acetamide

EXAMPLE 105A

3-[2-(6-nitro-indazol-1-yl)-ethyl]-oxazolidin-2-one

To a mixture of 3-(2-hydroxy-ethyl)-oxazolidin-2-one (1.00 g, 7.63 mmol) and Hunigs base (2.92 mL, 16.8 mmol)

in dichloromethane (19 mL) at 0° C. was added mesyl chloride (0.650 mL, 8.40 mmol) slowly via syringe. The mixture was stir cold for three hours, diluted with 10 mL of water and 25 mL of dichloromethane. The layers were separated and the organic layer was washed with aqueous NaHCO$_3$ (3×30 mL) followed by water (1×15 mL). The organic layer was then dried (Na$_2$SO$_4$), filtered, and concentrate under reduced pressure to provide 650 mg of methanesulfonic acid 2-(2-oxo-oxazolidin-3-yl)-ethyl ester as a light brown oil. In a separate flask 6-nitroindazole (318 mg, 1.95 mmol) was treated with potassium carbonate (538 mg 3.9 mmol) in DMF (10 mL) for 30 minutes, afer which methanesulfonic acid 2-(2-oxo-oxazolidin-3-yl)-ethyl ester (490 mg 2.34 mmol) was added. The reaction mixture was heated to 60° C. for 6 hours, cooled to room temperature, filtered through a plug of silica gel and rinsed with triethylamine/ethyl acetate (1/4). The filtrate was concentrated under reduced pressure and purified by flash chromatography (silica gel, triethylamine/ethyl acetate 1/30) to provide the title compound (210 mg, 39% yield). $^1$H NMR (300 MHz, DMSO-d$_6$) ppm 3.49 (m, 2H), 3.62 (t, J=5.76, 2H), 4.13 (m, 2H), 4.76 (t, J=5.76, 2H), 7.97–8.03 (m, 2H), 8.33 (m, 1H), 8.83 (m, 1H); MS (DCI/NH$_3$) m/z 277 [M+H]$^+$.

EXAMPLE 105B

3-[2-(6-amino-indazol-1-yl)-ethyl]-oxazolidin-2-one

A mixture of 3-[2-(6-Nitro-indazol-1-yl)-ethyl]-oxazolidin-2-one (200 mg, 0.72 mmol), iron powder (400 mg, 7.1 mmol), and ammonium chloride (20 mg, 0.37 mmol) in a 4:1 ethanol/H$_2$O solution (5 mL) was heated to reflux for 3 hours, cooled to room temperature, concentrated under reduced pressure. The resudue was stirred in triethylamine/ethyl acetate (1/4, 10 mL) for 15 minutes, filtered through a plug of silica gel which was rinsed with triethylamine/ethyl acetate (1/4). The filtrate was concentrated under reduced pressure to provide the title compound (120 mg, 67%). $^1$H NMR (300 MHz, DMSO-d$_6$) ppm 4.03 (s, 3H), 4.42 (d, J=6.10, 1H), 6.04 (m, 1H), 7.25 (m, 1H), 7.32 (m, 1H), 7.38 (m, 1H), 7.48 (m, 2H), 7.69 (m, 1H), 7.79 (m, 1H), 8.44 (m, 1H), 9.12 (s, 1H); MS (DCI/NH$_3$) m/z 247 [M+H]$^+$.

EXAMPLE 105

2-(4-benzyloxy-phenyl)-N-{1-[2-(2-oxo-oxazolidin-3-yl)-ethyl]-1H-indazol-6-yl}-acetamide A mixture of 3-[2-(6-Amino-indazol-1-yl)-ethyl]-oxazolidin-2-one (58 mg, 0.24 mmol), 4-benzyloxyphenylacetic acid (68 mg, 0.28 mmol), ethyldimethylpropylcarbodiimide hydrochloride (53 mg, 0.28 mmol), N-hydroxybenzotriazole (37 mg, 0.28 mmol) and N-methyl morpholine (60 mg, 0.56 mmol) in 3 mL of DMF was stirred at room temperature for 6 hours. The mixture was concentrated under reduced pressure and the residue was purified by flash chromatography (silica gel, ethyl acetate/triethylamine, 30/1) to provide the title compound as a pale yellow solid (58 mg, 52%); $^1$H NMR (300 MHz, DMSO-d$_6$) ppm 3.39 (m, 2H), 3.55 (m, 2H), 3.61 s, 2H0, 4.09 (m, 2H), 4.47 (m, 2H), 5.09 (s, 2H), 6.67 (d, J=8.47, 2H), 7.13 (m, 1H), 7.27 (m, 2H), 7.31–7.45 (m, 5H), 7.65 (m, 1H), 7.97 (m, 1H), 8.13 (s, 1H), 10.30 (s, 1H); MS (DCI/NH$_3$) m/z 471 [M+H]$^+$.

EXAMPLE 106

2-[4-(benzyloxy)phenyl]-N-[1-(3-dimethylamino-propyl)-1H-indazol-6-yl]acetamide

EXAMPLE 106A dimethyl-{3-(6-nitro-indazol-1-yl)-propyl}-amine

A mixture of 6-nitro-1H-indazole (0.500 g, 3.07 mmol) and potassium carbonate (0.889 g, 6.44 mmol) in 15.3 mL of DMF was stirred for 30 minutes after which (3-chloropropyl)-dimethyl-amine hydrochloride (0.553 g 3.50 mmol) was added. The reaction mixture was then heated to 60° C. for 6 hours, cooled to room temperature and filtered through a plug of silica gel which was rinsed with triethylamine/ethyl acetate (1/4). The filtrate was concentrated under reduced pressure and the residue purified by flash chromatography (silica gel, triethylamine/ethyl acetate 1/30). 1H NMR (300 MHz, DMSO-D6) δ ppm 1.97 (m, 2 H), 2.10 (m, 6 H), 2.14 (m, 2 H), 4.58 (t, J=6.78 Hz, 2 H), 7.99 (m, 2 H), 8.32 (m, 1 H), 8.74 (m, 1 H); MS (DCI/NH$_3$) m/z 249 [M+H]$^+$.

EXAMPLE 106B 1-(3-dimethylamino-propyl)-1H-indazol-6-ylamine

A mixture of dimethyl-{3-(6-nitro-indazol-1-yl)-propyl}-amine (0.400 g, 1.61 mmol), iron powder (0.897 g, 16.1 mmol), and ammonium chloride (0.0430 mg, 0.811 mmol) in a 4:1 solution of ethanol/H$_2$O was heated to reflux for 3 hours, cooled to room temperature and concentrated under reduced pressure. The residue was taken up and stirred in triethylamine/ethyl acetate (1/4, 30 mL) for 15 minutes, filtered through a plug of silica gel which was rinsed with triethylamine/ethyl acetate (1/4) and concentrated under reduced pressure to provide the title compound. 1H NMR (300 MHz, DMSO-D6) δ ppm 1.95 (m, J=14.75, 7.63 Hz, 2 H), 2.28 (m, 6 H), 2.38 (t, J=6.95 Hz, 2 H), 4.18 (t, J=6.95 Hz, 2 H), 5.30 (s, 2 H), 6.50 (m, 2 H), 7.35 (m, 1 H), 7.71 (s, 1 H); MS (DCI/NH$_3$) m/z 219 [M+H]$^+$.

EXAMPLE 106

2-[4-(benzyloxy)phenyl]-N-[1-(3-dimethylaminopropyl)-1H-indazol-6-yl]acetamide

A mixture of Example 46C (0.0550 g, 0.252 mmol), (4-benzyloxy-phenyl)-acetic acid (0.0610 g, 0.253 mmol), ethyldimethylpropylcarbodiimide hydrochloride (0.0480 g, 0.253 mmol), N-hydroxybenzotriazole (0.0340 g, 0.252 mmol), in 1.5 mL of DMF, were stir under nitrogen for 6 hours, concentrated under reduced pressure. The residue was dissolved in ethyl acetate and washed with sat. NaHCO$_3$ (3×30 mL), H$_2$O (1×15 mL), dried (Na$_2$SO$_4$), filtered, concentrated under reduced pressure and purification by column chromatography (50–80% ethyl acetate (3% triethylamine)/hexanes) to provided the title compound. 1H NMR (300 MHz, DMSO-D6) δ ppm 1.93 (m, 2 H), 2.16 (m, 6 H), 2.28 (m, 2 H), 3.59 (m, 2 H), 4.29 (m, 2 H), 5.09 (m, 2 H), 6.97 (m, 2 H), 7.12 (m, 1 H), 7.26 (m, 2 H), 7.39 (m, 5 H), 7.65 (m, 1 H), 7.95 (s, 1 H), 8.12 (m, 1 H), 10.28 (s, 1 H); MS (ESI) m/z 443 [M+H]$^+$.

EXAMPLE 107

2-[4-(benzyloxy)phenyl]-N-{1-[2-(2-oxopyrrolidin-1-yl)ethyl]-1H-indazol-6-yl}acetamide The title compound was prepared according to the procedure described in Example 105 substituting methanesulfonic acid 2-(2-oxo-pyrrolidin-1-yl)-ethyl-ester for 1-(2-chloro-ethyl)-pyrrolidine hydrochloride. $^1$H NMR (300 MHz, DMSO-$d_6$) δ ppm 1.68 (m, 2H), 2.02 (t, 2H, J=8.13), 3.01 (t, 2H, J=6.95), 3.54 (t, 2H, J=5.77), 3.60 (s, 2H), 4.42 (t, 2H, J=5.77), 5.09 (s, 2H), 6.97 (m, 2H), 7.13–7.46 (m, 8H), 7.65 (m, 1H), 7.96 (s, 1H), 8.06 (s, 1H), 10.29 (s, 1H); MS (DCI/NH$_3$) m/z 469 [M+H]$^+$.

EXAMPLE 108

2-[4-(benzyloxy)phenyl]-N-{1-[2-(2,5-dioxopyrrolidin-1-yl)ethyl]-1H-indazol-6-yl}acetamide The title compound was prepared according to the procedure described in Example 105 substituting methanesulfonic acid 2-(2,5-dioxo-pyrrolidin-1-yl)-ethyl-ester for 1-(2-chloro-ethyl)-pyrrolidine hydrochloride. $^1$H NMR (300 MHz, DMSO-$d_6$) δ ppm 2.42 (s, 4H), 3.60 (s, 2H), 3.70 (t, 2H, J=5.77), 4.44 (t, 2H, J=5.77), 5.09 (s, 2H), 6.98 (d, 2H, J=8.82), 7.09–7.46 (m, 8H), 7.63 (m, 1H), 7.92 (s, 1H), 8.00 (s, 1H), 10.30 (s, 1H); MS (DCI/NH$_3$) m/z 483 [M+H]$^+$.

EXAMPLE 109

2-[4-(benzyloxy)phenyl]-N-[3-chloro-1-(2-pyrrolidin-1-ylethyl)-1H-indazol-4-yl]acetamide

EXAMPLE 109A 3-chloro-4-nitro-1H-indazole

To a mixture of NaOH (0.500 g, 12.5 mmol) in H$_2$O (15.0 mL) was added 4-nitroindazole (0.500 g, 3.07 mmol) after which it was heated until a red solution formed. The solution was immediately placed in an ice-water bath for 15 minutes before NaClO (6.00 mL, 5.25%, 4.50 mmol) was added. The mixture was stirred at 0° C. for 5 hour, the pH adjusted to 7 with dilute HCl and extracted with ethyl acetate. The combined organic layer was washed with H$_2$O, concentrated under reduced pressure and purified by flash chromatography to provide the title compound. $^1$H NMR (300 MHz, DMSO-$d_6$) δ ppm 8.17 (m, 1H), 8.57 (m, 1H), 8.77 (m, 1H), 14.17 (s, 1H); MS (DCI/NH$_3$) m/Z 197[M+H]$^+$.

EXAMPLE 109B 3-chloro-4-nitro-1-(2-pyrrolidin-1-yl-ethyl)-1H-indazole

A mixture of 3-chloro-4-nitro-1H-indazole (0.550 g, 2.79 mmol) was treated with potassium carbonate (1.20 g 8.70 mmol) in DMF (10 mL) for 30 minutes, after which 1-(2-chloro-ethyl)-pyrrolidine hydrochloride (0.710 g, 4.20 mmol) was added. The mixture was heated to 50° C. for 6 hours, cooled to room temperature and filtered through a plug of silica gel which was rinsed with triethylamine/ethyl acetate (1/4). The combined filtrate was concentrated under reduced pressure and purified by flash chromatography (silica gel, triethylamine/ethyl acetate 1/30) to provide the title compound. $^1$H NMR (300 MHz, DMSO-$d_6$) δ ppm 1.60 (m, 4H), 2.46 (m, 4H), 2.90 (t, 2H, J=6.44), 4.61 (t, 2H, J=6.44), 7.66 (m, 1H), 7.98 (m, 1H), 8.25 (m, 1H); MS (DCI/NH$_3$) m/z 261 [M+H]$^+$.

EXAMPLE 109C 3-chloro-1-(2-pyrrolidin-1-yl-ethyl)-1H-indazol-4-ylamine

A mixture of 3-Chloro-4-nitro-1-(2-pyrrolidin-1-yl-ethyl)-1H-indazole (0.40 g, 1.4 mmol), iron powder (0.76 g, 14 mmol), and ammonium chloride (37 mg, 0.68 mmol) in 80% Ethanol was heated to reflux for 3 hours, cooled to room temperature and concentrated under reduced pressure. The residue was stirred in triethylamine/ethyl acetate (1/4, 20 mL) for 15 minutes, filtered through a plug of silica gel which was rinsed with triethylamine/ethyl acetate (1/4), and concentrated to provide the title compound (0.30 g, 84%). $^1$H NMR (300 MHz, DMSO-$d_6$) ppm 1.62 (m, 4H), 2.44 (m, 4H), 2.81 (t, 2H, J=6.78), 4.31 (t, 2H, J=6.78), 5.62 (s, 2H), 6.23 (d, 1H, J=7.46), 6.73 (d, 1H, J=8.48), 7.09 (m, 1H); MS (DCI/NH$_3$) m/z 265 [M+H]$^+$.

EXAMPLE 109

2-[4-(benzyloxy)phenyl]-N-[3-chloro-1-(2-pyrrolidin-1-ylethyl)-1H-indazol-4-yl]acetamide A mixture of 3-chloro-1-(2-pyrrolidin-1-yl-ethyl)-1H-indazol-4-ylamine (300 mg, 1.14 mmol), (4-benzyloxy-phenyl)-acetic acid (302 mg, 1.25 mmol), ethyldimethylpropylcarbodiimide hydrochloride (261 mg g, 1.37 mmol), N-hydroxybenzotriazole (184 mg, 1.37 mmol), N-methyl morpholine (290 mg, 2.72 mmol) in 5 mL of DMF was stirred for 6 hours and concentrated under reduced pressure. The residue was purified by flash chromatography (silica gel, triethylamine/ethyl acetate, 1/10) to provide the title compound. $^1$H NMR (300 MHz, DMSO-$d_6$) ppm 1.60 (m, 4H), 2.43 (m, 4H), 2.85 (t, 2H, J=6.44), 3.69 (s, 2H), 4.48 (t, 2H, J=6.44), 5.10 (s, 2H), 6.99 (d, 2H, J=8.81), 7.28–7.48 (m, 9H), 7.59 (m, 1H), 10.10 (s, 1H); MS (DCI/NH$_3$) m/z 489 [M+H]$^+$.

EXAMPLE 110

N-[3-chloro-1-(2-pyrrolidin-1-yl-ethyl)-1H-indazol-4-yl]-2-(4-phenoxy-phenyl)-acetamide The title compound was prepared according to the procedure described in Example 101 substituting (4-phenoxy-phenyl)-acetic acid for (4-benzyloxy-phenyl)-acetic acid. $^1$H NMR (300 MHz, DMSO-$d_6$) ppm 1.84 (m, 2H), 2.01 (m, 2H), 3.09 (m, 2H), 3.55 (m, 2H), 3.70 (m, 2H), 3.75 (s, 2H), 4.73 (t, J=6.24, 2H), 6.99 (m, 4H), 7.14 (m, 1H), 7.35 (m, 1H), 7.37–7.41 (m, 3H), 7.48 (m, 1H), 7.60 (m, 1H), 9.66 (s, 1H), 9.70 (s, 1H); MS (DCI/NH$_3$) m/z 475 [M+H]$^+$.

EXAMPLE 111

2-[4-(benzyloxy)phenyl]-N-[3-bromo-1-(2-pyrrolidin-1-ylethyl)-1H-indazol-4-yl]acetamide A mixture of 2-[4-(benzyloxy)phenyl]-N-[1-(2-pyrrolidin-1-ylethyl)-1H-indazol-4-yl]acetamide (Example 3, 0.200 g, 0.440 mmol) and NaOH (0.400 g, 10.0 mmol) in H$_2$O (6 mL) was added in methanol (6 mL) was placed in an ice-water bath for 15 minutes before pyridinium tribromide (0.470 g, 1.47 mmol) in MeOH (1.5 mL) was added. The reaction mixture was stirred at 0° C. for 5 hours after which the pH was adjusted to 7 with diluted HCl. The mixture was extracted with ethyl acetate, and the combined organic layer washed with $H_2O$ and concentrated under reduced pressure. The residue was purified by flash chromatography to provide the title compound. $^1$H NMR (300 MHz, DMSO-$d_6$) ppm 1.60 (m, 4H), 2.43 (m, 4H), 2.85 (t, 2H, J=6.44), 3.68 (s, 2H), 4.48 (t, 2H, J=6.44), 5.10 (s, 2H), 7.00 (d, 2H, J=8.47), 7.29–7.48 (m, 7H), 7.55 (s, 2H), 7.64 (s, 1H), 10.05 (s, 1H); MS (DCI/NH$_3$) m/z 533 [M+H]$^+$.

EXAMPLE 112

1-[3-chloro-1-(2-pyrrolidin-1-yl-ethyl)-1H-indazol-5-yl]-3-(4-phenoxy-phenyl)-urea

EXAMPLE 112A

3-chloro-5-nitro-1H-indazole

A mixture of NaOH (5.00 g, 125 mmol) in $H_2O$ (150 mL) was added 5-nitroindazole (5.00 g, 30.7 mmol), and the mixture was heated until a red solution formed. The mixture was cooled in an ice-water bath for 15 minutes, NaClO (60.0 mL, 5.25%, 45.0 mmol) was added and the mixture stirred at 0° C. for 5 hour after which the pH was adjusted to 7 with diluted HCl. The mixture was extracted with ethyl acetate, and the combined organic layer washed with $H_2O$ and concentrated under reduced pressure. The residue was purified by flash chromatography to provide the title compound (5.5 g, 92%). $^1$H NMR (300 MHz, DMSO-$d_6$) ppm 7.78 (m, 1H), 8.28 (m, 1H), 8.61 (m, 1H), MS (DCI/NH$_3$) m/Z 197[M+H]$^+$.

EXAMPLE 112B

3-chloro-5-nitro-1-(2-pyrrolidin-1-yl-ethyl)-1H-indazole

A mixture of 3-chloro-5-nitro-1H-indazole (1.5 g, 7.6 mmol) was treated with potassium carbonate (3.1 g, 23 mmol) in DMF (20 mL) for 30 minutes, after which 1-(2-chloro-ethyl)-pyrrolidine (1.9 g, 11 mmol) was added. The mixture was heated to 50° C. for 6 hours, cooled to room temperature, filtered through a plug of silica gel, which was rinsed with triethylamine/ethyl acetate (1/4). The filtrate was concentrated under reduced pressure and purified by flash chromatography (silica gel, triethylamine/ethyl acetate 1/30) to provide the title compound. $^1$H NMR (300 MHz, DMSO-$d_6$) ppm 1.60 (m, 4H), 2.45 (m, 4H), 2.89 (t, J=6.44, 2H), 4.58 (t, J=6.44, 2H), 8.00 (m, 1H), 8.30 (m, 1H), 8.60 (m, 1H); MS (DCI/NH$_3$) m/z 295 [M+H]$^+$.

EXAMPLE 112C

3-chloro-1-(2-pyrrolidin-1-yl-ethyl)-1H-indazol-5-ylamine

A mixture of 3-Chloro-5-nitro-1-(2-pyrrolidin-1-yl-ethyl)-1H-indazole (0.40 g, 1.4 mmol), iron powder (0.76 g, 14 mmol), and ammonium chloride (37 mg, 0.68 mmol) in 80% ethanol was heated to reflux for 3 hours, cooled to room temperature and concentrated under reduced pressure. The residue was stirred in triethylamine/ethyl acetate (1/4, 20 mL) for 15 minutes, filtered through a plug of silica gel, which was rinsed with triethylamine/ethyl acetate (1/4). The filtrate was concentrated under reduced pressure to provide the title compound (0.30 g, 84%). $^1$H NMR (300 MHz, DMSO-$d_6$) ppm 1.62 (m, 4H), 2.44 (m, 4H), 2.81 (t, J=6.44, 2H), 4.34 (t, J=6.44, 2H), 5.05 (s, 2H), 6.58 (m, 1H), 6.88 (m, 1H), 7.12 (m, 1H); MS (DCI/NH$_3$) m/z 265 [M+H]$^+$.

EXAMPLE 112

1-[3-chloro-1-(2-pyrrolidin-1-yl-ethyl)-1H-indazol-5-yl]-3-(4-phenoxy-phenyl)-urea The title compound was prepared according to the procedure described in Example 28 substituting 3-chloro-1-(2-pyrrolidin-1-yl-ethyl)-1H-indazol-5-ylamine for 1-(2-dimethylamino-ethyl)-1H-indazol-5-ylamine. $^1$H NMR (300 MHz, DMSO-$d_6$) ppm 1.85 (m, 2H), 2.01 (m, 2H), 3.10 (m, 2H), 3.54 (m, 2H), 3.72 (m, 2H), 4.73 (t, J=6.24, 2H), 6.95–6.99 (m, 4H), 7.00 (t, J=7.17, 1H), 7.37 (m, 1H), 7.47 (m, 1H), 7.74 (m, 1H), 7.51 (m, 2H), 7.98 (m, 1H), 9.04 (s, 1H), 9.16 (s, 1H), 9.68 (s, 1H); MS (DCI/NH$_3$) m/z 476 [M+H]$^+$.

EXAMPLE 113

1-[3-bromo-1-(2-pyrrolidin-1-yl-ethyl)-1H-indazol-5-yl]-3-(4-phenoxy-phenyl)-urea

EXAMPLE 113A

3-bromo-5-nitro-1H-indazole

A mixture of NaOH (2.0 g) in $H_2O$ (60 mL) was added 5-nitroindazole (2.0 g, 12 mmol), and the mixture was heated until a red solution formed. The mixture was placed in an ice-water bath for 15 minutes after which pyridinium tribromide (4.7 g, 15 mmol) in methanol (15 mL) was added. The mixture was stirred at 0° C. for 5 hours, the pH adjusted to 7 with diluted HCl and the mixture extracted with ethyl acetate. The combined organic layers were washed with $H_2O$, concentrated under reduced pressure and purified by flash chromatography to provide the title compound (1.6 g, 55% yield). $^1$H NMR (300 MHz, DMSO-$d_6$) ppm 7.80 (m, 1H), 8.28 (m, 1H), 8.50 (m, 1H), 14.09 (s, 1H), MS (DCI/NH$_3$) m/z 243[M+H]$^+$.

EXAMPLE 113B

3-bromo-5-nitro-1-(2-pyrrolidin-1-yl-ethyl)-1H-indazole

A mixture of 3-bromo-5-nitro-1H-indazole (1.8 g, 7.6 mmol) and potassium carbonate (3.1 g 22 mmol) in DMF (20 mL) was stirred for 30 minutes after which 1-(2-chloroethyl)-pyrrolidine (0.71 g, 4.2 mmol) was added. The mixture was heated to 50° C. for 6 hours, cooled to room temperature, filtered through a plug of silica gel which was rinsed with triethylamine/ethyl acetate (1/4). The combined filtrate was concentrated under reduced pressure and purified by flash chromatography (silica gel, triethylamine/ethyl acetate 1/30) to provide the title compound (1.9 g, 76%). $^1$H NMR (300 MHz, DMSO-$d_6$) ppm 1.60 (m, 4H), 2.46 (m, 4H), 2.90 (t, 2H, J=6.44), 4.60 (t, J=6.44, 2H), 8.00 (m, 1H), 8.30 (m, 1H), 8.48 (m, 1H); MS (DCI/NH$_3$) m/z 339 [M+H]$^+$.

EXAMPLE 113C

3-bromo-1-(2-pyrrolidin-1-yl-ethyl)-1H-indazol-5-ylamine

A mixture of 3-bromo-5-nitro-1-(2-pyrrolidin-1-yl-ethyl)-1H-indazole (1.9 g, 5.6 mmol), iron powder (3.1 g, 56 mmol), and ammonium chloride (0.15 g, 2.8 mmol) in 80% ethanol was heated to reflux for 3 hours, cooled to room temperature and concentrated under reduced pressure. The residue was taken up and stirred in triethylamine/ethyl acetate (1/4, 20 mL) for 15 minutes, filtered through a plug of silica gel, which was rinsed with triethylamine/ethyl acetate (1/4), and the filtrate concentrated under reduced pressure to provide the title compound (1.2 g, 70%). $^1$H NMR (300 MHz, DMSO-$d_6$) ppm 1.62 (m, 4H), 2.44 (m, 4H), 2.81 (t, 2H, J=6.44), 4.36 (t, J=6.44, 2H), 5.05 (s, 2H), 6.52 (m, 1H), 6.88 (m, 1H), 7.42 (m, 1H); MS (DCI/NH$_3$) m/z 309 [M+H]$^+$.

EXAMPLE 113

1-[3-bromo-1-(2-pyrrolidin-1-yl-ethyl)-1H-indazol-5-yl]-3-(4-phenoxy-phenyl)-urea The title compound was prepared according to the procedure described in Example 28 substituting 3-bromo-1-(2-pyrrolidin-1-yl-ethyl)-1H-indazol-5-ylamine for 1-(2-dimethylamino-ethyl)-1H-indazol-5-ylamine. $^1$H NMR (300 MHz, DMSO-$d_6$) ppm 1.85 (m, 2H), 2.01(m, 2H), 3.09 (m, 2H), 3.54 (m, 2H), 3.72 (m, 2H), 4.75 (t, J=6.24, 2H), 6.95–7.00 (m, 4H), 7.09 (m, 1H), 7.37 (m, 2H), 7.47 (m, 1H), 7.51 (m, 2H), 7.74 (m, 1H), 7.92 (m, 1H), 8.99 (s, 1H), 9.12 (s, 1H); MS (DCI/NH$_3$) m/z 520 [M+H]$^+$.

EXAMPLE 114

N-[3-bromo-1-(2-pyrrolidin-1-yl-ethyl)-1H-indazol-5-yl]-2-(4-phenoxy-phenyl)-acetamide The title compound was prepared according to the procedure described in Example 27 substituting 3-bromo-1-(2-pyrrolidin-1-yl-ethyl)-1H-indazol-5-ylamine for 1-(2-dimethylamino-ethyl)-1H-indazol-5-ylamine. $^1$H NMR (300 MHz, DMSO-$d_6$) ppm 1.83 (m, 2H), 2.01 (m, 2H), 3.08 (m, 2H), 3.52 (m, 2H), 3.67 (s, 2H), 3.72 (m, 2H), 4.75 (t, J=6.24, 2H), 6.98–7.00 (m, 4H), 7.13 (m, 1H), 7.36–7.40 (m, 4H), 7.60 (m, 1H), 7.77 (m, 1H), 8.08 (m, 1H), 10.38 (s, 1H); MS (DCI/NH$_3$) m/z 512 [M+H]$^+$.

EXAMPLE 115

N-[3-chloro-1-(2-pyrrolidin-1-yl-ethyl)-1H-indazol-6-yl]-2-(4-phenoxy-phenyl)-acetamide

EXAMPLE 115A

3-chloro-6-nitro-1H-indazole

A mixture of NaOH (5.0 g) in H$_2$O (150 mL) was added 5-nitroindazole (5.0 g, 31 mmol), and the mixture heated until a red solution formed. The mixture was placed in an ice-water bath for 15 minutes after which NaClO (60 mL, 5.25%, 45 mmol) was added. The mixture was stirred at 0° C. for 5 hours after which the pH was adjusted to 7 with diluted HCl. The mixture was extracted with ethyl acetate, and the combined organic layer was washed with H$_2$O and concentrated under reduced pressure. The residue was purified by flash chromatography to provide the title compound (5.5 g, 92%). $^1$H NMR (300 MHz, DMSO-$d_6$) ppm 7.93 (m, 1H), 8.02 (m, 1H), 8.50 (m, 1H), 14.01 (s, 1H); MS (DCI/NH$_3$) m/Z 197 [M+H]$^+$.

EXAMPLE 115B

3-chloro-6-nitro-1-(2-pyrrolidin-1-yl-ethyl)-1H-indazole

A mixture of 3-chloro-6-nitro-1H-indazole (2.4 g, 12 mmol) was treated with potassium carbonate (5.0 g, 36 mmol) in DMF (40 mL) for about 30 minutes, after which 1-(2-chloro-ethyl)-pyrrolidine (3.1 g, 18 mmol) was added. The mixture was heated to 50° C. for 6 hours, cooled to room temperature and filtered through a plug of silica gel which was rinsed with triethylamine/ethyl acetate (1/4). The combined filtrate was concentrated under reduced pressure and purified by flash chromatography (silica gel, triethylamine/ethyl acetate 1/30) to provide the title compound (2.3 g, 66%). $^1$H NMR (300 MHz, DMSO-$d_6$) ppm 1.61 (m, 4H), 2.47 (m, 4H), 2.89 (t, J=6.44, 2H), 4.67 (t, J=6.44, 2H), 7.90 (m, 1H), 8.01 (m, 1H), 8.86 (m, 1H); MS (DCI/NH$_3$) m/z 295 [M+H]$^+$.

EXAMPLE 115C

3-chloro-1-(2-pyrrolidin-1-yl-ethyl)-1H-indazol-6-ylamine

A mixture of 3-chloro-6-nitro-1-(2-pyrrolidin-1-yl-ethyl)-1H-indazole (2.3 g, 7.8 mmol), iron powder (3.5 g, 62 mmol), and ammonium chloride (0.21 g, 3.9 mmol) in 80% Ethanol was heated to reflux for 3 hours, cooled to room temperature, and concentrated under reduced pressure. The residue was stirred in triethylamine/ethyl acetate (1/4, 20 mL) for 15 minutes, filtered through a plug of silica gel, which was rinsed with triethylamine/ethyl acetate (1/4). The filtrate was concentrated under reduced pressure to provide the title compound (1.7 g, 80%). $^1$H NMR (300 MHz, DMSO-$d_6$) ppm 1.64 (m, 4H), 2.45 (m, 4H), 2.78 (t, J=6.44, 2H), 4.21 (t, J=6.44, 2H), 5.56 (s, 2H), 6.48 (m, 1H), 6.58 (m, 1H), 7.25 (m, 1H); MS (DCI/NH$_3$) m/z 265 [M+H]$^+$.

EXAMPLE 115

N-[3-chloro-1-(2-pyrrolidin-1-yl-ethyl)-1H-indazol-6-yl]-2-(4-phenoxy-phenyl)-acetamide The title compound was prepared according to the procedure described in Example 27 substituting 3-chloro-1-(2-pyrrolidin-1-yl-ethyl)-1H-indazol-6-ylamine for 1-(2-dimethylamino-ethyl)-1H-indazol-5-ylamine. $^1$H NMR (300 MHz, DMSO-$d_6$) ppm 1.81 (m, 2H), 2.00 (m, 2H), 3.07 (m, 2H), 3.52 (m, 2H), 3.69 (t, J=6.24, 2H), 3.71 (s, 2H), 4.65 (t, J=6.24, 2H), 6.99 (m, 4H), 7.13 (m, 1H), 7.22 (m, 1H), 7.36–7.40 (m, 4H), 7.65 (m, 1H), 8.34 (s, 1H), 10.53 (s, 1H); MS (DCI/NH$_3$) m/z 475 [M+H]$^+$.

EXAMPLE 116

2-[4-(benzyloxy)phenyl]-N-[3-bromo-1-(2-pyrrolidin-1-ylethyl)-1H-indazol-6-yl]acetamide

EXAMPLE 116A

3-bromo-6-nitro-1H-indazole

A mixture of NaOH (2.0 g, 50 mmol) in H$_2$O (60 mL) was added 6-nitroindazole (2.0 g, 12 mmol) and the suspension heated until a red solution formed. The mixture was placed in an ice-water bath for 15 minutes after which pyridinium tribromide (4.7 g, 15 mmol) in MeOH (15 mL) was added. The mixture was stirred at 0° C. for 5 hours after which the pH was adjusted to 7 with diluted HCl. The mixture was extracted with ethyl acetate, and the combined organic layer washed with $H_2O$ and concentrated under reduced pressure. The residue was purified by flash chromatography to provide the title compound. $^1$H NMR (300 MHz, DMSO-$d_6$) δ ppm 7.84 (m, 1H), 8.02 (m, 1H), 8.50 (m, 1H), 14.16 (s, 1H); MS (DCI/NH$_3$) m/z 243[M+H]$^+$.

EXAMPLE 116B 3-bromo-6-nitro-1-(2-pyrrolidin-1-yl-ethyl)-1H-indazole

A mixture of 3-bromo-6-nitro-1H-indazole (1.0 g, 4.1 mmol) and potassium carbonate (2.9 g 21 mmol) in DMF (20 mL) was stirred for 30 minutes after which 1-(2-chloroethyl)-pyrrolidine (1.8 g, 10 mmol) was added. The mixture was heated to 50° C. for 6 hours, cooled to room temperature and filtered through a plug of silica gel which was rinsed with triethylamine/ethyl acetate (1/4). The filtrate was concentrated under reduced pressure and purified by flash chromatography (silica gel, triethylamine/ethyl acetate 1/30) to provide the title compound (900 mg, 64%). $^1$H NMR (300 MHz, DMSO-$d_6$) ppm 1.61 (m, 4H), 2.47 (m, 4H), 2.90 (t, 2H, J=6.44), 4.69 (t, J=6.44, 2H), 7.82 (m, 1H), 8.02 (m, 1H), 8.86 (m, 1H); MS (DCI/NH$_3$) m/z 339 [M+H]$^+$.

EXAMPLE 116C 3-bromo-1-(2-pyrrolidin-1-yl-ethyl)-1H-indazol-6-ylamine

A mixture of 3-bromo-6-nitro-1-(2-pyrrolidin-1-yl-ethyl)-1H-indazole (0.90 g, 2.7 mmol), iron powder (1.5 g, 26 mmol), and ammonium chloride (73 mg, 1.3 mmol) in 80% ethanol was heated to reflux for 3 hours, cooled to room temperature and concentrated under reduced pressure. The residue was taken up and stirred in triethylamine/ethyl acetate (1/4, 20 mL) for about 15 minutes, filtered through a plug of silica gel, which was rinsed with triethylamine/ ethyl acetate (1/4), and the filtrate concentrated under reduce pressure to provide the title compound (0.78 g, 95%). $^1$H NMR (300 MHz, DMSO-$d_6$) ppm 1.64 (m, 4H), 2.46 (m, 4H), 2.79 (t, 2H, J=6.44), 4.23 (t, J=6.44, 2H), 5.56 (s, 2H), 6.49 (m, 1H), 6.58 (m, 1H), 7.16 (m, 1H); MS (DCI/NH$_3$) m/z 309 [M+H]$^+$.

EXAMPLE 116

2-[4-(benzyloxy)phenyl]-N-[3-bromo-1-(2-pyrrolidin-1-ylethyl)-1H-indazol-6-yl]acetamide The title compound was prepared according to the procedure for Example 109, substituting 3-bromo-1-(2-pyrrolidin-1-yl-ethyl)-1H-indazol-6-ylamine for 3-bromo-1-(2-pyrrolidin-1-yl-ethyl)-1H-indazol-4-ylamine. $^1$H NMR (300 MHz, DMSO-$d_6$) δ ppm 1.61 (m, 4H), 2.44 (m, 4H), 2.82 (t, 2H, J=6.44), 3.62 (s, 2H), 4.37 (t, 2H, J=6.44), 5.09 (s, 2H), 6.97 (m, 2H), 7.20–7.50 (m, 9H), 8.19 (s, 1H), 10.39(s, 1H); MS (DCI/NH$_3$) m/z 533 [M+H]$^+$.

EXAMPLE 117

N-[3-bromo-1-(2-pyrrolidin-1-yl-ethyl)-1H-indazol-6-yl]-2-(4-phenoxy-phenyl)-acetamide The title compound was prepared according to the procedure described in Example 27 substituting 3-bromo-1-(2-pyrrolidin-1-yl-ethyl)-1H-indazol-6-ylamine for 1-(2-dimethylamino-ethyl)-1H-indazol-5-ylamine. $^1$H NMR (300 MHz, DMSO-$d_6$) ppm 1.77 (m, 4H), 2.88 (m, 4H), 3.25 (m, 2H), 3.70 (s, 2H), 4.53 (m, 2H), 6.99–7.01 (m, 4H), 7.13 (m, 1H), 7.23 (m, 1H), 7.35–7.40 (m, 4H), 7.53 (m, 1H), 8.28 (s, 1H), 10.49 (s, 1H); MS (DCI/NH$_3$) m/z 512 [M+H]$^+$.

EXAMPLE 118

1-(4-phenoxyphenyl)-3-[1-(2-pyrrolidin-1-ylethyl)-1H-indazol-5-yl]-1,3-dihydro-2H-imidazol-2-one

EXAMPLE 118A

N-(2,2-dimethoxyethyl)-1-(2-pyrrolidin-1-ylethyl)-1H-indazol-5-amine

To a solution of 1-(2-pyrrolidin-1-yl-ethyl)-1H-indazol-5-ylamine (1.14 g, 0.497 mmol) in 62 mL of dry THF was added 2.04 mL of dimethyl glyoxal in MTBE (45% glyoxal by weight). A slurry of NaBH(OAc)$_3$ (1.66 g, 7.83 mmol) in THF (10 mL) was slowly added via addition funnel over 60 minutes, and the mixture stirred at room temperature. After 12 hours, an additional equivalent of NaBH(OAc)$_3$ was added. After an additional 12 hours, the mixture was quenched with saturated. NaHCO$_3$, filtered, and the solvents removed under reduced pressure. The residue was purified via column chromatography eluting with 5–15% Et$_3$N in EtOAc to provide 650 mg (2.04 mmol) of the title compound. $^1$H NMR (300 MHz, DMSO-D6) δ ppm 1.50–1.74 (m, 4 H) 2.33–2.46 (m, 4 H) 2.81 (t, J=6.78 Hz, 2 H) 3.14 (t, J=5.76 Hz, 2 H) 3.33 (t, 6 H) 4.38 (t, J=6.78 Hz, 2 H) 4.54 (t, J=5.42 Hz, 1 H) 5.26 (t, J=6.10 Hz, 1 H) 6.63–6.73 (m, J=2.03 Hz, 1 H) 6.91 (dd, J=8.98, 2.20 Hz, 1 H) 7.28–7.46 (m, J=8.81 Hz, 1 H) 7.64–7.78 (m, 1 H); MS (ESI) m/z 319 [M+H]$^+$.

EXAMPLE 118

1-(4-phenoxyphenyl)-3-[1-(2-pyrrolidin-1-ylethyl)-1H-indazol-5-yl]-1,3-dihydro-2H-imidazol-2-one N-(2,2-Dimethoxyethyl)-1-(2-pyrrolidin-1-ylethyl)-1H-indazol-5-amine (0.400 g, 1.25 mmol) was dissolved in 8.4 mL THF and 0.265 g of phenoxyphenylisocyanate (1.25 mmol) was added. The reaction solution was heatedt to reflux for one hour. The reaction mixture was cooled to room temperature, 5 equivalents of HCl (1M) was added, and the mixture heated to reflux. After 2 hours the solvents were removed under reduced pressure, the residue dissolved in EtOAc and washed with saturated NaHCO$_3$ (×3), brine, water, dried (MgSO$_4$) and filtered. The solvents were removed under reduced pressure and the residue purified by RP-HPLC to provide the title compound. $^1$H NMR (300 MHz, DMSO-$d_6$) ppm 8.12 (d, 1H, J=0.68), 8.01 (d, 1H, J=1.36), 7.80 (d, 1H, J=9.16), 7.76 (d, 2H, J=8.81), 7.70 (dd, 1H, $J_1$=9.16, $J_2$=2.03), 7.42 (m, 2H), 7.25 (s, 2H), 7.03–7.09 (m, 5H), 4.54 (t, 2H, J=6.44), 2.89 (t, 2H, J=6.45), 2.46 (m, 4H), 1.62 (m, 4H); MS (ESI) m/z 466 [M+H]$^+$.

EXAMPLE 119

1-(4-phenoxyphenyl)-3-[1-(2-pyrrolidin-1-ylethyl)-1H-indazol-5-yl]imidazolidin-2-one 1-(4-phenoxyphenyl)-3-[1-(2-pyrrolidin-1-ylethyl)-1H-indazol-5-yl]-1,3-dihydro-2H-imidazol-2-one (Example 118) (0.100 g, 0.215 mmol) was dissolved in 20 mL of AcOH and 100 mg of Pd/C (10% mol/mol) was added. The mixture was subjected to an atmosphere of hydrogen gas at a pressure of 60 psi in a Parr shaker apparatus, and shaken at room temperature for 6 hours. The mixture was filtered through celite, and the solvents removed under reduced pressure. The residue was purified by RP-HPLC to provide the title compound. $^1$H NMR (300 MHz, DMSO-D6) δ ppm 1.52–1.77 (m, 4 H) 2.34–2.50 (m, 4 H) 2.87 (t, J=6.61 Hz, 2 H) 3.88–4.13 (m, 4 H) 4.50 (t, J=6.61 Hz, 2 H) 6.93–7.02 (m, J=7.80 Hz, 2 H) 7.03–7.15 (m, 3 H) 7.33–7.45 (m, J=8.65, 7.29 Hz, 2 H) 7.61–7.72 (m, 3 H) 7.72–7.78 (m, J=2.03 Hz, 1 H) 7.79–7.89 (m, 1 H) 8.02 (s, 1 H); MS (ESI) m/z 468 [M+H]$^+$.

What is claimed is:

1. A compound of formula (I),

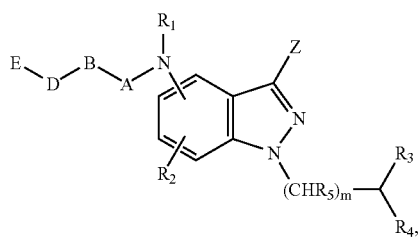

or a therapeutically suitable salt or prodrug thereof, wherein

A is selected from the group consisting of —C(O)—, —S(O)—, —S(O)$_2$—, —C(=NR$_a$)— and —C(=S)—;

B is selected from the group consisting of alkylene, alkenyl, carbonylalkyl, cycloalkyl, —NR$_b$— and —NR$_b$-alkyl;

D is a bond or is selected from the group consisting of alkylene, aryl, arylalkyl, heterocycle and heterocyclealkyl;

E is selected from the group consisting of alkyl, alkyl-C(O)—, alkyl-C(O)—NH—, alkyl-NH—, alkyl-NH—C(O)—, alkyl-NH—S(O)$_2$—, alkoxy, alkyl-S—, alkyl-S(O)$_2$—, alkyl-S(O)$_2$—NH—, aryl, aryl-C(O)—, aryl-C(O)—NH—, aryl-C=N—O—, aryl-NH—, aryl-NH—C(O)—, aryl-NH—S(O)$_2$—, aryloxy, aryl-S—, aryl-S-alkyl-C(O)—, aryl-S(O)$_2$—, aryl-S(O)$_2$—NH—, arylalkyl-C(O)—, arylalkyl-C(O)—NH—, arylalkyl-NH—, arylalkyl-NH—C(O)—, arylalkyl-NH—S(O)$_2$—, arylalkoxy, arylalkyl-S—, arylalkyl-S(O)$_2$—, arylalkyl-S(O)$_2$—NH—, cycloalkyl, cycloalkyl-C(O)—, cycloalkyl-C(O)—NH—, cycloalkyl-NH—, cycloalkyl-NH—C(O)—, cycloalkyl-NH—S(O)$_2$—, cycloalkoxy, cycloalkyl-S—, cycloalkyl-S(O)$_2$—, cycloalkyl-S(O)$_2$—NH—, cycloalkenyl, cycloalkenylalkyl, cycloalkenyl-C(O)—, cycloalkenyl-C(O)—NH—, cycloalkenyl-NH—, cycloalkenyl-NH—C(O)—, cycloalkenyl-NH—S(O)$_2$—, cycloalkenyloxy, cycloalkenyl-S—, cycloalkenyl-S(O)$_2$—, cycloalkenyl-S(O)$_2$—NH—, heterocycle, heterocycle-C(O)—, heterocycle-C(O)—NH—, heterocycle-NH—, heterocycle-NH—C(O)—, heterocycle-NH—S(O)$_2$—, heterocycle-O—, heterocycle-S—, heterocycle-S(O)$_2$—, heterocycle-S(O)$_2$—NH—, heterocyclealkyl-C(O)—, heterocyclealkyl-C(O)—NH—, heterocyclealkyl-NH—, heterocyclealkyl-NH—C(O)—, heterocyclealkyl-NH—S(O)$_2$—, heterocyclealkyl-O—, heterocyclealkyl-S—, heterocyclealkyl-S(O)$_2$— and heterocyclealkyl-S(O)$_2$—NH—, R$_1$ is selected from the group consisting of hydrogen and alkyl;

R$_2$ is selected from the group consisting of hydrogen, halogen, alkyl and alkoxy;

R$_3$ is R$_c$R$_d$N—;

R$_4$ is selected from the group consisting of hydrogen and alkyl, or R$_4$ and R$_c$ taken together with any intervening atoms form a heterocycle;

each occurrence of R$_5$ is independently selected from the group consisting of hydrogen and alkyl;

R$_a$ is selected from the group consisting of hydrogen and alkyl;

R$_b$ is selected from the group consisting of hydrogen and alkyl, or R$_b$ and R$_1$ taken together with any intervening atoms form a heterocycle;

R$_c$ and R$_d$ are each independently selected from the group consisting of hydrogen, alkyl, aryl, arylalkyl, cycloalkyl, cycloalkenylalkyl, heterocycle, heterocyclealkyl and hydroxyalkyl, or R$_c$ and R$_d$ taken together with any intervening atoms form a heterocycle;

Z is selected from the group consisting of hydrogen, alkyl and halogen; and m is 1, 2 or 3;

provided that:

if B is NR$_b$- or NR$_b$-alkyl, then

D is selected from the group consisting of alkyl, aryl, arylalkyl, heterocycle and heterocyclealkyl; and if A is C(O), B is NR$_b$, D is aryl, m=1, Z is H, R$_1$ is H, R$_4$ is H, R$_2$ is H, and R$_c$ and R$_d$ are alkyl, then E cannot be heteroaryl-O.

2. The compound according to claim 1 wherein

A is —C(O)—;

B is selected from the group consisting of alkylene, alkenyl, —NR$_b$— and —NR$_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, alkyl-S(O)$_2$—, aryl-C(O)—, aryl-C=N—O—, aryl-NH—, aryloxy, aryl-S—, aryl-S-alkyl-C(O)—, aryl-S(O)$_2$—, arylalkyl-C(O)—, arylalkyl-NH—, arylalkoxy, arylalkyl-S(O)$_2$—, cycloalkyl, cycloalkyl-C(O)—, cycloalkyl-NH—, cycloalkoxy, cycloalkyl-S(O)$_2$—, cycloalkenylalkyl, heterocycle-C(O)—, heterocycle-NH—, heterocycle-O—, heterocycle-S(O)$_2$—, heterocyclealkyl-C(O)—, heterocyclealkyl-NH—, heterocyclealkyl-O— and heterocyclealkyl-S(O)$_2$—;

R$_1$ is selected from the group consisting of hydrogen and alkyl;

R$_2$ is selected from the group consisting of hydrogen, halogen, alkyl and alkoxy;

R$_3$ is R$_c$R$_d$N—;

R$_4$ is selected from the group consisting of hydrogen and alkyl, or R$_4$ and R$_c$ taken together with any intervening atoms form a heterocycle;

each occurrence of R$_5$ is independently selected from the group consisting of hydrogen and alkyl;

R$_a$ is selected from the group consisting of hydrogen and alkyl;

R$_b$ is selected from the group consisting of hydrogen and alkyl, or R$_b$ and R$_1$ taken together with any intervening atoms form a heterocycle;

R$_c$ and R$_d$ are each independently selected from the group consisting of hydrogen, alkyl, aryl, arylalkyl, cycloalkyl, cycloalkenylalkyl, heterocycle, heterocyclealkyl and hydroxyalkyl, or $R_c$ and $R_d$ taken together with any interveneing atoms form a heterocycle;

Z is selected from the group consisting of hydrogen, alkyl and halogen; and m is 1, 2 or 3;

provided that:

if B is $NR_b$— or $NR_b$-alkyl, then

D is selected from the group consisting of alkyl, aryl, arylalkyl, heterocycle and heterocyclealkyl; and if A is C(O), B is $NR_b$, D is aryl, m=1, Z is H, $R_1$ is H, $R_4$ is H, $R_2$ is H, and $R_c$ and $R_d$ are alkyl, then E cannot be heteroaryl-O.

3. The compound according to claim 1 wherein

A is —C(O)—;

B is selected from the group consisting of alkylene, alkenyl, —$NR_b$— and —$NR_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—;

$R_1$ is selected from the group consisting of hydrogen and alkyl;

$R_2$ is selected from the group consisting of hydrogen, halogen, alkyl and alkoxy;

$R_3$ is $R_cR_dN$—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_a$ is selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ are each independently selected from the group consisting of hydrogen, alkyl, aryl, arylalkyl, cycloalkyl, cycloalkenylalkyl, heterocycle, heterocyclealkyl and hydroxyalkyl; or $R_c$ and $R_d$ taken together with any intervening atoms form a heterocycle;

Z is selected from the group consisting of hydrogen, alkyl and halogen; and m is 1, 2 or 3;

provided that:

if B is $NR_b$— or $NR_b$-alkyl, then

D is selected from the group consisting of alkyl, aryl, arylalkyl, heterocycle and heterocyclealkyl; and if A is C(O), B is $NR_b$, D is aryl, m=1, Z is H, $R_1$ is H, $R_4$ is H, $R_2$ is H, and $R_c$ and $R_d$ are alkyl, then E cannot be heteroaryl-O.

4. The compound according to claim 1 wherein

A is —C(O)—;

B is selected from the group consisting of alkylene, alkenyl, —$NR_b$— and —$NR_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH— and heterocyclealkyl-O—;

$R_1$ is selected from the group consisting of hydrogen and alkyl;

$R_2$ is selected from the group consisting of hydrogen, halogen, alkyl and alkoxy;

$R_3$ is $R_cR_dN$—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_a$ is selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ are each independently selected from the group consisting of hydrogen, alkyl, aryl, arylalkyl, cycloalkyl, cycloalkenylalkyl, heterocycle, heterocyclealkyl and hydroxyalkyl; or $R_c$ and $R_d$ taken together with any intervening atoms form a heterocycle;

Z is selected from the group consisting of hydrogen, alkyl and halogen; and m is 1, 2 or 3;

provided that:

if B is $NR_b$— or $NR_b$-alkyl, then

D is selected from the group consisting of alkyl, aryl, arylalkyl, heterocycle and heterocyclealkyl; and if A is C(O), B is $NR_b$, D is aryl, m=1, Z is H, $R_1$ is H, $R_4$ is H, $R_2$ is H, and $R_c$ and $R_d$ are alkyl, then E cannot be heteroaryl-O.

5. The compound according to claim 4, wherein the compound is selected from the group consisting of N-[1-(2-dimethylamino-ethyl)-1H-indazol-4-yl]-2-(4-phenoxy-phenyl)-acetamide;

N-[1-(2-dimethylamino-ethyl)-1H-indazol-5-yl]-2-(4-phenoxy-phenyl)-acetamide;

1-[1-(2-dimethylamino-ethyl)-1H-indazol-5-yl]-3-(4-phenoxy-phenyl)-urea;

N-{1-[2-(diethylamino)ethyl]-1H-indazol-5-yl}-N'-(4-phenoxyphenyl)urea;

N-(1-{2-[isobutyl(methyl)amino]ethyl}-1H-indazol-5-yl)-N'-(4-phenoxyphenyl)urea;

N-(1-{2-[isopropyl(methyl)amino]ethyl}-1H-indazol-5-yl)-N'-(4-phenoxyphenyl)urea;

N-[1-(2-dimethylamino-ethyl)-1H-indazol-6-yl]-2-(4-phenoxy-phenyl)-acetamide;

2-(4-benzyloxy-phenyl)-N-[1-(2-dimethylamino-ethyl)-1H-indazol-6-yl]-acetamide;

N-{1-[2-(cyclopentylamino)ethyl]-1H-indazol-6-yl}-2-(4-phenoxyphenyl)acetamide;

N-(1-{2-[(2-morpholin-4-ylethyl)amino]ethyl}-1H-indazol-6-yl)-2-(4-phenoxyphenyl)acetamide;

2-(4-phenoxyphenyl)-N-(1-{2-[(tetrahydrofuran-2-ylmethyl)amino]ethyl}-1H-indazol-6-yl)acetamide;

N-(1-{2-[(2-cyclohex-1-en-1-ylethyl)amino]ethyl}-1H-indazol-6-yl)-2-(4-phenoxyphenyl)acetamide;

N-{1-[3-(diisopropylamino)propyl]-1H-indazol-6-yl}-2-(4-phenoxyphenyl)acetamide;

N-{1-[3-(cyclopentylamino)propyl]-1H-indazol-6-yl}-2-(4-phenoxyphenyl)acetamide;

N-(1-{3-[cyclohexyl(methyl)amino]propyl}-1H-indazol-6-yl)-2-(4-phenoxyphenyl)acetamide;

N-{1-[3-(diisobutylamino)propyl]-1H-indazol-6-yl}-2-(4-phenoxyphenyl)acetamide; and 2-[4-(benzyloxy)phenyl]-N-[1-(3-dimethylamino-propyl)-1H-indazol-6-yl]acetamide.

6. The compound according to claim 1 wherein

A is —C(O)—;

B is selected from the group consisting of alkylene, alkenyl, —$NR_b$— and —$NR_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—;

$R_1$ is selected from the group consisting of hydrogen and alkyl;

$R_2$ is selected from the group consisting of hydrogen, halogen, alkyl and alkoxy;

$R_3$ is $R_cR_dN$—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ taken together with the atoms to which they are attached form a 4 membered heterocycle;

Z is selected from the group consisting of hydrogen, alkyl and halogen; and m is 1, 2 or 3;

provided that:

if B is $NR_b$— or $NR_b$-alkyl, then

D is selected from the group consisting of alkyl, aryl, arylalkyl, heterocycle and heterocyclealkyl.

7. The compound according to claim 1 that is N-[1-(2-azetidin-1-ylethyl)-1H-indazol-5-yl]-N'-(4-phenoxyphenyl)urea.

8. The compound according to claim 1 wherein

A is —C(O)—;

B is selected from the group consisting of alkylene, alkenyl, —$NR_b$— and —$NR_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—;

$R_1$ is selected from the group consisting of hydrogen and alkyl;

$R_2$ is selected from the group consisting of hydrogen, halogen, alkyl and alkoxy;

$R_3$ is $R_cR_dN$—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ taken together with the atoms to which they are attached form a 5 membered heterocycle;

Z is selected from the group consisting of hydrogen, alkyl and halogen; and m is 1, 2 or 3;

provided that:

if B is $NR_b$— or $NR_b$-alkyl, then

D is selected from the group consisting of alkyl, aryl, arylalkyl, heterocycle and heterocyclealkyl.

9. The compound according to claim 1 wherein

A is —C(O)—;

B is selected from the group consisting of alkylene, alkenyl, —$NR_b$— and —$NR_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—;

$R_1$ is selected from the group consisting of hydrogen and alkyl;

$R_2$ is selected from the group consisting of hydrogen, halogen, alkyl and alkoxy;

$R_3$ is $R_cR_dN$—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ taken together with the atoms to which they are attached form

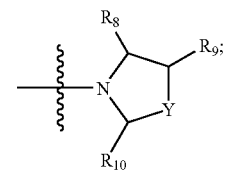

Y is selected from the group consisting of —O—, —$NR_j$—, —$CHR_j$— and —C(O)—;

Z is selected from the group consisting of hydrogen, alkyl and halogen;

$R_8$ is selected from the group consisting of hydrogen and alkyl;

$R_9$ and $R_{10}$ are each individually selected from the group consisting of oxo, hydrogen and alkyl; and m is 1, 2 or 3;

provided that:

if B is $NR_b$— or $NR_b$-alkyl, then

D is selected from the group consisting of alkyl, aryl, arylalkyl, heterocycle and heterocyclealkyl.

10. The compound according to claim 9, wherein the compound is selected from the group consisting of N-(2-oxo-2-{[1-(2-pyrrolidin-1-ylethyl)-1H-indazol-4-yl]amino}ethyl)-4-phenoxybenzamide;
2-[(4-phenoxybenzyl)amino]-N-[1-(2-pyrrolidin-1-ylethyl)-1H-indazol-4-yl]acetamide;
2-[4-(benzyloxy)phenyl]-N-[1-(2-pyrrolidin-1-ylethyl)-1H-indazol-4-yl]acetamide;
2-(3-phenoxyphenyl)-N-[1-(2-pyrrolidin-1-ylethyl)-1H-indazol-4-yl]acetamide;
2-(4-phenoxyphenyl)-N-[1-(2-pyrrolidin-1-ylethyl)-1H-indazol-4-yl]acetamide;
3-(4-phenoxyphenyl)-N-[1-(2-pyrrolidin-1-ylethyl)-1H-indazol-4-yl]propanamide;
2-{4-[(2,3-difluorobenzyl)oxy]phenyl}-N-[1-(2-pyrrolidin-1-ylethyl)-1H-indazol-4-yl]acetamide;
2-[4-(benzyloxy)phenyl]-N-(1-{2-[(2R)-2-methylpyrrolidin-1-yl]ethyl}-1H-indazol-4-yl)acetamide;
2-[4-(benzyloxy)phenyl]-N-[1-(2-pyrrolidin-1-ylethyl)-1H-indazol-5-yl]acetamide;
3-(4-phenoxyphenyl)-N-[1-(2-pyrrolidin-1-ylethyl)-1H-indazol-5-yl]propanamide;
2-(3-phenoxyphenyl)-N-[1-(2-pyrrolidin-1-ylethyl)-1H-indazol-5-yl]acetamide;
4-(4-chlorophenyl)-N-[1-(2-pyrrolidin-1-ylethyl)-1H-indazol-5-yl]cyclohexanecarboxamide;
3-(4-phenoxyphenyl)-N-[1-(2-pyrrolidin-1-ylethyl)-1H-indazol-5-yl]propanamide;
2-(4-phenoxyphenyl)-N-[1-(2-pyrrolidin-1-ylethyl)-1H-indazol-5-yl]acetamide;
(2E)-3-(1,1'-biphenyl-4-yl)-N-[1-(2-pyrrolidin-1-ylethyl)-1H-indazol-5-yl]acrylamide;
N-(4-phenoxyphenyl)-N'-[1-(2-pyrrolidin-1-ylethyl)-1H-indazol-5-yl]urea;
N-(5-phenylthien-2-yl)-N'-[1-(2-pyrrolidin-1-ylethyl)-1H-indazol-5-yl]urea;
1-(4-phenylamino-phenyl)-3-[1-(2-pyrrolidin-1-ylethyl)-1H-indazol-5-yl]-urea;
N-{1-[2-(2-methylpyrrolidin-1-yl)ethyl]-1H-indazol-5-yl}-N'-(4-phenoxyphenyl)urea;
N-(1-{2-[(2S)-2-(methoxymethyl)pyrrolidin-1-yl]ethyl}-1H-indazol-5-yl)-N'-(4-phenoxyphenyl)urea;
N-(1-{2-[(2S)-2-(hydroxymethyl)pyrrolidin-1-yl]ethyl}-1H-indazol-5-yl)-N'-(4-phenoxyphenyl)urea;
N-{1-[2-(2,3-dihydro-1H-indol-1-yl)ethyl]-1H-indazol-5-yl}-N'-(4-phenoxyphenyl)urea;
N-((3R)-1-{2-[5-({[(4-phenoxyphenyl)amino]carbonyl}amino)-1H-indazol-1-yl]ethyl}pyrrolidin-3-yl)acetamide;
N-{1-[2-(3-hydroxypyrrolidin-1-yl)ethyl]-1H-indazol-5-yl}-N'-(4-phenoxyphenyl)urea;
2-[4-(benzyloxy)phenyl]-N-[1-(2-pyrrolidin-1-ylethyl)-1H-indazol-6-yl]acetamide;
2-(3-phenoxyphenyl)-N-[1-(2-pyrrolidin-1-ylethyl)-1H-indazol-6-yl]acetamide;
4-(1,1'-biphenyl-4-yl)-4-oxo-N-[1-(2-pyrrolidin-1-ylethyl)-1H-indazol-6-yl]butanamide;
3-(2-naphthylthio)-N-[1-(2-pyrrolidin-1-ylethyl)-1H-indazol-6-yl]propanamide;
2-(5-{[(4-methylphenyl)thio]acetyl}thien-2-yl)-N-[1-(2-pyrrolidin-1-ylethyl)-1H-indazol-6-yl]acetamide;
3-(4-phenoxyphenyl)-N-[1-(2-pyrrolidin-1-ylethyl)-1H-indazol-6-yl]propanamide;
3-[5-(4-methylphenyl)-1,3-oxazol-2-yl]-N-[1-(2-pyrrolidin-1-ylethyl)-1H-indazol-6-yl]propanamide;
2-[4-(benzyloxy)-3-methoxyphenyl]-N-[1-(2-pyrrolidin-1-ylethyl)-1H-indazol-6-yl]acetamide;
3-[4-(benzyloxy)-3-methoxyphenyl]-N-[1-(2-pyrrolidin-1-ylethyl)-1H-indazol-6-yl]propanamide;
2-(4-phenoxyphenyl)-N-[1-(2-pyrrolidin-1-ylethyl)-1H-indazol-6-yl]acetamide;
3-[4-(benzyloxy)phenyl]-N-[1-(2-pyrrolidin-1-ylethyl)-1H-indazol-6-yl]propanamide;
3-(4-phenoxypyridin-3-yl)-N-[1-(2-pyrrolidin-1-ylethyl)-1H-indazol-6-yl]propanamide;
2-{4-[(4-fluorobenzyl)oxy]phenyl}-N-[1-(2-pyrrolidin-1-ylethyl)-1H-indazol-6-yl]acetamide;
2-{4-[(3-fluorobenzyl)oxy]phenyl}-N-[1-(2-pyrrolidin-1-ylethyl)-1H-indazol-6-yl]acetamide;
2-(4-{[4-(difluoromethoxy)benzyl]oxy}phenyl)-N-[1-(2-pyrrolidin-1-ylethyl)-1H-indazol-6-yl]acetamide;
2-{4-[(3,5-dichlorobenzyl)oxy]phenyl}-N-[1-(2-pyrrolidin-1-ylethyl)-1H-indazol-6-yl]acetamide;
2-{4-[(3-cyanobenzyl)oxy]phenyl}-N-[1-(2-pyrrolidin-1-ylethyl)-1H-indazol-6-yl]acetamide;
N-[2-(4-phenoxyphenyl)ethyl]-N'-[1-(2-pyrrolidin-1-ylethyl)-1H-indazol-6-yl]urea;
N-(4-phenoxybenzyl)-N'-[1-(2-pyrrolidin-1-ylethyl)-1H-indazol-6-yl]urea;
N-[4-(benzyloxy)phenyl]-N'-[1-(2-pyrrolidin-1-ylethyl)-1H-indazol-6-yl]urea;
2-(3'-acetyl-1,1'-biphenyl-4-yl)-N-[1-(2-pyrrolidin-1-ylethyl)-1H-indazol-6-yl]acetamide;
N-[1-(2-pyrrolidin-1-ylethyl)-1H-indazol-6-yl]-2-[4'-(trifluoromethoxy)-1,1'-biphenyl-4-yl]acetamide;
2-(4'-fluoro-1,1'-biphenyl-4-yl)-N-[1-(2-pyrrolidin-1-ylethyl)-1H-indazol-6-yl]acetamide;
3-[(1,1'-biphenyl-4-ylmethyl)amino]-N-[1-(2-pyrrolidin-1-ylethyl)-1H-indazol-6-yl]propanamide;
3-[(3-phenoxybenzyl)amino]-N-[1-(2-pyrrolidin-1-ylethyl)-1H-indazol-6-yl]propanamide;
N-[1-(2-pyrrolidin-1-ylethyl)-1H-indazol-6-yl]-3-[(4-thien-2-ylbenzyl)amino]propanamide;
2-[(4-phenoxybenzyl)amino]-N-[1-(2-pyrrolidin-1-ylethyl)-1H-indazol-6-yl]acetamide;
2-{[(6-methoxy-2-naphthyl)methyl]amino}-N-[1-(2-pyrrolidin-1-ylethyl)-1H-indazol-6-yl]acetamide;
2-[(1,1'-biphenyl-4-ylmethyl)amino]-N-[1-(2-pyrrolidin-1-ylethyl)-1H-indazol-6-yl]acetamide;
2-[(3-phenoxybenzyl)amino]-N-[1-(2-pyrrolidin-1-ylethyl)-1H-indazol-6-yl]acetamide;
2-({[5-(2-chlorophenyl)-2-furyl]methyl}amino)-N-[1-(2-pyrrolidin-1-ylethyl)-1H-indazol-6-yl]acetamide;
N-{1-[2-(2,5-dimethylpyrrolidin-1-yl)ethyl]-1H-indazol-6-yl}-2-(4-phenoxyphenyl)acetamide;
N-{1-[2-(2-methylpyrrolidin-1-yl)ethyl]-1H-indazol-6-yl}-2-(4-phenoxyphenyl)acetamide;
2-(4-phenoxyphenyl)-N-[1-(3-pyrrolidin-1-ylpropyl)-1H-indazol-6-yl]acetamide;
N-(1-{3-[(2S)-2-(methoxymethyl)pyrrolidin-1-yl]propyl}-1H-indazol-6-yl)-2-(4-phenoxyphenyl)acetamide;
N-(1-{3-[(2S)-2-(hydroxymethyl)pyrrolidin-1-yl]propyl}-1H-indazol-6-yl)-2-(4-phenoxyphenyl)acetamide;
N-{1-[3-(2-methylpyrrolidin-1-yl)propyl]-1H-indazol-6-yl}-2-(4-phenoxyphenyl)acetamide;
2-[4-(benzyloxy)phenyl]-N-{1-[2-(2-oxo-1,3-oxazolidin-3-yl)ethyl]-1H-indazol-6-yl}acetamide;
2-[4-(benzyloxy)phenyl]-N-{1-[2-(2-oxopyrrolidin-1-yl)ethyl]-1H-indazol-6-yl}acetamide;
2-[4-(benzyloxy)phenyl]-N-{1-[2-(2,5-dioxopyrrolidin-1-yl)ethyl]-1H-indazol-6-yl}acetamide;
2-[4-(benzyloxy)phenyl]-N-[3-chloro-1-(2-pyrrolidin-1-ylethyl)-1H-indazol-4-yl]acetamide;

N-[3-chloro-1-(2-pyrrolidin-1-yl-ethyl)-1H-indazol-4-yl]-2-(4-phenoxy-phenyl)acetamide;
2-[4-(benzyloxy)phenyl]-N-[3-bromo-1-(2-pyrrolidin-1-ylethyl)-1H-indazol-4-yl]acetamide;
1-[3-chloro-1-(2-pyrrolidin-1-yl-ethyl)-1H-indazol-5-yl]-3-(4-phenoxy-phenyl)urea;
1-[3-bromo-1-(2-pyrrolidin-1-yl-ethyl)-1H-indazol-5-yl]-3-(4-phenoxy-phenyl)urea;
N-[3-bromo-1-(2-pyrrolidin-1-yl-ethyl)-1H-indazol-5-yl]-2-(4-phenoxy-phenyl)acetamide;
N-[3-chloro-1-(2-pyrrolidin-1-yl-ethyl)-1H-indazol-6-yl]-2-(4-phenoxy-phenyl)acetamide;
2-[4-(benzyloxy)phenyl]-N-[3-bromo-1-(2-pyrrolidin-1-ylethyl)-1H-indazol-6-yl]acetamide;
N-[3-bromo-1-(2-pyrrolidin-1-yl-ethyl)-1H-indazol-6-yl]-2-(4-phenoxy-phenyl)acetamide;
1-(4-phenoxyphenyl)-3-[1-(2-pyrrolidin-1-ylethyl)-1H-indazol-5-yl]-1,3-dihydro-2H-imidazol-2-one; and
1-(4-phenoxyphenyl)-3-[1-(2-pyrrolidin-1-ylethyl)-1H-indazol-5-yl]imidazolidin-2-one.

11. The compound according to claim 1 wherein
A is —C(O)—;
B or is selected from the group consisting of alkylene, alkenyl, —NR$_b$— and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—;
R$_1$ is selected from the group consisting of hydrogen and alkyl;
R$_2$ is selected from the group consisting of hydrogen, halogen, alkyl and alkoxy;
R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ taken together with the atoms to which they are attached form a 6 membered heterocycle;
Z is selected from the group consisting of hydrogen, alkyl and halogen; and
m is 1, 2 or 3;
provided that:
if B is NR$_b$— or NR$_b$-alkyl, then
D is selected from the group consisting of alkyl, aryl, arylalkyl, heterocycle and heterocyclealkyl.

12. The compound according to claim 1 wherein
A is —C(O)—;
B is selected from the group consisting of alkylene, alkenyl, —NR$_b$— and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—;
R$_1$ is selected from the group consisting of hydrogen and alkyl;
R$_2$ is selected from the group consisting of hydrogen, halogen, alkyl and alkoxy;
R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ taken together with the atoms to which they are attached form

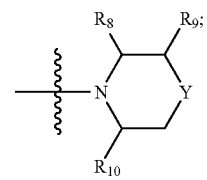

Y is selected from the group consisting of —O—, —NR$_j$—, —CHR$_j$— and —C(O)—;
Z is selected from the group consisting of hydrogen, alkyl and halogen;
R$_8$ is selected from the group consisting of hydrogen and alkyl; and
R$_9$ and R$_{10}$ are each individually selected from the group consisting of oxo, hydrogen and alkyl; and
m is 1, 2 or 3;
provided that:
if B is NR$_b$— or NR$_b$-alkyl, then
D is selected from the group consisting of alkyl, aryl, arylalkyl, heterocycle and heterocyclealkyl.

13. The compound according to claim 12, wherein the compound is selected from the group consisting of
N-[1-(2-morpholin-4-ylethyl)-1H-indazol-4-yl]-2-[(4-phenoxybenzyl)amino]acetamide;
2-[4-(benzyloxy)phenyl]-N-[1-(2-morpholin-4-ylethyl)-1H-indazol-4-yl]acetamide;
4-(1,1'-biphenyl-4-yl)-N-[1-(2-morpholin-4-ylethyl)-1H-indazol-4-yl]-4-oxobutanamide;
2-[(4-phenoxybenzyl)amino]-N-[1-(2-piperidin-1-yl-ethyl)-1H-indazol-4-yl]acetamide;
2-(4-phenoxyphenyl)-N-[1-(2-piperidin-1-ylethyl)-1H-indazol-4-yl]acetamide;
2-[4-(benzyloxy)phenyl]-N-(1-{2-[(2R)-2-methylpiperidin-1-yl]ethyl}-1H-indazol-4-yl)acetamide;
2-[4-(benzyloxy)phenyl]-N-(1-{2-[(3R)-3-methylpiperidin-1-yl]ethyl}-1H-indazol-4-yl)acetamide;
2-(4-phenoxy-phenyl)-N-[1-(2-piperidin-1-yl-ethyl)-1H-indazol-5-yl]-acetamide;
1-(4-phenoxy-phenyl)-3-[1-(2-piperidin-1-yl-ethyl)-1H-indazol-5-yl]-urea;
N-[1-(2-morpholin-4-yl-ethyl)-1H-indazol-5-yl]-2-(4-phenoxy-phenyl)-acetamide;
1-[1-(2-morpholin-4-yl-ethyl)-1H-indazol-5-yl]-3-(4-phenoxy-phenyl)-urea;
1-{2-[5-({[(4-phenoxyphenyl)amino]carbonyl}amino)-1H-indazol-1-yl]ethyl}piperidine-4-carboxamide;

N-{1-[2-(4-methylpiperidin-1-yl)ethyl]-1H-indazol-5-yl}-N'-(4-phenoxyphenyl)urea;
N-{1-[2-(3-methylpiperidin-1-yl)ethyl]-1H-indazol-5-yl}-N'-(4-phenoxyphenyl)urea;
N-{1-[2-(4-methylpiperazin-1-yl)ethyl]-1H-indazol-5-yl}-N'-(4-phenoxyphenyl)urea;
N-{1-[2-(2-methylpiperidin-1-yl)ethyl]-1H-indazol-5-yl}-N'-(4-phenoxyphenyl)urea;
N-{1-[2-(2-methylpiperidin-1-yl)ethyl]-1H-indazol-6-yl}-2-(4-phenoxyphenyl)acetamide;
N-{1-[2-(3-methylpiperidin-1-yl)ethyl]-1H-indazol-6-yl}-2-(4-phenoxyphenyl)acetamide;
N-{1-[2-(4-methylpiperidin-1-yl)ethyl]-1H-indazol-6-yl}-2-(4-phenoxyphenyl)acetamide;
N-{1-[3-(3-methylpiperidin-1-yl)propyl]-1H-indazol-6-yl}-2-(4-phenoxyphenyl)acetamide;
N-{1-[3-(4-hydroxypiperidin-1-yl)propyl]-1H-indazol-6-yl}-2-(4-phenoxyphenyl)acetamide;
N-{1-[3-(4-methylpiperidin-1-yl)propyl]-1H-indazol-6-yl}-2-(4-phenoxyphenyl)acetamide;
2-(4-phenoxyphenyl)-N-[1-(3-piperidin-1-ylpropyl)-1H-indazol-6-yl]acetamide;
N-[1-(3-morpholin-4-ylpropyl)-1H-indazol-6-yl]-2-(4-phenoxyphenyl)acetamide.

14. The compound according to claim 1 wherein
A is —C(O)—;
B is selected from the group consisting of alkylene, alkenyl, —NR$_b$— and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—;
R$_1$ is selected from the group consisting of hydrogen and alkyl;
R$_2$ is selected from the group consisting of hydrogen, halogen, alkyl and alkoxy;
R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ taken together with the atoms to which they are attached form a 7 membered heterocycle;
Z is selected from the group consisting of hydrogen, alkyl and halogen; and
m is 1, 2 or 3;
provided that:
if B is NR$_b$— or NR$_b$-alkyl, then
D is selected from the group consisting of alkyl, aryl, arylalkyl, heterocycle and heterocyclealkyl.

15. The compound according to claim 1 wherein
A is —C(O)—;
B is selected from the group consisting of alkylene, alkenyl, —NR$_b$— and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocyclealkyl-NH—, and heterocyclealkyl-O—;
R$_1$ is selected from the group consisting of hydrogen and alkyl;
R$_2$ is selected from the group consisting of hydrogen, halogen, alkyl and alkoxy;
R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ taken together with the atoms to which they are attached form

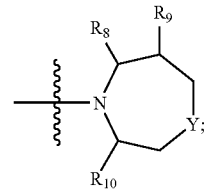

Y is selected from the group consisting of —O—, —NR$_j$—, —CHR$_j$— and —C(O)—;
Z is selected from the group consisting of hydrogen, alkyl and halogen;
R$_8$ is selected from the group consisting of hydrogen and alkyl;
R$_9$ and R$_{10}$ are each individually selected from the group consisting of oxo, hydrogen and alkyl; and
m is 1, 2 or 3;
provided that:
if B is NR$_b$— or NR$_b$-alkyl, then
D is selected from the group consisting of alkyl, aryl, arylalkyl, heterocycle and heterocyclealkyl.

16. The compound according to claims 15, that is
N-[1-(2-azepan-1-ylethyl)-1H-indazol-5-yl]-N'-(4-phenoxyphenyl)urea;
N-[1-(3-azepan-1-ylpropyl)-1H-indazol-6-yl]-2-(4-phenoxyphenyl)acetamide.

17. A pharmaceutical composition comprising a therapeutically effective amount of a compound of formula (I) in combination with a pharmaceutically suitable carrier.

18. A method of treating obesity by inhibiting the effects of melanin concentrating hormone (MCH) through the melanin concentrating hormone receptor, comprising administrering a therapeutically effective amount of a compound of formula (I).

19. A method of treating abnormalities in reproduction and sexual behavior, thyroid hormone secretion, diuresis and water/electrolyte homeostasis, sensory processing, memory, sleeping and arousal, anxiety and depression, and seizure by inhibiting the effects of melanin concentrating hormone (MCH) through the melanin concentrating hormone receptor, comprising administrering a therapeutically effective amount of a compound of formula (I).

* * * * *